(12) United States Patent
Yoshida et al.

(10) Patent No.: US 12,201,584 B2
(45) Date of Patent: * Jan. 21, 2025

(54) ANAEROBIC BLOOD STORAGE CONTAINERS

(71) Applicant: Hemanext Inc., Lexington, MA (US)

(72) Inventors: Tatsuro Yoshida, West Newton, MA (US); Rafael Cordero, Bedford, MA (US); Jancarlo Sarita, Lynn, MA (US); Michael Zocchi, Arlington, VA (US); Michael Wolf, Brookline, MA (US); Philip Michael Keegan, Newton, MA (US); Narendran Renganathan, Plano, TX (US); Jeffrey Karl Sutton, Medway, MA (US)

(73) Assignee: Hemanext Inc., Lexington, MA (US)

( * ) Notice: Subject to any disclaimer, the term of this patent is extended or adjusted under 35 U.S.C. 154(b) by 1133 days.

This patent is subject to a terminal disclaimer.

(21) Appl. No.: 17/072,250

(22) Filed: Oct. 16, 2020

(65) Prior Publication Data

US 2021/0100721 A1 Apr. 8, 2021

Related U.S. Application Data

(63) Continuation of application No. 15/708,925, filed on Sep. 19, 2017, now Pat. No. 10,849,824, which is a
(Continued)

(51) Int. Cl.
*A61J 1/10* (2006.01)
*A01N 1/02* (2006.01)
(Continued)

(52) U.S. Cl.
CPC .............. *A61J 1/10* (2013.01); *A01N 1/0263* (2013.01); *A61J 1/1462* (2013.01); *A61J 1/1468* (2015.05);
(Continued)

(58) Field of Classification Search
CPC .......... A61J 1/10; A61J 1/1462; A61J 1/1468; A61J 1/18; A61J 1/1475
See application file for complete search history.

(56) References Cited

U.S. PATENT DOCUMENTS 3,064,647 A 11/1962 Earl
3,361,041 A 1/1968 Grob
(Continued)

FOREIGN PATENT DOCUMENTS

AU 2012279043 7/2016
CA 2184868 A1 3/1997
(Continued)

OTHER PUBLICATIONS

U.S. Appl. No. 10/295,781, filed Nov. 15, 2002, Bitensky et al.
(Continued)

*Primary Examiner* — Leslie R Deak
(74) *Attorney, Agent, or Firm* — Arnold & Porter Kaye Scholer

(57) ABSTRACT

A blood storage container for the anaerobic storage of blood, having enhanced sealing methods and materials for the preservation of stored blood is provided.

20 Claims, 19 Drawing Sheets

Related U.S. Application Data continuation of application No. 15/475,898, filed on Mar. 31, 2017, now Pat. No. 9,801,784, which is a continuation of application No. PCT/US2016/029069, filed on Apr. 22, 2016.

(60) Provisional application No. 62/151,957, filed on Apr. 23, 2015, provisional application No. 62/151,839, filed on Apr. 23, 2015.

(51) Int. Cl.
| | |
|---|---|
| *A61J 1/14* | (2023.01) |
| *A61J 1/18* | (2023.01) |
| *B32B 1/00* | (2006.01) |
| *B32B 3/06* | (2006.01) |
| *B32B 3/08* | (2006.01) |
| *B32B 7/12* | (2006.01) |
| *B32B 27/08* | (2006.01) |
| *B32B 27/18* | (2006.01) |
| *B32B 27/20* | (2006.01) |
| *B32B 27/28* | (2006.01) |
| *B32B 27/30* | (2006.01) |
| *B32B 27/32* | (2006.01) |
| *B32B 27/34* | (2006.01) |
| *B32B 27/36* | (2006.01) |
| *B65D 81/26* | (2006.01) |
| *A61M 1/02* | (2006.01) |

(52) U.S. Cl.
CPC ............ *A61J 1/1475* (2013.01); *A61J 1/1487* (2015.05); *A61J 1/18* (2013.01); *B32B 1/00* (2013.01); *B32B 3/06* (2013.01); *B32B 3/08* (2013.01); *B32B 7/12* (2013.01); *B32B 27/08* (2013.01); *B32B 27/18* (2013.01); *B32B 27/205* (2013.01); *B32B 27/286* (2013.01); *B32B 27/306* (2013.01); *B32B 27/32* (2013.01); *B32B 27/34* (2013.01); *B32B 27/36* (2013.01); *B65D 81/268* (2013.01); *A61M 1/0209* (2013.01); *B32B 2250/24* (2013.01); *B32B 2307/308* (2013.01); *B32B 2307/412* (2013.01); *B32B 2307/414* (2013.01); *B32B 2307/514* (2013.01); *B32B 2307/7242* (2013.01); *B32B 2307/7244* (2013.01); *B32B 2307/7246* (2013.01); *B32B 2307/7265* (2013.01); *B32B 2439/80* (2013.01); *B32B 2535/00* (2013.01); *B65D 81/266* (2013.01)

(56) References Cited

U.S. PATENT DOCUMENTS

| | | | |
|---|---|---|---|
| 3,668,837 A | 6/1972 | Gross | |
| 3,668,838 A | 6/1972 | McNeil et al. | |
| 3,803,810 A | 4/1974 | Rosenberg | |
| 3,910,841 A | 10/1975 | Esmond | |
| 3,942,529 A | 3/1976 | Waage | |
| 4,075,091 A | 2/1978 | Bellhouse | |
| 4,086,924 A | 5/1978 | Latham, Jr. | |
| 4,093,515 A | 6/1978 | Kolobow | |
| 4,131,200 A | 12/1978 | Rinfret | |
| 4,162,676 A | 7/1979 | Talcott | |
| 4,199,062 A | 4/1980 | Johnston et al. | |
| 4,222,379 A | 9/1980 | Smith | |
| 4,225,439 A | 9/1980 | Spranger | |
| 4,228,032 A | 10/1980 | Talcott | |
| 4,253,458 A | 3/1981 | Bacehowski et al. | |
| 4,256,692 A | 3/1981 | Cover | |
| 4,262,581 A | 4/1981 | Ferrell | |
| 4,300,559 A | 11/1981 | Gajewski et al. | |
| 4,314,480 A | 2/1982 | Becker | |
| 4,342,723 A | 8/1982 | Sado et al. | |
| 4,366,179 A | 12/1982 | Nawata et al. | |
| 4,370,160 A | 1/1983 | Ziemelis | |
| 4,381,775 A | 5/1983 | Nose' et al. | |
| 4,386,069 A | 5/1983 | Estep | |
| 4,398,642 A | 8/1983 | Okudaira et al. | |
| 4,440,815 A | 4/1984 | Zomorodi et al. | |
| 4,455,299 A | 6/1984 | Grode | |
| 4,540,416 A | 9/1985 | Hattori et al. | |
| 4,568,328 A | 2/1986 | King et al. | |
| 4,572,899 A | 2/1986 | Walker et al. | |
| 4,579,223 A | 4/1986 | Otsuka et al. | |
| 4,585,735 A | 4/1986 | Meryman et al. | |
| 4,609,383 A | 9/1986 | Bonaventura et al. | |
| 4,629,544 A | 12/1986 | Bonaventura et al. | |
| 4,639,353 A | 1/1987 | Takemura et al. | |
| 4,654,053 A | 3/1987 | Sievers et al. | |
| 4,659,549 A | 4/1987 | Hamada et al. | |
| 4,670,013 A | 6/1987 | Barnes et al. | |
| 4,701,267 A | 10/1987 | Watanabe et al. | |
| 4,713,176 A | 12/1987 | Schoendorfer et al. | |
| 4,731,978 A | 5/1988 | Martensson | |
| 4,748,121 A | 5/1988 | Beaver et al. | |
| 4,749,551 A | 6/1988 | Borgione | |
| 4,769,175 A | 9/1988 | Inoue | |
| 4,769,318 A | 9/1988 | Hamasaki et al. | |
| 4,798,728 A | 1/1989 | Sugisawa | |
| 4,828,561 A | 5/1989 | Woodroof | |
| 4,837,047 A | 6/1989 | Sato et al. | |
| 4,859,360 A | 8/1989 | Suzuki et al. | |
| 4,861,867 A | 8/1989 | Estep | |
| 4,880,548 A | 11/1989 | Pall et al. | |
| 4,880,786 A | 11/1989 | Sasakawa et al. | |
| 4,902,701 A | 2/1990 | Batchelor et al. | |
| 4,925,572 A | 5/1990 | Pall | |
| 4,986,837 A | 1/1991 | Shibata | |
| 4,998,990 A | 3/1991 | Richter et al. | |
| 5,000,848 A | 3/1991 | Hodgins et al. | |
| 5,023,054 A | 6/1991 | Sato et al. | |
| 5,037,419 A | 8/1991 | Valentine et al. | |
| 5,120,659 A | 6/1992 | King et al. | |
| 5,137,531 A | 8/1992 | Lee et al. | |
| 5,139,668 A | 8/1992 | Pan et al. | |
| 5,143,763 A | 9/1992 | Yamada et al. | |
| 5,152,905 A | 10/1992 | Pall et al. | |
| 5,192,320 A | 3/1993 | Anazawa et al. | |
| 5,194,158 A | 3/1993 | Matson | |
| 5,208,335 A | 5/1993 | Ramprasad et al. | |
| 5,229,012 A | 7/1993 | Pall et al. | |
| 5,254,248 A | 10/1993 | Nakamura et al. | |
| 5,286,407 A | 2/1994 | Inoue et al. | |
| 5,328,268 A | 7/1994 | LaFleur | |
| 5,353,793 A | 10/1994 | Bornn | |
| 5,356,375 A | 10/1994 | Higley | |
| 5,360,734 A | 11/1994 | Chapman et al. | |
| 5,362,442 A | 11/1994 | Kent | |
| 5,368,808 A | 11/1994 | Koike et al. | |
| 5,382,526 A | 1/1995 | Gajewski et al. | |
| 5,386,014 A | 1/1995 | Nho et al. | |
| 5,387,624 A | 2/1995 | Morita et al. | |
| 5,417,986 A | 5/1995 | Reid et al. | |
| 5,427,663 A | 6/1995 | Austin et al. | |
| 5,443,743 A | 8/1995 | Gsell | |
| 5,449,617 A | 9/1995 | Falkenberg et al. | |
| 5,476,764 A | 12/1995 | Bitensky | |
| 5,506,141 A | 4/1996 | Weinreb et al. | |
| 5,529,821 A | 6/1996 | Ishikawa et al. | |
| 5,605,934 A | 2/1997 | Giertych | |
| 5,617,873 A | 4/1997 | Yost et al. | |
| 5,624,794 A | 4/1997 | Bitensky et al. | |
| 5,635,358 A | 6/1997 | Wilding et al. | |
| 5,686,304 A | 11/1997 | Codner | |
| 5,691,452 A | 11/1997 | Gawryl et al. | |
| 5,693,122 A | 12/1997 | Berndt | |
| 5,693,230 A | 12/1997 | Asher | |
| 5,698,250 A | 12/1997 | DelDuca et al. | |
| 5,709,472 A | 1/1998 | Prusik et al. | |
| 5,744,056 A | 4/1998 | Venkateshwaran et al. | |
| 5,730,989 A | 5/1998 | Wright | |

(56) References Cited

U.S. PATENT DOCUMENTS

| | | |
|---|---|---|
| 5,750,115 A | 5/1998 | Van Den Bosch |
| 5,783,094 A | 7/1998 | Kraus et al. |
| 5,783,148 A | 7/1998 | Cottingham et al. |
| 5,789,151 A | 8/1998 | Bitensky et al. |
| 5,789,152 A | 8/1998 | Black et al. |
| 5,811,142 A | 9/1998 | DelDuca et al. |
| 5,846,427 A | 12/1998 | Kessler et al. |
| 5,858,015 A | 1/1999 | Fini |
| 5,858,643 A | 1/1999 | Ben-Hur et al. |
| 5,863,460 A | 1/1999 | Slovacek et al. |
| 5,895,810 A | 4/1999 | Light et al. |
| 5,902,747 A | 5/1999 | Nemser et al. |
| 5,906,285 A | 5/1999 | Slat |
| 5,928,178 A | 7/1999 | Samolyk |
| 5,955,519 A | 9/1999 | Neri |
| 5,962,650 A | 10/1999 | Osterberg et al. |
| 5,972,710 A | 10/1999 | Weigl et al. |
| 6,007,529 A | 12/1999 | Gustafsson et al. |
| 6,027,623 A | 2/2000 | Ohkawa |
| 6,042,264 A | 3/2000 | Prusik et al. |
| 6,045,701 A | 4/2000 | Ung-Chhun et al. |
| 6,047,203 A | 4/2000 | Sackner et al. |
| 6,068,152 A | 5/2000 | Meiners et al. |
| 6,076,664 A | 6/2000 | Yeager |
| 6,080,322 A | 6/2000 | Deniega et al. |
| 6,090,062 A | 7/2000 | Sood et al. |
| 6,097,293 A | 8/2000 | Galloway et al. |
| 6,148,536 A | 11/2000 | Iijima |
| 6,150,085 A | 11/2000 | Hess et al. |
| 6,156,231 A | 12/2000 | McKedy |
| 6,162,396 A | 12/2000 | Bitensky et al. |
| 6,164,821 A | 12/2000 | Randall |
| 6,187,572 B1 | 2/2001 | Platz et al. |
| 6,210,601 B1 | 4/2001 | Hottle et al. |
| 6,231,770 B1 | 5/2001 | Bormann et al. |
| 6,248,690 B1 | 6/2001 | McKedy |
| 6,254,628 B1 | 7/2001 | Wallace et al. |
| 6,287,284 B1 | 9/2001 | Woarburton-Pitt |
| 6,287,289 B1 | 9/2001 | Niedospial, Jr. |
| 6,315,815 B1 | 11/2001 | Spadaccini |
| 6,337,026 B1 | 1/2002 | Lee et al. |
| 6,358,678 B1 | 3/2002 | Bakaltcheva et al. |
| 6,368,871 B1 | 4/2002 | Christel et al. |
| 6,387,461 B1 | 5/2002 | Ebner et al. |
| 6,402,818 B1 | 6/2002 | Sengupta et al. |
| 6,403,124 B1 | 6/2002 | Dottori |
| 6,413,713 B1 | 7/2002 | Serebrennikov |
| 6,436,872 B2 | 8/2002 | McKedy |
| 6,439,577 B2 | 8/2002 | Jorgensen et al. |
| 6,447,987 B1 | 9/2002 | Hess et al. |
| 6,468,732 B1 | 10/2002 | Malin et al. |
| 6,475,147 B1 | 11/2002 | Yost et al. |
| 6,479,252 B1 | 11/2002 | Barbera-Guillem et al. |
| 6,482,585 B2 | 11/2002 | Dottori |
| 6,494,909 B2 | 12/2002 | Greenhalgh |
| 6,527,957 B1 | 3/2003 | Denienga et al. |
| 6,558,571 B1 | 5/2003 | Powers |
| 6,564,207 B1 | 5/2003 | Abdoh |
| 6,582,496 B1 | 6/2003 | Cheng et al. |
| 6,610,772 B1 | 8/2003 | Clauberg et al. |
| 6,626,884 B1 | 9/2003 | Dillon et al. |
| 6,688,476 B2 | 2/2004 | Breillatt, Jr. et al. |
| 6,695,803 B1 | 2/2004 | Robinson et al. |
| 6,697,667 B1 | 2/2004 | Lee et al. |
| 6,709,492 B1 | 3/2004 | Spadaccini |
| 6,723,051 B2 | 4/2004 | Davidson et al. |
| 6,761,695 B2 | 7/2004 | Yost et al. |
| 6,773,407 B2 | 8/2004 | Yost et al. |
| 6,808,675 B1 | 10/2004 | Coelho et al. |
| 6,817,979 B2 | 11/2004 | Nihtilä |
| 6,866,783 B2 | 3/2005 | Baurmeister et al. |
| 6,878,335 B2 | 4/2005 | Britten et al. |
| 6,899,822 B2 | 5/2005 | McKedy |
| 6,955,648 B2 | 10/2005 | Mozayeni et al. |
| 6,977,105 B1 | 12/2005 | Fujieda et al. |
| 7,041,800 B1 | 5/2006 | Gawryl et al. |
| 7,097,690 B2 | 8/2006 | Usher et al. |
| 7,104,958 B2 | 9/2006 | Crutchfield et al. |
| 7,125,498 B2 | 10/2006 | McKedy |
| 7,208,120 B2 | 4/2007 | Bitensky et al. |
| 7,347,887 B2 | 3/2008 | Bulow et al. |
| 7,361,277 B2 | 4/2008 | Bormann et al. |
| 7,431,995 B2 | 10/2008 | Smith et al. |
| 7,452,601 B2 | 11/2008 | Ebner et al. |
| 7,517,146 B2 | 4/2009 | Smith et al. |
| 7,666,486 B2 | 2/2010 | Sato et al. |
| 7,713,614 B2 | 5/2010 | Chow et al. |
| 7,721,898 B2 | 5/2010 | Yagi et al. |
| 7,723,017 B2 | 5/2010 | Bitensky et al. |
| 7,754,798 B2 | 7/2010 | Ebner et al. |
| 7,763,097 B2 | 7/2010 | Federspiel |
| 7,775,376 B2 | 8/2010 | Bonaguidi et al. |
| 7,784,619 B2 | 8/2010 | Jacobson |
| 8,070,664 B2 | 12/2011 | Rochat |
| 8,071,282 B2 | 12/2011 | Bitensky et al. |
| 8,535,421 B2 | 9/2013 | Yoshida et al. |
| 8,569,052 B2 | 10/2013 | Federspiel et al. |
| 8,864,735 B2 | 10/2014 | Sano et al. |
| 8,877,508 B2 | 11/2014 | Hyde et al. |
| 8,887,721 B2 | 11/2014 | Zapol et al. |
| 9,005,343 B2 | 4/2015 | Yoshida et al. |
| 9,067,004 B2 | 6/2015 | Yoshida et al. |
| 9,199,016 B2 | 12/2015 | Yoshida et al. |
| 9,296,990 B2 | 3/2016 | Federspiel et al. |
| 9,539,375 B2 | 1/2017 | Yoshida et al. |
| 9,801,784 B2 * | 10/2017 | Yoshida ............... A61J 1/1462 |
| 9,844,615 B2 | 12/2017 | Yoshida et al. |
| 10,603,417 B2 | 3/2020 | Yoshida et al. |
| 2001/0027156 A1 | 10/2001 | Egozy et al. |
| 2001/0037078 A1 | 11/2001 | Lynn et al. |
| 2001/0049089 A1 | 12/2001 | Dottori |
| 2002/0062078 A1 | 5/2002 | Crutchfield et al. |
| 2002/0066699 A1 | 6/2002 | Boggs et al. |
| 2002/0085952 A1 | 7/2002 | Ellingboe et al. |
| 2002/0086329 A1 | 7/2002 | Shvets et al. |
| 2002/0099570 A1 | 7/2002 | Knight |
| 2002/0176798 A1 | 11/2002 | Linker et al. |
| 2002/0182241 A1 | 12/2002 | Borenstein et al. |
| 2003/0003575 A1 | 1/2003 | Vacanti et al. |
| 2003/0039582 A1 | 2/2003 | Chambers et al. |
| 2003/0040835 A1 | 2/2003 | Ng et al. |
| 2003/0062299 A1 | 4/2003 | Lee et al. |
| 2003/0106861 A1 | 6/2003 | Gibbs et al. |
| 2003/0124504 A1 | 7/2003 | Bitensky et al. |
| 2003/0153074 A1 | 8/2003 | Bitensky et al. |
| 2003/0183801 A1 | 10/2003 | Yang et al. |
| 2003/0189003 A1 | 10/2003 | Kraus et al. |
| 2003/0190272 A1 | 10/2003 | Raine et al. |
| 2003/0201160 A1 | 10/2003 | Goodrich et al. |
| 2003/0215784 A1 | 11/2003 | Dumont et al. |
| 2003/0233934 A1 | 12/2003 | Wijmans et al. |
| 2004/0013566 A1 | 1/2004 | Myrick et al. |
| 2004/0026341 A1 | 2/2004 | Hogberg et al. |
| 2004/0097862 A1 | 5/2004 | Lampeter et al. |
| 2004/0126880 A1 | 7/2004 | Manders et al. |
| 2004/0146671 A1 | 7/2004 | Szabo et al. |
| 2004/0168982 A1 | 9/2004 | Bitensky et al. |
| 2004/0254560 A1 | 12/2004 | Coelho et al. |
| 2005/0038342 A1 | 2/2005 | Mozayeni et al. |
| 2005/0085785 A1 | 4/2005 | Shang et al. |
| 2005/0137517 A1 | 6/2005 | Blickhan et al. |
| 2005/0139806 A1 | 6/2005 | Havens et al. |
| 2005/0208462 A1 | 9/2005 | Bitensky et al. |
| 2005/0210141 A1 | 9/2005 | Oyama et al. |
| 2005/0230856 A1 | 10/2005 | Parekh et al. |
| 2005/0233302 A1 | 10/2005 | Hess et al. |
| 2006/0081524 A1 | 4/2006 | Sengupta et al. |
| 2006/0118479 A1 | 6/2006 | Shevkoplyas et al. |
| 2006/0160724 A1 | 7/2006 | Gawryl et al. |
| 2006/0169138 A1 | 8/2006 | Schmidt |
| 2006/0226087 A1 | 10/2006 | Robinson et al. |
| 2006/0278073 A1 | 12/2006 | McHugh |
| 2007/0078113 A1 | 4/2007 | Roth et al. |
| 2007/0099170 A1 | 5/2007 | Goodrich et al. |

(56) References Cited

U.S. PATENT DOCUMENTS

| | | |
|---|---|---|
| 2007/0207186 A1 | 9/2007 | Scanlon et al. |
| 2007/0240569 A1 | 10/2007 | Ooya |
| 2007/0276508 A1 | 11/2007 | Fischer et al. |
| 2008/0027368 A1 | 1/2008 | Kollar et al. |
| 2008/0098894 A1 | 5/2008 | Sabatino |
| 2008/0160107 A1 | 7/2008 | McCaney et al. |
| 2008/0234327 A1 | 9/2008 | Cadieux et al. |
| 2008/0243045 A1 | 10/2008 | Pasqualini |
| 2008/0276803 A1 | 11/2008 | Molaison et al. |
| 2008/0299538 A1 | 12/2008 | Goodrich et al. |
| 2009/0017128 A1 | 1/2009 | Monzyk et al. |
| 2009/0084720 A1 | 4/2009 | Dannenmaier et al. |
| 2009/0235619 A1 | 9/2009 | Ostler et al. |
| 2009/0269837 A1 | 10/2009 | Shevkoplyas et al. |
| 2010/0021879 A1 | 1/2010 | Delgado et al. |
| 2010/0133203 A1 | 6/2010 | Walker et al. |
| 2010/0221697 A1 | 9/2010 | Sehgal |
| 2010/0282662 A1 | 11/2010 | Lee et al. |
| 2010/0294128 A1 | 11/2010 | Schmidt |
| 2010/0313755 A1 | 12/2010 | Koros et al. |
| 2010/0331767 A1 | 12/2010 | Frankowski |
| 2011/0092875 A1 | 4/2011 | Beck |
| 2012/0024156 A1 | 2/2012 | Yoshida et al. |
| 2012/0077182 A1 | 3/2012 | Bitensky et al. |
| 2012/0100523 A1 | 4/2012 | Federspiel et al. |
| 2012/0115124 A1 | 5/2012 | Yoshida et al. |
| 2012/0129148 A1 | 5/2012 | Hess et al. |
| 2012/0129149 A1 | 5/2012 | Federspiel et al. |
| 2012/0146266 A1 | 6/2012 | Oda et al. |
| 2012/0219633 A1 | 8/2012 | Sowemimo-Coker |
| 2013/0004586 A1 | 1/2013 | Vachon et al. |
| 2013/0004937 A1 | 1/2013 | Yoshida et al. |
| 2013/0144266 A1 | 6/2013 | Borenstein et al. |
| 2013/0197420 A1 | 8/2013 | Fissell, IV et al. |
| 2013/0259744 A1 | 10/2013 | Yoshida et al. |
| 2013/0327677 A1 | 12/2013 | McDorman |
| 2014/0012185 A1 | 1/2014 | Ishizuka et al. |
| 2014/0091047 A1* | 4/2014 | Radwanski .......... A61J 1/10 424/93.73 |
| 2014/0134503 A1 | 5/2014 | Lockett et al. |
| 2014/0146266 A1 | 5/2014 | Zhang |
| 2014/0158604 A1 | 6/2014 | Chammas et al. |
| 2014/0248005 A1 | 9/2014 | David et al. |
| 2015/0306288 A1 | 10/2015 | Delorme et al. |
| 2016/0007588 A1 | 1/2016 | Levesque et al. |
| 2016/0242410 A9 | 8/2016 | Yoshida et al. |
| 2018/0087997 A1 | 3/2018 | Thenard et al. |
| 2018/0094269 A1 | 4/2018 | Miller et al. |
| 2019/0275152 A1 | 9/2019 | Sowemimo-Coker et al. |

FOREIGN PATENT DOCUMENTS

| | | |
|---|---|---|
| CA | 2477946 | 9/2003 |
| CN | 11959965 A | 10/1998 |
| CN | 2502700 Y | 7/2002 |
| CN | 1642628 A | 7/2005 |
| CN | 2780207 Y | 5/2006 |
| CN | 2894710 Y | 5/2007 |
| CN | 101039737 A | 9/2007 |
| CN | 102711865 A | 10/2012 |
| CN | 103732056 | 4/2014 |
| DE | 3722984 | 1/1989 |
| DE | 10327988 A1 | 7/2004 |
| EP | 0 100 419 A2 | 2/1984 |
| EP | 0 217 759 A1 | 4/1987 |
| EP | 0 299 381 A2 | 1/1989 |
| EP | 0 890 368 A1 | 1/1999 |
| EP | 1 245 217 A2 | 10/2002 |
| EP | 1109447 | 10/2003 |
| EP | 1 891 999 A1 | 2/2008 |
| EP | 2389064 | 11/2011 |
| EP | 2635114 | 9/2013 |
| EP | 2459247 A2 | 3/2016 |
| EP | 3 285 711 A1 | 10/2016 |
| EP | 3 268 015 A1 | 1/2018 |
| FR | 2 996 413 A1 | 4/2014 |
| GB | 1 044 649 A2 | 10/1966 |
| GB | 2283015 A1 | 4/1995 |
| JP | S57-3652 A | 1/1982 |
| JP | 58-194879 | 11/1983 |
| JP | 59-115349 | 7/1984 |
| JP | 61-109577 A | 5/1986 |
| JP | 2 581 289 A1 | 11/1986 |
| JP | 63-63616 A | 3/1988 |
| JP | 01-013860 | 3/1989 |
| JP | 01-104271 A | 4/1989 |
| JP | 3-284263 | 12/1991 |
| JP | H 04-364850 | 12/1992 |
| JP | 5-503075 A | 5/1993 |
| JP | 5-503304 A | 6/1993 |
| JP | H05-148151 A | 6/1993 |
| JP | H05-237162 | 9/1993 |
| JP | 5-305123 A | 11/1993 |
| JP | H05-317413 | 12/1993 |
| JP | 06-121920 A | 5/1994 |
| JP | 2668446 | 7/1997 |
| JP | 2700170 B2 | 1/1998 |
| JP | H 10-501443 A | 2/1998 |
| JP | H10-507395 | 7/1998 |
| JP | 11-216179 | 8/1999 |
| JP | 2000-516963 A | 12/2000 |
| JP | 2001-500053 | 1/2001 |
| JP | 2001-523225 | 11/2001 |
| JP | 2002-087971 | 3/2002 |
| JP | 2002-253936 A | 9/2002 |
| JP | 2002-541941 | 12/2002 |
| JP | 2003-010287 | 1/2003 |
| JP | 2004-089495 A | 3/2004 |
| JP | 2004-514680 | 5/2004 |
| JP | 2004-520448 | 7/2004 |
| JP | 2004-244044 | 9/2004 |
| JP | 2005-533041 A | 11/2005 |
| JP | 2005-535279 A | 11/2005 |
| JP | 2005-535289 A | 11/2005 |
| JP | 2006-502078 A | 1/2006 |
| JP | 2006-515279 | 5/2006 |
| JP | 2006-213923 | 8/2006 |
| JP | 2007-260393 A | 10/2007 |
| JP | 2008-86996 | 4/2008 |
| JP | 2008-518952 | 6/2008 |
| JP | 2008-528066 | 7/2008 |
| JP | 2008-529550 A | 8/2008 |
| JP | 2008-253452 | 10/2008 |
| JP | 2009-513235 | 4/2009 |
| JP | 10/501443 | 2/2010 |
| JP | 2010-503501 A | 2/2010 |
| JP | 2010-509353 | 3/2010 |
| JP | 2010-116626 | 5/2010 |
| JP | 2010-535235 | 11/2010 |
| JP | 2010-538735 | 12/2010 |
| JP | 2011 000132 A | 1/2011 |
| JP | 2011-92905 | 5/2011 |
| JP | 2011-516570 A | 5/2011 |
| JP | 2013-500794 | 1/2013 |
| JP | 2013-507226 | 3/2013 |
| JP | 2014-501501 | 1/2014 |
| JP | 2014-518283 | 7/2014 |
| JP | 2014-527436 | 10/2014 |
| JP | 2007-509206 A | 4/2017 |
| KR | 10-0721054 | 5/2006 |
| SU | 1718766 A1 | 1/1990 |
| WO | WO 1981/02239 A1 | 8/1981 |
| WO | WO 1986/00809 A1 | 2/1986 |
| WO | WO 1989/02274 A1 | 3/1989 |
| WO | WO 1991/04659 A1 | 4/1991 |
| WO | WO 1992/08348 A1 | 5/1992 |
| WO | WO 1995/29662 A2 | 11/1995 |
| WO | WO 1996/29103 A1 | 9/1996 |
| WO | WO 1996/29346 A1 | 9/1996 |
| WO | WO 1996/29864 A1 | 10/1996 |
| WO | WO 1996/39026 A1 | 12/1996 |
| WO | WO 1997/37628 A1 | 10/1997 |
| WO | WO 1998/046073 A1 | 10/1998 |

(56) References Cited

FOREIGN PATENT DOCUMENTS

| | | |
|---|---|---|
| WO | WO 1998/51147 A1 | 11/1998 |
| WO | WO 1999/25726 A1 | 5/1999 |
| WO | WO 1999/29346 A1 | 6/1999 |
| WO | WO 1999/36330 A1 | 7/1999 |
| WO | WO 1999/48963 A2 | 9/1999 |
| WO | WO 2000/011946 A2 | 3/2000 |
| WO | WO 2000/0062891 | 10/2000 |
| WO | WO 01/10470 A1 | 2/2001 |
| WO | WO 2002/043485 | 6/2002 |
| WO | WO 2002/096471 | 12/2002 |
| WO | WO 2003/043419 A1 | 5/2003 |
| WO | WO 2003/043571 A2 | 5/2003 |
| WO | WO 2003/086577 A1 | 10/2003 |
| WO | WO 03/103390 A1 | 12/2003 |
| WO | WO 2004/043381 A2 | 5/2004 |
| WO | WO 2006/050328 A1 | 5/2006 |
| WO | WO 2006/057473 A1 | 6/2006 |
| WO | WO 2006/088455 A1 | 8/2006 |
| WO | WO 2008/063868 | 5/2008 |
| WO | WO 2009/126786 A2 | 10/2009 |
| WO | WO 2009/132839 A1 | 11/2009 |
| WO | WO 2011/014855 A2 | 2/2011 |
| WO | WO 2011/046841 A1 | 4/2011 |
| WO | WO 2011/046963 A1 | 4/2011 |
| WO | WO 2011/068897 A1 | 6/2011 |
| WO | WO 2012/027582 A1 | 3/2012 |
| WO | WO 2012/061731 A1 | 5/2012 |
| WO | WO 2012/120927 A1 | 9/2012 |
| WO | WO 2013/006631 A1 | 1/2013 |
| WO | WO 2013/022491 A1 | 2/2013 |
| WO | WO 2013/023156 A1 | 2/2013 |
| WO | WO 2013/043658 A1 | 3/2013 |
| WO | WO 2013/153441 A1 | 10/2013 |
| WO | WO 2013/177339 A1 | 11/2013 |
| WO | WO 2014/006238 | 1/2014 |
| WO | WO 2014/134503 A1 | 9/2014 |
| WO | WO 2014/194931 A1 | 12/2014 |
| WO | WO 2016/145210 A1 | 9/2016 |
| WO | WO 2016/172645 A1 | 10/2016 |
| WO | WO 2017/205590 A2 | 11/2017 |

OTHER PUBLICATIONS

U.S. Appl. No. 62/131,130, filed Mar. 15, 2015, Wolf et al.
U.S. Appl. No. 62/151,957, filed Apr. 23, 2015, Yoshida et al.
U.S. Appl. No. 12/901,350, filed Oct. 8, 2010, Yoshida et al.
Agarwal et al., "Effect of pre-storage gamma irradiation on red blood cells," *Indian Journal of Medical Research* 122(5):385 (2005).
Alcantar et al., "Polyethylene glycol-coated biocompatible surfaces," *Journal of Biomedical Materials Research*, 51(3):343-351 (2000).
Anderson et al., "Microfabrication and microfluidics for tissue engineering: state of the art and future opportunities," *Lab Chip*, 4:98-103 (2004).
Apstein et al., "Effect of erythrocyte storage and oxyhemoglobin affinity changes on cardiac function," *Am J. Physiol* 248: H508-15 (1985).
Aydogan et al., "Impaired erythrocytes deformability in $H_2O_2$-induced oxidative stress: protective effect of L-carnosine," *Clin Hemorheol Microcirc* 39: 93-8 (2008).
Babic, "In vitro function and phagocytosis of galactosylated platelet concentrates after longterm refrigeration," *Transfusion* 47: 442-51 (2007).
Barbee et al., "The Fahraeus Effect," *Microvascular Research*, 3:6-16 (1971).
Barclay et al., "A Method for Detecting Chaos in Canine Myocardial Microcirculatory Red Cell Flux," *Microcirculation*, 7(5):335-346 (2000).
Bardy et al., "Technetium-99m Labeling by Means of Stannous Pyrophosphate: Application to Bleomycin and Red Blood Cells," *Journal of Nuclear Medicine*, 16(5):435-437 (1975).

Barras et al., "Influence of Rejuvenation on the Rheological Properties of Stored Erythrocytes," *VASA*, 23(4):305-311 (1994).
Becker et al., "Studies of platelet concentrates stored at 22 C nad 4 C," *Transfusion* 13: 61-8 (1973).
Benesch et al., "The effect of organic phosphates from the human erythrocyte on the allosteric properties of hemoglobin," *Biochem Biophys Res Commun* 26: 162-7 (1967).
Bensinger et al., "Prolonged maintenance of 2,3-DPG in liquid blood storage: Use of an internal $CO_2$ trap to stabilize pH," *J. Lab. Clin. Med.*, 89(3):498-503 (1977).
Benson et al., "Accumulation of Pro-Cancer Cytokines in the Plasma Fraction of Stored Packed Red Cells," *J Gastrointest Surg.*, 16:460-468 (2012).
Bersin et al., "Importance of oxygen-haemoglobin binding to oxygen transport in congestive heart failure," *Br Heart J* 70: 443-7 (1993).
Beutler et al., "Storage of red cell concentrates in CPD-A2 for 42 and 49 days," *The Journal of Laboratory and Clinical Medicine*, 102(1):53-62 (1983).
Bordbar et al., "Identified metabolic signature for assessing red blood cell unit quality is associated with endothelial damage markers and clinical outcomes," *Transfusion* 56: 852-62 (2016).
Borenstein et al., "Microfabrication Technology for Vascularized Tissue Engineering," *Biomedical Microdevices*, 4(3):167-175 (2002).
Brody et al., "Deformation and Flow of Red Blood Cells in a Synthetic Lattice: Evidence for an Active Cytoskeleton," *Biophysical Journal*, 68:2224-2232 (1995).
Browne et al., "The molecular pathobiology of cell membrane iron: the sickle red cell as a model" *Free Radic Biol Med* 24: 1040-8 (1998).
Browne et al., "Removal of erythrocyte membrane iron in vivo ameliorates the pathobiology of murine thalassemia," *J Clin Invest* 100: 1459-64 (1997).
Bryant et al., "Pathogen Inactivation the Definitive Safeguard for the Blood Supply," *Arch Pathol Lab Med* 131:719-733 (2007).
Burns et al., "Anaerobic Storage Improves the Mechanical Properties of Stored Red Blood Cells," *Transfusion* 52: 83A (2012).
Burns et al., "Artificial microvascular network: a new tool for measuring rheologic properties of stored red blood cells," *Transfusion*, 52(5):1010-1023 (2012).
Burns et al., "Deterioration of red blood cell mechanical properties is reduced in anaerobic storage," *Blood Transfus* 14: 80-8 (2016).
Buskirk et al., "Accumulation of Biologic Response Modifiers During Red Blood Cell Cold Storage," *Transfusion*, 49(Suppl3): 102A-103A (2009).
Cabrales et al., "Microvascular pressure and functional capillary density in extreme hemodilution with low-and high-viscosity dextran and a low-viscosity Hb-based 02 carrier," *American Journal of Physiology-Heart and Circulatory Physiology* 287: H363-H73 (2004).
Cabrales et al., "Plasma viscosity regulates systemic and microvascular perfusion during acute extreme anemic conditions," *Am J. Physiol Heart Circ Physiol* 291: H2445-52 (2006).
Cannon et al., "Damage control resuscitation in patients with severe traumatic hemorrhage: A practice management guideline from the Eastern.Association for the Surgery of Trauma," *J Trauma Acute Care Surg* 82: 605-17 (2017).
Cap et al., "Whole Blood Transfusion," *Military Medicine* 183, 9/10:44 (2018).
Cardo et al., "Pathogen inactivation of *Leishmania donovani infantum* in plasma and platelet concentrates using riboflavin and ultraviolet light," *Vox Sanguinis* 90:85-91 (2006).
Cardo et al., "Pathogent inactivation of *Trypanosoma cruzi* in plasma and platet concentrates using riboflavin and ultraviolet light," *Transfusion and Apheresis Science* 37:131-137 (2007).
Carmen, "The Selection of Plastic Materials for Blood Bags," *Transfusion Medicine Reviews*, 7(1):1-10 (1993).
Carr et al., "Nonlinear Dynamics of Microvascular Blood Flow," *Annals of Biomedical Engineering*, 28:641-652 (2000).
Cell Deformability, RheoSCAN (RheoScan-AnD300/RheoScan-D300), obtained on Dec. 11, 2012, from: http://www.rheoscan.com/products/products/products-01.html.

(56) References Cited

OTHER PUBLICATIONS

Chanutin et al., "Effect of organic and inorganic phosphates on the oxygen equilibrium of human erythrocytes," *Arch Biochem Biophys* 121:96-102 (1967).
Chaplin et al., "The Proper Use of Previously Frozen Blood Cells for Transfusion," *Blood*, 59:1118-1120 (1982).
Chatpun et al., "Cardiac mechanoenergetic cost of elevated plasma viscosity after moderate hemodilution," *Biorheology* 47: 225-37 (2010).
Chatpun et al., "Cardiac systolic function recovery after hemorrhage determines survivability during shock," *J Trauma* 70: 787-93 (2011).
Chatpun et al., "Effects of plasma viscosity modulation on cardiac function during moderate hemodilution," *Asian J Transfus Sci* 4: 102-8 (2010).
Chilton et al., "Privacy Protection of Health Information: Patient Rights and Pediatrician Responsibilities," *Pediatrics*, 104(4):973-977 (1999).
Choi et al., "Influence of storage temperature on the responsiveness of human platelets to agonists," *Ann Clin Lab Sci* 33: 79-85 (2003).
Chouchani et al., "Ischaemic accumulation of succinate controls reperfusion injury through mitochondrial ROS," *Nature* 515: 431-5 (2014).
Coene, "Paired analysis of plasma proteins and coagulant capacity after treatment with three methods of pathogen reduction," *Transfusion* 54: 1321-31 (2014).
Cognasse et al., "The role of microparticles in inflammation and transfusion: A concise review," *Transfus. Apher. Sci.* 53(2):159-167 (2015).
Cokelet et al., "Fabrication of in Vitro Microvascular Blood Flow Systems by Photolithography," *Microvascular Research*, 46:394-400 (1993).
Corbin, "Pathogen Inactivation of Blood Components: Current Status and Introduction of an Approach Using Riboflavin as a Photosensitizer," *International Journal of Hematology* Supplement II 76:253-257 (2002).
Cotton et al., "A Randomized Controlled Pilot Trial of Modified Whole Blood Versus Component Therapy in Severely Injured Patients Requiring Large Volume Transfusions," *Annals of Surgery* 258(4) (2013).
Dale et al., "Human Vaccination with Escherichia coli J5 Mutant Induces Cross-Reactive Bactericidal Antibody against *Neisseria gonorrhoeae* Lipooligosaccharide," *The Journal of Infectious Diseases*, 166:316-325 (1992).
D'Alessandro et al., "Heterogeneity of blood processing and storage additives in different centers impacts stored red blood cell metabolism as much as storage time: lessons from REDS-11I-Omics," *Transfusion* 59: 89-100 (2019).
D'Alessandro et al., "Time-course investigation of SAGM-stored leukocyte-filtered red bood cell concentrates: from metabolism to proteomics," *Haematologica* 97: 107-15 (2012).
D'Alessandro et al., "Red blood cell metabolism under prolonged anaerobic storage," *Mol Biosyst* 9: 1196-209 (2013).
D'Alessandro et al., "Red blood cell metabolic responses to refrigerated storage, rejuvenation, and frozen storage," *Transfusion* 57: 1019-30 (2017).
D'Alessandro et al., "Metabolomics of AS-5 RBC supernatants following routine storage," *Vox Sang* (2014).
D'Alessandro et al., "An update on red blood cell storage lesions, as gleaned through biochemistry and omics technologies," *Transfusion* 55: 205-19 (2015).
D'Alessandro et al., "Red blood cell storage and clinical outcomes: new insights," *Blood Transfus* 15: 101-3 (2017).
D'Alessandro et al., "Plasma succinate is a predictor of mortality in critically injured patients," *Journal of Trauma and Acute Care Surgery* 83: 491-5 (2017).
D'Alessandro et al., "Plasma First Resuscitation Reduces Lactate Acidosis, Enhances Redox Homeostasis, Amino Acid and Purine Catabolismin a Rat Model of Profound Hemorrhagic Shock," *Shock* 46: 173-82 (2016).

D'Alessandro et al., "Anaerobic storage Condition enhances GSH Levels while Maintaining Pentose Phosphate Pathway Activity," *Transfusion* 56: 51A (2016).
D'Alessandro et al., "Red blood cell storage in additive solution-7 preserves energy and redox metabolism: a metabolomics approach," *Transfusion* 55: 2955-66 (2015).
D'Alessandro et al., "Routine storage of red blood cell (RBC) units in additive solution-3: a comprehensive investigation of the RBC metabolome," *Transfusion* 55: 1155-68 (2015).
D'Alessandro et al., "Omics markers of the red cell storage lesion and metabolic linkage," *Blood Transfus* 15: 137-44 (2017).
D'Alessandro et al., "AltitudeOmics: Red Blood Cell Metabolic Adaptation to High Altitude Hypoxia," *J Proteome Res* 15: 3883-95 (2016).
D'Alessandro et al., "Citrate metabolism in red blood cells stored in additive solution-3," *Transfusion* 57: 325-36 (2017).
D'Alessandro et al., "Metabolic effect of alkaline additives and guanosine/gluconate in storage solutions for red blood cells," *Transfusion* 58: 1992-2002 (2018).
D'Alessandro et al., "Effects of aged stored autologous red blood cells on human plasma metabolome," *Blood Adv* 3: 884-96 (2019).
D'Alessandro et al., "Hitchhiker's guide to the red cell storage galaxy: Omics technologies and the quality issue," *Transfus Apher Sci* 56: 248-53 (2017).
D'Amici, et al., "Red blood cell storage in SAGM and AS3: a comparison through the membrane two-dimensional electrophoresis proteome," *Blood Transfusion = Trasfusione del sangue* 10 Suppl 2: s46-54 (2012).
De Angelis et al., "Erythrocyte Shape Control in Stored Blood: The Effect of Additive Solutions on Shape Recovery," *Haematologica*, 73:7-12 (1988).
Deible et al., "Molecular barriers to biomaterial thrombosis by modification of surface proteins with polyethylene glycol," *Biomaterials*, 19:1885-1893 (1998).
De Korte et al., "Prolonged maintenance of 2,3-diphosphoglycerate acid and adenosine triphosphate in red blood cells during storage," *Transfusion*, 48:1081-1089 (2008).
De Venuto et al., "Rejuvenation of Human Red Blood Cells During Liquid Storage," *Transfusion*, 14(4):338-344 (1974).
Delgado et al., "Platelet Function in Stored Whole Blood Measured by a Shear- and Von Willebrand Factor-Dependent Methodology is Retained During Storage at 4° C. for up to 7 Days," *Transfusion* 51: 65A (2011).
Dennis et al., "Transfusion of 2,3 DPG-enriched red blood cells to improve cardiac function," *Ann Thorac Surg* 26: 17-6 (1978).
Dennis et al., "Improved myocardial performance following high 2-3 diphosphoglycerate red cell transfusions," *Surgery* 77: 741-7 (1975).
De Wolski et al., "Metabolic pathways that correlate with post-Transfusion circulation of stored murine red blood cells," *Haematologica* 101: 578-86 (2016).
Dumaswala et al., "Studies in Red Blood Cell Preservation: 9. The Role of Glutamine in Red Cell Preservation," *Vox Sang*, 67:255-259 (1994).
Dumaswala et al., "Glutamine- and Phosphate-Containing Hypotonic Storage Media Better Maintain Erythrocyte Membrane Physical Properties," *Blood*, 88(2):697-704 (1996).
Dumaswala et al., "Improved Red Blood Cell Preservation Correlates With Decreased Loss of Bands 3, 4.1, Acetylcholinestrase, and Lipids in Microvesicles," *Blood*, 87(4):1612-1616 (1996).
Dumont et al., "Anaerobic storage of red blood cells in a novel additive solution improves in vivo recovery," *Transfusion*, 49(3):458-464 (2009).
Dumont et al., "Performance of Anaerobic Stored Red Blood Cells Prepared Using A Prototype 02 & CO2 Depletion and Storage System," *Transfusion* 51s: SP89 (2011).
Dumont et al., "Randomized cross-over in vitro and in vivo evaluation of a prototype anaerobic conditioning and storage system vs. standard aerobic storage," *Vox Sang* 103: 123 (2012).
Dumont et al., "$CO_2$-dependent metabolic modulation in red cells stored under anaerobic conditions," *Transfusion* 56(2): 392-403 (2016)(epub 2015).

(56) References Cited

OTHER PUBLICATIONS

Durapore® Membrane Filters—Filter Discs and Membranes, retrieved on Aug. 26, 2014, from: www.emdmillipore.com/US/en/product/Durapore.
Effenhauser et al., "Integrated Capillary Electrophoresis on Flexible Silicone Microdevices: Analysis of DNA Restriction Fragments and Detection of Single DNA Molecules on Microchips," *Anal. Chem.*, 69:3451-3457 (1997).
Erickson et al., "Evaluation of in vitro Quality of Stored RBC after Treatment with S303 Pathogen Inactivation at Varying Hematocrits," *Transfusion DUP—General Collection* 48(2) Supplement (2008).
European Search Report completed on Feb. 11, 2005, in European Patent Application No. 02 78 2307.9.
European Search Report Jun. 18, 2019, in European Patent Application No. 19163305.6.
Extended European Search Report, dated Aug. 29, 2014 for European Patent Application No. 10823965.8.
Extended European Search Report dated Oct. 30, 2014 in European Patent Application No. 11838889.1.
Extended European Search Report dated Oct. 24, 2014 in European Patent Application No. 12807324.4.
Extended European Search Report dated Mar. 5, 2015, in European Patent Application No. 12821624.9.
Extended European Search Report dated Jun. 15, 2015, in European Patent Application No. 11820660.6.
Extended European Search Report dated Oct. 9, 2018, in European Patent Application No. 16784043.8.
Extended European Search Report dated Apr. 16, 2019, in European Patent Application No. 16845192.0.
Extended European Search Report dated Jun. 5, 2019, in European Patent Application No. 19158815.1.
Ezuki et al., "Survival and recoery of apheresis platelets stored in a polyolefin container with high oxygen permeability," *Vox Sanguinis* 94:292-298 (2008).
Fahraeus et al., "The Viscosity of the Blood in Narrow Capillary Tubes," *Am. J. Physiol.*, 96(3):562-568 (1931).
Fage et al., "On transition from laminar to turbulent flow in the boundary layer," The gamma-ray transition of radio-bromine, *Proceedings of the Royal Society*, 178(973):205-227 (1940).
Fang et al., "Inhibition of Lipopolysaccharide-Associated Endotoxin Activities In Vitro and In Vivo by the Human Anti-Lipid A Monoclonal Antibody SdJ5-1.17.15," *Infection and Immunity*, 61(9):3873-3878 (1993).
Farber et al., "Effect of decreased 02 affinity of hemoglobin on work performance during exercise in healthy humans," *J Lab Clin Med* 104: 166-75 (1984).
Fast et al., "Inactivation of Human White Blood Cells in Red Blood Cell Products Using the MIRASOL® System for Whole Blood," *Blood Abstract* #2897 110(11)(pt. 1) (2007).
Fatouros et al., "Recombinant factor VII SQ—influence of oxygen, metal ions, pH and ionic strength on its stability in aqueous solution," *International Journal of Pharmaceutics*, 155(1):121-131 (1997).
Feys, "Oxygen removal during pathogen inactivation with riboflavin and UV light preserves protein function in plasma for Transfusion," *Vox Sang* 106: 307-15 (2013).
Frame et al., "A System for Culture of Endothelial Cells in 20-50-μm Branching Tubes," *Microcirculation*, 2(4):377-385 (1995).
"Friction Factor for Flow in Coils and Curved Pipe," Neutrium Available on the world wide web at neutrium.net/fluid_flow/friction-factor-for-flow-in-coils-and-curved-pipe/ (2017).
Friesenecker et al., "Arteriolar vasoconstrictive response: comparing the effects of arginine vasopressin and norepinephrine," *Crit Care* 10: R75 (2006).
Fung et al., "High-Resolution Data on the Geometry of Red Blood Cells", *Biorheology*, 18:369-385 (1981).
Gañán-Calvo et al., "Current and Droplet Size in the Electrospraying of Liquids. Scaling Laws," *J. Aerosol Sci.*, 28(2):249-275 (1997).

Gardner, "Problems of Multiple Transfusions," *Official Journal of the California Medical Associate*, 83(2):93-97 (1958).
Gehrke et al., "Metabolomics evaluation of early-storage red blood cell rejuvenation at 4 degrees C and 37 degrees C," *Transfusion* 58: 1980-91 (2018).
Gevi et al., "Alterations of red blood cell metabolome during cold liquid storage of erythrocyte concentrates in CPD-SAGM," *J Proteomics* 76 Spec No. 168-180 (2012).
Gifford et al., "Parallel Microchannel-Based Measurements of Individual Erythrocyte Areas and Volumes," *Biophysical Journal*, 84:623-633 (2003).
Gifford et al., "A detailed study of time-dependent changes in human red blood cells: from reticulocyte maturation to erythrocyte senescence," *British Journal of Haematology*, 135:395-404 (2006).
Golan et al., "Transfusion of fresh whole blood stored (4 degrees C) for short period fails to improve platelet aggregation on extracellular matrix and clinical hemostasis after cardiopulmonary bypass," *J Thorac Cardiovasc Surg* 99: 354-60 (1990).
Goodrich, "The Use of Riboflavin for the Inactivation of Pathogens in Blood Products," *Vox Sanguinis* Suppl. 2 78:211-215 (2000).
Green et al., "10. Liposomal Vaccines," Immunobiology of Proteins and Peptides VII, Plenum Press, New York, pp. 83-92 (1995).
Greenwalt et al., "Studies in Red Blood Cell Preservation. 7. In vivo and in Vitro Studies with a Modified Phosphate-Ammonium Additive Solution," *Vox Sang*, 65:87-94 (1993).
Greenwalt et al., "Studies in Red Blood Cell Preservation. 8. Liquid Storage of Red Cells in Glycerol-Containing Additive Solution," *Vox. Sang*, 67:139-143 (1994).
Greenwalt et al., "Studies in red blood cell preservation. 10. $^{51}$Cr Recovery of Red Cells after Liquid Storage in a Glycerol-Containing Additive Solution," *Vox Sang*, 70:6-10 (1996).
Greenwalt et al., "The effect of hypotonicity, glutamine, and glycine on red cell preservation," *Transfusion*, 37:269-276 (1997).
Griffith, "Temporal chaos in the microcirculation," *Cardiovascular Research*, 31:342-358 (1996).
Grigioni et al., "A discussion on the threshold limited for nemo lysis related to Reynolds shear stress," *J. Biomech.*, 32:1107-1112 (1999).
Gulliksson et al., "Storage of whole blood overnight in different blood bags preceding preparation of blood components: in vitro effects on red blood cells," *Blood Transfus* 7:210-215 (2009).
Haddaway et al., "Hemostatic properties of cold-stored whole blood leukoreduced using a platelet-sparing versus a non-platelet-sparing filter," *Transfusion* (2019).
Hamasaki et al., "Acid-citrate-dextrose-phosphoenolpyruvate medium as a rejuvenant for blood storage," *Transfusion*, 23(1):1-7 (1983).
Heaton et al., "Use of Adsol preservation solution for prolonged storage of low viscosity AS-1 red blood cells," *Br J. Haematol*, 57(3):467-478 (1984).
Hebbel, et al., Oxidation-induced changes in microrheologic properties of the red blood cell membrane, *Blood* 1990;76: 1015-20.
Hebbel, "Auto-oxidation and a membrane-associated 'Fenton reagent': a possible explanation for development of membrane lesions in sickle erythrocytes," *Clin Haematol* 14: 129-40 (1985).
Henschler et al., "Development of the S-303 Pathogen Inactivation Technology for Red Blood Cell Concentrates," *Transfusion Medicine and Hemotherapy* 38(1):33-42 (2011).
Hershko, "Mechanism of iron toxicity and its possible role in red cell membrane damage," *Semin Hematol* 26: 277-85 (1989).
Hess, "Extended Liquid Storage of Red Blood Cells," Blood Donors and the Supply of Blood and Blood Products, National Academy Press, Washington, D.C., pp. 99-102 (1996).
Hess et al., "Successful storage of RBCs for 9 weeks in a new additive solution," *Transfusion*, 40:1007-1011 (2000).
Hess, "Storage of red blood cells under anaerobic conditions," *Vox Sanguinis*, 93:183 (2007).
Hess et al., "Alkaline CPD and the preservation of RBC 2,3-DPG," *Transfusion*, 42:747-752 (2002).
Hess et al., "Storage of Red Blood Cells: New Approaches," *Transfusion Medicine Reviews*, 16(4):283-295 (2002).
Hess et al., "Advances in military, field, and austere Transfusion medicine in the last decade," *Transfus Apher Sci* 49: 380-6 (2013).
Hodgson et al., "Prophylactic use of human endotoxin-core hyperimmune gammaglobulin to prevent endotoxaemia in colostrum-

(56) References Cited

OTHER PUBLICATIONS deprived, gnotobiotic lambs challenged orally with *Escherichia coli*," *FEMS Immunology and Medical Microbiology*, 11:171-180 (1995).
Högman et al., "Cell Shape and Total Adenylate Concentration as Important Factors for Posttransfusion Survival of Erythrocytes," *Biomed. Biochim. Acta*, 42:S327-S331 (1983).
Högman et al., " Effects of Oxygen on Red Cells during Liquid Storage at +4° C.," *Vox Sang.*, 51:27-34 (1986).
Högman et al., "Effects of oxygen and mixing on red cells stored in plastic bags at +4° C.," *Biomed. Biochim. Acta.*, 46:S290-S294 (1987).
Högman et al., "Shall Red Cell Units Stand Upright, Lie Flat or be Mixed During Storage? In Vitro Studies of Red Cells Collected in 0.5 CPD and Stored in RAS2 (Erythrosol®)," *Transfus. Sci.*, 16(2):193-199 (1995).
Högman, "Preparation and Preservation of Red Cells," *Vox Sanguinis* 74(Suppl. 2):177-187 (1998).
Holme et al., "Current Issues Related to the Quality of Stored RBCs," *Transfusion and Apheresis Science*, 33(1):55-61 (2005).
Hornsey et al., "Cold storage of pooled, buffy-coat-derived, leucoreduced platelets in plasma," *Vox Sang* 95 26-32 (2008).
Huang et al., "Continuous Particle Separation Through Deterministic Lateral Displacement," *Science*, 304:987-990 (2004).
International Committee for Standardization in Hematology, "Recommended Methods for Radioisotope Red Cell Survival Studies," *Blood* 38(3):378-386 (1971).
International Preliminary Report on Patentability dated Feb. 18, 2011 (completed on Feb. 8, 2012), in International Patent Application No. PCT/US2010/52084.
International Preliminary Report on Patentability dated May 24, 2012 (completed on May 21, 2012), in International Patent Application No. PCT/US2010/52376.
International Search report Completed on Feb. 8, 2011, in International Patent Application No. PCT/US10/52084.
International Preliminary Report on Patentability completed on Oct. 18, 2011, in International Patent Application No. PCT/US2010/031055.
International Search Report completed on Jul. 8, 1996, in International Patent Application No. PCT/US96/09005.
International Search Report completed on Nov. 10, 2003, in International Patent Application No. PCT/US02/36735.
International Search Report completed on May 20, 2010, in International Patent Application No. PCT/US2010/31055.
International Search Report and Written Opinion dated Dec. 6, 2010 for corresponding International Patent Application No. PCT/US2010/052376.
International Search Report dated Apr. 27, 2011(completed on Apr. 26, 2011), in International Patent Application No. PCT/US2010/044045.
International Search Report completed on Dec. 21, 2011, in International Patent Application No. PCT/US11/49168.
International Search Report completed on Feb. 12, 2012, in International Patent Application No. PCT/US11/59372.
International Search Report completed on Jun. 18, 2012, in International Patent Application No. PCT/US12/30930.
International Search Report completed on Sep. 24, 2012, in International Patent Application No. PCT/US12/50380.
International Search Report and Written Opinion issued in International Application PCT/US2014/019537 dated Jul. 10, 2014.
International Search Report completed on Nov. 9, 2012 issued in International Patent Application No. PCT/US12/045426 (mailed Nov. 26, 2012).
International Search Report for PCT/US2016/021794 dated Jul. 18, 2016.
International Search Report for PCT/US2016/033151 dated Oct. 13, 2016.
International Search Report for PCT/US2016/051115 dated Nov. 21, 2016.
International Search Report for PCT/US2017/034410 dated Dec. 22, 2017.
Irsch et al., "Pathogen inactivation of platelet and plasma blood components for transfusion using the Intercept Blood SystemTM," *Transfusion Medicine and Hemotherapy*, 38:19-31 (2011).
Jagannathan et al., "Oxidative stress under ambient and physiological oxygen tension in tissue culture," *Curr Pharmacol Rep* 2: 64-72 (2016).
Jain et al., "Determinants of Leukocyte Margination in Rectangular Microchannels," *PLoS ONE*, 4(9):1-8 (2009).
Janetzko et al., "Pathogen reduction technology (Mirasol®) treated singledonor platelets resuspended in a mixture of autologous plasma and PAS," *Vox Sanguinis* 97:234-239 (2009).
Jarman et al., "Rural risk: Geographic disparities in trauma mortality," *Surgery* 160: 1551-9 (2016).
Jarolim et al., "Effect of hemoglobin oxidation products on the stability of red cell membrane skeletons and the associations of skeletal proteins: correlation with a release of them in," *Blood* 76: 2125-31 (1990).
Jarus et al., "Barrier Properties of polypropylene/polyamide blends produced by microlayer coextrusion," *Polymer* 43:2401-2408 (2002).
Jayasinghe et al., "Controlled deposition of nanoparticle clusters by electrohydrodynamic atomization," *Nanotechnology*, 15:1519-1523 (2004).
Jenkins et al., "Trauma hemostasis and oxygenation research position paper on remote damage control resuscitation: definitions, current practice, and knowledge gaps," *Shock* 41 Suppl 1: 3-12 (2014).
Jesch et al., "Oxygen dissociation after Transfusion of blood stored in ACD or CPD solution," *J Thorac Cardiovasc Surg* 70: 35-9 (1975).
Jiang et al., "Microfluidic synthesis of monodisperse PDMS microbeads as discrete oxygen sensors," *Soft Matter*, 8:923-926 (2011).
Jo et al., "Surface modification using silanated poly(ethylene glycol)s," *Biomaterials*, 21:605-616 (2000).
Jobes et al., "Toward a definition of "fresh" whole blood: an in vitro characterization of coagulation properties in refrigerated whole blood for Transfusion," *Transfusion* 51: 43-51 (2011).
Johnson et al., "Regulation of blood flow in single capillaries," *American Journal of Physiology*, 212:1405-1415 (1967).
Jy et al., "Release of Microparticles During Blood Storage Is Influenced by Residual Platelets, Leukocytes and Oxygen Levels," *Blood* 120: 3435 (2012).
Kaihara et al., "Silicon Micromachining to Tissue Engineer Branched Vascular Channels for Liver Fabrication," *Tissue Engineering*, 6(2):105-117 (2000).
Kaiser-Guignard et al., "The clinical and biological impact of new pathogen inactivation technologies on platelet concentrates," *Blood Reviews* 28:235-241 (2014).
Kakaiya et al., "Platelet preservation in large containers," *Vox Sanguinis*, 46(2):111-118 (1984).
Kerger et al., "Systemic and subcutaneous microvascular pO2 dissociation during 4-h hemorrhagic shock in conscious hamsters," *Am J. Physiol* 270: H827-H36 (1996).
Khorana et al., " Blood Transfusions, thrombosis, and mortality in hospitalized patients with cancer," *Arch Intern Med* 168: 2377-81 (2008).
Kiani et al., "Fluctuations in microvascular blood flow parameters caused by hemodynamic mechanisms," *American Journal of Physiology*, 266(5):H1822-H1828 (1994).
Kikuchi et al., "Modified Cell-Flow Microchannels in a Single-Crystal Silicon Substrate and Flow Behavior of Blood Cells," *Microvascular Research*, 47:126-139 (1994).
Kilkson et al., "Platelet metabolism during storage of platelet concentrates at 22° C.," *Blood* 64(2):406-414 (1984).
Koch et al., "Peripheral blood leukocyte NO production and oxidative stress in multiple sclerosis," *Multiple Sclerosis*, 14:159-165 (2008).
Koch et al., "Duration of Red-Cell Storage and Complications After Cardiac Surgery," *The New England Journal of Medicine*, 358:1229-1239 (2008).
Kohli et al., "Packed red cells versus whole blood transfusion for severe paediatric anaemia, pregnancy-related anaemia and obstetric

(56) References Cited

OTHER PUBLICATIONS bleeding: an analysis of clinical proactice buidelines from sub-Saharan Africa and evidence underpinning recommendments," *Tropical Medicine and International Health* 24(1):11-22 (2019).

Korsten et al., "Determination of %502 in More Than 1300 Fresh Erythrocyte Concentrates by Resonance Raman Spectroscopy," *Transfusion* 58: 215A (2018).

Kotwal et al., "The Effect of a Golden Hour Policy on the Morbidity and Mortality of Combat Casualties," *JAMA Surg* 151: 15-24 (2016).

Kreuger et al., "A clinical evaluation of citrate-phosphate-dextrose-adenine blood," *Vox Sang* 29: 81-9 (1975).

Krogh, "Studies on the physiology of capillaries. II. The reactions to local stimuli of the blood-vessels in the skin and web of the frog," *The Journal of Physiology*, 55:412-422 (1921).

Kuraoka, et al., "Ship-in-a-bottle synthesis of a cobalt phthalocyanine/porous glass composite membrane for oxygen separation," *Journal of Membrane Science*, 286(1-2):12-14 (2006).

Kwan et al., "Microfluidic analysis of cellular deformability of normal and oxidatively damaged redd blood cells," *Am J Hematol* 88: 682-9 (2013).

Kynar Flex Product Catalog, downloaded May 20, 2015 from Kynar.com.

Liu et al., "Beneficial Role of Erythrocyte Adenosine A2B Receptor-Mediated AMP-Activated Protein Kinase Activation in High-Altitude Hypoxia," *Circulation* 134: 405-21 (2016).

Lowndes, "Blood Interference in fluorescence spectrum: Experiment, analysis and comparison with intraoperative measurements on brain tumor," *Bachelor Thesis*, Linköping University, pp. 1-42 (2010).

Lozono et al., "Pathogen inactivation: coming of age," *Curr Opin Hematol* 20(6):540-545 (2013).

Lugowski et al., "Anti-endotoxin antibodies directed against *Escherichia coli* R-oligosaccharide core-tetanus toxoid conjugate bind to smooth, live bacteria and smooth lipopolysaccharides and attenuate their tumor necrosis factor stimulating activity," *FEMS Immunology and Medical Microbiology*, 16:31-38 (1996).

Lundblad, "Factor VIII—Reducing agents, copper ions, and stability," http://lundbladbiotech.com.

Manno et al., "Comparison of the hemostatic effects of fresh whole blood, stored whole blood, and components after open heart surgery in children," *Blood* 77: 930-6 (1991).

Mazor et al., "Prolonged Storage of Red Cells: The Effect of pH, Adenine Phosphate," *Vox Sanguinis*, 66:264-269 (1994).

McDonald et al., "Poly(dimethylsiloxane) as a Material for Fabricating Microfluidic Devices," *Accounts of Chemical Research*, 35(7):491-499 (2002).

Meryman et al., "Prolonged storage of red cells at 4° C.," *Transfusion*, 26(6):500-505 (1986).

Meryman et al., "Extending the storage of red cells at 4° C.," *Transfus. Sci.*, 15(2):105-115 (1994).

Miller, "New evidence in trauma resuscitation-is 1: 1: 1 the answer?" *Perioperative medicine* 2: 13 (2013).

Moll et al., "Dean vortices applied to membrane process. Part II: Numerical approach," *Journal of Membrane Science*, 288:321-335 (2007).

Mollison, "The Introduction of Citrate as an Anticoagulant for Transfusion and of Glucose as a Red Cell Preservative," *British Journal of Haematology* 108:1318 (2000).

Moroff et al., "Factors Influencing Changes in pH during Storage of Platelet Concentrates at 20-24° C.," *Vox Sanguinis*, 42(1):33-45 (1982).

Moroff et al., "Proposed standardization of methods for determining the 24-hour survival of stored red cells," *Transfusion*, 24:109-114 (1984).

Moroff et al., "Concepts about current conditions for the preparation and storage of platelets," *Transfus Med Rev* V(1):48-59 (1991).

Murphy et al., "Platelet storage at 22° C.: role of gas transport across plastic containers in maintenance of viability," *Blood* 46(2):209-218 (1975).

Murphy et al., "Increased Mortality, Postoperative Morbidity, and Cost After Red Blood Cell Transfusion in Patients Having Cardiac Surgery," *Circulation*, 116:2544-2552 (2007).

Musante et al., "Active Focal Segmental Glomerulosclerosis is Associated with Massive Oxidation of Plasma Albumin," *Journal of the American Society of Nephrology*, 18(3):799-810 (2007).

Mussano et al., "Cytokine, chemokine and growth factor profile of Platelet Rich Plasma," *Universita Degli Studi Di Tornio* 2016.

Nair et al., "Cold-Stored Platelets in PAS Exhibit Superior Hemostatic Potential" *Blood* 126: 772 (2015) Abstract.

Nemkov et al., "Metabolomics in Transfusion medicine," *Transfusion* 56: 980-93 (2015).

Nemkov et al., "Hypoxia modulates the purine salvage pathway and decreases red blood cell and supernatant levels of hypoxanthine during refrigerated storage," *Haematologica* 103: 361-72 (2018).

Nemkov et al., "Metabolism of Citrate and Other Carboxylic Acids in Erythrocytes As a Function of Oxygen Saturation and Refrigerated Storage," *Front Med (Lausanne)* 4: 175 (2017).

Nessen et al., "Fresh whole blood use by forward surgical teams in Afghanistan is associated with improved survival compared to component therapy without platelets," *Transfusion* 53:107S-113S (2013).

Ng et al., "Components for integrated poly(dimethylsiloxane) microfluidic systems," *Electrophoresis*, 23:3461-3473 (2002).

Nilsson et al., "Association between venous thromboembolism and perioperative allogeneic Transfusion," *Arch Surg* 142: 126-32; discussion 33 (2007).

Ohkuma et al., "The preservative-exchange method using a sextuple-bag system for a 10-week storage period of red blood cells," *Transfusion Medicine*, 1:257-262 (1991).

Paglia et al., "Biomarkers describing the metabolic age of red blood cells during cold storage," *Blood* 128: e43-50 (2016).

Paillous et al. "Mechanisms of photosensitized DNA cleavage," *J. Photochem. Photobiol. B: Biol.* 20:203-209 (1993).

Pallotta et al., "Storing red blood cells with vitamin C and N-acetylcysteine prevents oxidative stress-related lesions: a metabolomics overview," *Blood Transfus* 12: 376-87 (2014).

Pallotta et al., "Supplementation of anti-oxidants in leucofiltered erythrocyte concentrates: assessment of morphological changes through scanning electron microscopy," *Blood Transfus* 12: 421-4 (2014).

Parkkinen et al., "Plasma ascorbate protects coagulation factors against photooxidation," *Thromb Haemost* 75(2):292-297 (1996).

Peirce et al., "The Membrane Lung: Studies with a New High Permeability Co-Polymer Membrane," *Trans. Amer. Soc. Artif. Int. Organs* vol. XIV:220-226 (1968).

Pelletier et al., "Pathogen inactivation techniques," *Best Practice & Research Clinical Haematology* 19(1):205-242 (2006).

Picker et al., "Current methods for the reduction of blood-borne pathogens: a comprehensive literature review," *Blood Transfusion* 11:343-348 (2013).

Pidcoke et al., "Tenyear analysis of Transfusion in Operation Iraqi Freedom and Operation Enduring Freedom: increased plasma and platelet use correlates with improved survival," *Journal of Trauma and Acute Care Surgery*;73: S445-S52 (2012).

Pidcoke et al., "Primary hemostatic capacity of whole blood: a comprehensive analysis of pathogen reduction and refrigeration effects over time," *Transfusion* 53:137S-149S (2013).

Poncelet et al., "Tips and tricks for flow cytometry-based analysis and counting of microparticles," *Transfus. Apher. Sci.* 53(2):110-126 (2015).

Poxton, "Antibodies to lipopolysaccharide," *Journal of Immunological Methods*, 186:1-15 (1995).

Prefiltration before membrane filtration, hydrophobic, 25 μm 142 mm, retrieved on Aug. 26, 2014, from: www.emdmillipore.com/US/en/product/Prefiltration-before-membrane-filtration.

Pries et al., "Biophysical aspects of blood flow in the microvasculature," *Cardiovascular Research*, 32:654-667 (1996).

Prudent, et al., "Oxygen in Red Blood Cell Concentrates Influence of Donor's Characteristics, Location and Blood Processing," *Vox Sang* 113: 116 (2018).

Przepiorka et al. "Use of Irradiated Blood components: Practice Parameter," *Am J Clin Pathol* 106(1):6-11 (1996).

(56) References Cited

OTHER PUBLICATIONS

Ramstack et al., "Shear-induced activation of platelets," *J. Biomech.*, 12:113-125 (1979).
Reisz et al., "Red blood cells in hemorrhagic shock: a critical role for glutaminolysis in fueling alanine transamination in rats," *Blood Advances* 1:1296-305 (2017).
Reisz et al., "Methylation of protein aspartates and deamidated asparagines as a function of blood bank storage and oxidative stress in human red blood cells," *Transfusion* 58: 2978-91 (2018).
Reisz et al., "Metabolic Linkage and Correlations to Storage Capacity in Erythrocytes from Glucose 6-Phosphate Dehydrogenase-Deficient Donors," *Front Med (Lausanne)* 4: 248 (2017).
Reisz et al., "Oxidative modifications of glyceraldehyde 3-phosphate dehydrogenase regulate metabolic reprogramming of stored red blood cells," *Blood* 128: e32-42 (2016).
Reynolds et al., "S-nitrosohemoglobin deficiency: A mechanism for loss of physiological activity in banked blood," *Proceedings of the National Academy of Sciences*, 104(43):17058-17062 (2007).
Risbano et al., "Effects of Aged Stored Autologous Red Blood Cells on Human Endothelial Function," *Am J Respir Crit Care Med* 192: 1223-33 (2015).
Rock et al., "Nutricel as an additive solution for neonatal transfusion," *Transfusion Science*, 20:29-36 (1999).
Rolfsson et al., "Metabolomics comparison of red cells stored in four additive solutions reveals differences in citrate anticoagulant permeability and metabolism," *Vox Sang* (2017).
Sambuceti et al., "Why should we study the coronary microcirculation?," *Am J Physiol Heart Circ Physiol*, 279:H2581-H2584 (2000).
Schubert et al., "Whole blood treated with riboflavin and ultraviolet light: Quality assessment of all blood components produced by the buffy coat method," *Transfusion* 55(4):815-823 (2014).
Scott et al., "Effect of excess alpha-hemoglobin chains on cellular and membrane oxidation in model beta-thalassemic erythrocytes," *J Clin Invest* 91: 1706-12 (1993).
Seghatchian et al., "Pathogen-reduction systems for blood components: The current position and future trends," *Transfusion and Apheresis Science* 35:189-196 (2006).
Seok et al., "Genomic responses in mouse models poorly mimic human inflammatory diseases," *Proceedings of the National Academy of Sciences* 110: 3507-12 (2013).
Sivertsen et al., "Preparation of leukoreduced whole blood for Transfusion in austere environments; effects of forced filtration, storage agitation, and high temperatures on hemostatic function," *J Trauma Acute Care Surg* 84: S93-S103 (2018).
Shalev et al., "Extremely high avidity association of Fe(III) with the sickle red cell membrane," *Blood* 88: 349-52 (1996).
Shapiro, "To filter blood or universal leukoreduction: what is the answer?," *Critical Care* 8(Suppl 2): S27-draftS30 (2004).
Sheffield et al., "Changes in coagulation factor activity and content of di(2-ethylhexyl) phthate in frozen plasma units during refrigerated storage for up to 5 days after thawing," *Transfusion*, 52:494-502 (2012).
Shevkoplyas et al., "Direct measurement of the impact of impaired erythrocyte deformability on microvascular network perfusion in a microfluidic device," *Lab Chip*, 6:914-920 (2006).
Shimizu et al., "Multicenter Clinical Evaluation of Red Cell Concentrates Stored up to 6 Weeks in MAP, a new additive solution," *Japanese Journal of Clinical Hematology*, 33(2):148-156 (1992).
Skalak et al., "Deformation of Red Blood Cell in Capillaries," *Science*, 164(3880):717-719 (1969).
Snyder et al., "In vitro and in vivo evaluation of a whole blood platelet-sparing leukoreduction filtration system," *Transfusion* 50: 2145-51 (2010).
Sohmer et al., "Phosphoenolypyruvate (PEP) Effects on Fresh and Stored Red Blood Cells," *Proceedings of the Society for Experimental Biology and Medicine*, 171:24-33 (1982).
Spinella et al., "Prehospital hemostatic resuscitation to achieve zero preventable deaths after traumatic injury," *Curr Opin Hematol* (2017).

Spinella et al., "Whole blood: back to the future," *Curr Opin Hematol* 23: 536-42 (2016).
Spinella et al., "Whole blood for hemostatic resuscitation of major bleeding," *Transfusion* 56:S190-S202 (2016).
Steurer et al., "Trauma and Massive Blood Transfusions," *Curr. Anesthesiol. Rep* 4:200-208 (2014).
Strandenes et al., "Emergency Whole-Blood Use in the Field: a Simplified Protocol for Collection and Transfusion," *SHOCK* 41(Suppl 1):76-83 (2014).
Strandenes et al., "Low Titer Group O Whole Blood in Emergency Situations," *SCHOCK* 41(Suppl 1): 70-75 (2014).
Su et al., "Impermeable barrier films and protective coatings based on reduced graphene oxide," *Nature Communications* 5 Article No. 4843 (2014).
Sun et al., "Purinergic control of red blood cell metabolism: novel strategies to improve red cell storage quality," *Blood Transfus* 15: 535-42 (2017).
Sun, et al., "Sphingosine-1-phosphate promotes erythrocyte glycolysis and oxygen release for adaptation to high-altitude hypoxia," *Nat Commun* 7: 12086 (2016).
Supplementary European Search Report dated Jan. 20, 2015 in European Patent Application No. 12822378.2.
Sutera et al., "Deformation and Fragmentation of Human Red Blood Cells in Turbulent Shear Flow," *Biophys. J.*, 15:1-10 (1975).
Sutton et al., "A Novel Instrument for Studying the Flow Behaviour of Erythrocytes through Microchannels Simulating Human Blood Capillaries," *Microvascular Research*, 53:272-281 (1997).
Szymanski et al., "Effect of rejuvenation and frozen storage on 42-day-old AS-1 RBCs," *Transfusion*, 41:550-555 (2001).
Tannahill et al., "Succinate is an inflammatory signal that induces IL-1beta through HIF-1alpha" *Nature* 496: 238-42 (2013).
Teisseire et al., "Induced low P50 in anesthetized rats: blood gas, circulatory and metabolic adjustments," *Respir Physiol* 58: 335-44 (1984).
Tinmouth et al., "The Clinical Consequences of the Red Cell Storage Lesion," *Transfusion Medicine Reviews*, 15(2):91-107 (2001).
Tolinski, "Getting the Most out of Polypropylene, Polyethylene and TPO," *Additives for Polyolefins*, Second Edition 2015.
Tracey et al., "A Silicon Micromachined Device for Use in Blood Cell Deformability Studies," *IEEE Transactions on Biomedical Engineering*, 42(8):751-761 (1995).
"Transition and Turbulence," https://www.princeton.edu/~asmits/Bicycle_web/transition.html . Adapted from the Engine and the Atmosphere: An Introduction to Engineering by Z. Warhaft, Cambridge University Press, (1997).
Tsai et al., "Microvascular perfusion upon exchange Transfusion with stored red blood cells in normovolemic anemic conditions," *Transfusion* 44: 1626-34 (2004).
Tsantes et al., "Redox imbalance, macrocytosis, and RBC homeostasis," *Antioxid Redox Signal* 8: 1205-16 (2006).
Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).
Valeri et al., "Improved oxygen delivery to the myocardium during hypothermia by perfusion with 2,3 DPG-enriched red blood cells," *Am Thorac Surg* 30: 527-35 (1980).
Valeri, "Circulation and hemostatic effectiveness of platelets stored at 4 C or 22 C: studies in aspirintreated normal volunteers," *Transfusion* 16: 20-3 (1976).
Valeri, "Hemostatic effectiveness of liquid-preserved and previously frozen human platelets," *N Engl J Med* 290: 353-8 (1974).
Valeri et al., "The survival, function, and hemolysis of human RBCs stored at 4° C. in additive solution (AS-1, AS-3, or AS-5) for 42 days and then biochemically modified, frozen, thawed, washed, and stored at 4° C. in sodium chloride and glucose solution for 24 hours," *Transfusion*, 40:1341-1345 (2000).
Van Buskirk et al., "Comparison of Cytokine, Cell-free Hemoglobin, and Isoprostane Accumulations in Packed Red Blood Cells During Novel Anaerobic and Conventional Cold Storage," *Transfusion* 54S: SP53 (2014).

(56) References Cited

OTHER PUBLICATIONS

Van Buskirk et al., "Comparison of microparticles production in packed red blood cells stored under anaerobic and conventional cold storage condition," *Vox Sang* 105 (S1): 150 (2007).
Van Buskirk et al., "Evaluation of Select Red Blood Cell Biochemical and Coagulation Properties in Whole Blood Stored Using a Novel Anaerobic Storage Platform," *Transfusion* 56: 54A (2016).
Van Slyke, "An Apparatus for Determination of the Gases in Blood and Other Solutions," *Chemistry* 7:229-231 (1921).
Voigt et al., "Effects of a restrictive Blood Transfusion protocol on acute pediatric burn care: Transfusion threshold in pediatric burns," *J Trauma Acute Care Surg* 85: 1048-54 (2018).
Vrielink et al., "Transfusion-transmissible infections," *Current Opinion in Hematology* 5:396-405 (1998).
Wallvik et al., "Platelet Concentrates Stored at 22° C. Need Oxygen the Significance of Plastics in Platelet Preservation," *Vox Sanguinis*, 45(4):303-311 (1983).
Wallvik et al., "The platelet storage capability of different plastic containers," *Vox Sanguinis*, 58(1):40-44 (1990).
Wang et al., "Fabrication of PLGA microvessel scaffolds with circular microchannels using soft lithography," *Journal of Micromechanics and Microengineering*, 17(10):2000-2005 (2007).
Weinberg et al., "Transfusions in the Less Severely Injured: Does Age of Transfused Blood Affect Outcomes?," *The Journal of TRAUMA*, 65(4):794-798 (2008).
Wilding et al., "Manipulation and Flow of Biological Fuids in Straight Channels Micromachined in Silicon," *Clinical Chemistry*, 40(1):43-47 (1994).
Williams, "Blood Transfusion on Cruise Ships; A 36 Month Review of Preliminary Data," *THOR Trauma Hemostasis & Oxygenation Research Network, RDCR Symposium, Bergen* (2013).
Williams et al., "Transfusion of Anaerobically Stored Red Blood Cells Improves Recovery in Experimental Rat Hemorrhagic Shock Model," *Transfusion* 57: 33A (2017).
Williams et al., "Transfusion of Anaerobically Stored Red Blood Cells Improves Recovery in Experimental Rat Hemorrhagic Shock Model," *Shock Abstract* (2019).
Wolfe et al., "Molecular defect in the membrane skeleton of blood bank-stored red cells. Abnormal spectrin-protein 4.1-actin complex formation," *J Clin Invest* 78: 1681-6 (1986).
Wolfe, "Oxidative injuries to the red cell membrane during conventional blood preservation," *Semin Hematol* 26: 307-12 (1989).
Wood et al., "The Viability of Human Blood Stored in Phosphate Adenine Media," *Transfusion* 7, 401-408 (1967).
Woodson, "Functional consequences of altered blood oxygen affinity," *Acta Biol Med Ger* 40: 733-6 (1981).
Wu et al., "Polymer microchips bonded by $O_2$-plasma activation," *Electrophoresis*, 23:782-790 (2002).
Yalcin et al., "Increased hemoglobin 02 affinity protects during acute hypoxia," *Am J. Physiol Heart Circ Physiol* 303: H271-81 (2012).
Yazer et al., "Coagulation factor levels in plasma frozen within 24 hours of phlebotomy over 5 days of storage at 1 to 6° C.," *Transfusion*, 48:2525-2530 (2008).
Yhap et al., "Decreased oxygen uptake with stored blood in the isolated hindlimb" *J Appl Physiol* 38: 882-885 (1975).
Yoshida et al., "Extended storage of red blood cells under anaerobic conditions," *Vox Sanguinis*, 92:22-31 (2007).
Yoshida et al., "Storage of red blood cells under anaerobic conditions: reply," *Vox Sanguinis*, 93:184 (2007).
Yoshida et al., "The effects of additive solution pH and metabolic rejuvenation on anaerobic storage of red cells," *Transfusion*, 48:2096-2105 (2008).
Yoshida et al., "Anaerobic storage of red blood cells," *Blood Transfus*, 8:220-236 (2010).
Yoshida et al., "Oxygen content—uncontrolled and overlooked parameter associated with stored red cell concentrate: Unexpectedly wide distribution," *Vox Sang* 112: P-244 (2017) Abstract.
Yoshida et al., "Enhancing uniformity and overall quality of red cell concentrate with anaerobic storage," *Blood Transfus* 15: 172-81 (2017).
Yoshida et al., "Toward a comprehensive biochemical model of human erythrocyte: relationship between metabolic and osmotic state of the cell and the state of hemoglobin," *Prog Clin Biol Res* 319: 179-93; discussion 94-6 (1989).
Yoshida et al., "Unexpected Variability of Hemoglobin Oxygen Saturation in Packed Red Blood Cells upon Donation Suggests Uncontrolled and Overlooked Parameter Associated with the Development of the Storage Lesion," *Transfusion* 57 (2017).
Yoshida et al., "Red blood cell storage lesion: causes and potential clinical consequences" *Blood Transfus* 17: 27-52 (2019).
Yoshida et al., "Reduction of Microparticle Generation During Anaerobic Storage of Red Blood Cells," *Transfusion* 52: 83A (2012).
Yuasa et al., "Improved extension of platelet storage in a polyolefin container with higher oxygen permeability," *British Journal of Hematology* 126:153-159 (2004).
Zaroulis, et al., "Lactic acidemia in baboons after Transfusion of red blood cells with improved oxygen transport function and exposure to severe arterial hypoxemia," *Transfusion* 19: 420-5 (1979).
Zavizion et al., "Inactivation of mycoplasma species in blood by Inactine PEN110 process," *Transfusion* 44:286-293 (2004).
Zhang et al., "Modification of Si(100) surface by the grafting of poly(ethylene glycol) for reduction in protein adsorption and platelet adhesion," *J Biomed Mater Res*, 56:324-332 (2001).
Zielinski et al., "Back to the future: The renaissance of whole-blood transfusions for massively hemorrhaging patients," *Surgery* 155(5) 883-886 (2014).
Zielinski, et al., "Prehospital Blood Transfusion programs: Capabilities and lessons learned," *J Trauma Acute Care Surg* 82: S70-s8 (2017).
Zimrin et al., "Current issues relating to the transfusion of stored red blood cells," *Vox Sanguinis*, 96:93-103 (2009).
Zimring et al., "Established and theoretical factors to consider in assessing the red cell storage lesion," *Blood*, 125:2185-2190 (2015).
Zingarelli et al., "Part I: Minimum Quality Threshold in Preclinical Sepsis Studies (MQTiPSS) for study design and humane modeling endpoints," *Shock* 51: 10-22 (2019).
Zink et al., "Noninvasive Evaluation of Active Lower Gastrointestinal Bleeding: Comparison Between Contrast-Enhanced MDCT and 99mTcLabeled RBC Scintigraphy," *American Journal of Roentgenology* 191: 1107-14 (2008).
Zinkham et al., "Carboxyhemoglobin levels in an unstable hemoglobin disorder (Hb Zurich): effect on phenotypic expression," *Science* 209: 406-8 (1980).
Zolla et al., "Classic and alternative red blood cell storage strategies: seven years of '-omics' investigations," *Blood Transfus* 13:21-31 (2015).
Basu et al., "Overview of blood components and their preparation," Indian J Anaesth 58:529-537 (2014).
Extended European Search Report dated Feb. 21, 2022 in European Patent Application No. 21199989.1.
Dupont, "What is Tyvek(R)," downloaded from www.dugon.com/what-is-tyvek.html.
"Oxygen O2 in Blood," downloaded from http://web.utk.edu/~rstrange/wfs550/index2.html (2022).
Prowse et al., "Commercially available blood storage containers," *Vox Sanguinis* 106(1): 1-13 (2014).
Van der Meer et al., "Platelet preservation: Agitation and containers," *Transfusion and Apheresis Science* 44:297-304 (2011).
Wang et al., "The contribution of oxidative stress to platelet senescence during storage" *Transfusion* (2019).
International Search Report for PCT/US2020/057754 dated Feb. 15, 2021.
Mufti, "Treatment of whole blood (WB) and red blood cells (RBC) with S-303 inactivates pathogens and retains in vitro quality of stored RBC," Biologicals 38:14-19 (2010).
Seghatchian, "Pathogen inactivation of whole blood and red cell components: An overview of concept, design, developments, criteria of acceptability and storage lesion," Transfusion and Apheresis Science 49:357-363 (2013).

(56) References Cited

OTHER PUBLICATIONS

Winter, "Red blood cell in vitro quality and function is maintained after S-303 pathogen inactivation treatment," Transfusion 54:1798-1807 (2014).

* cited by examiner

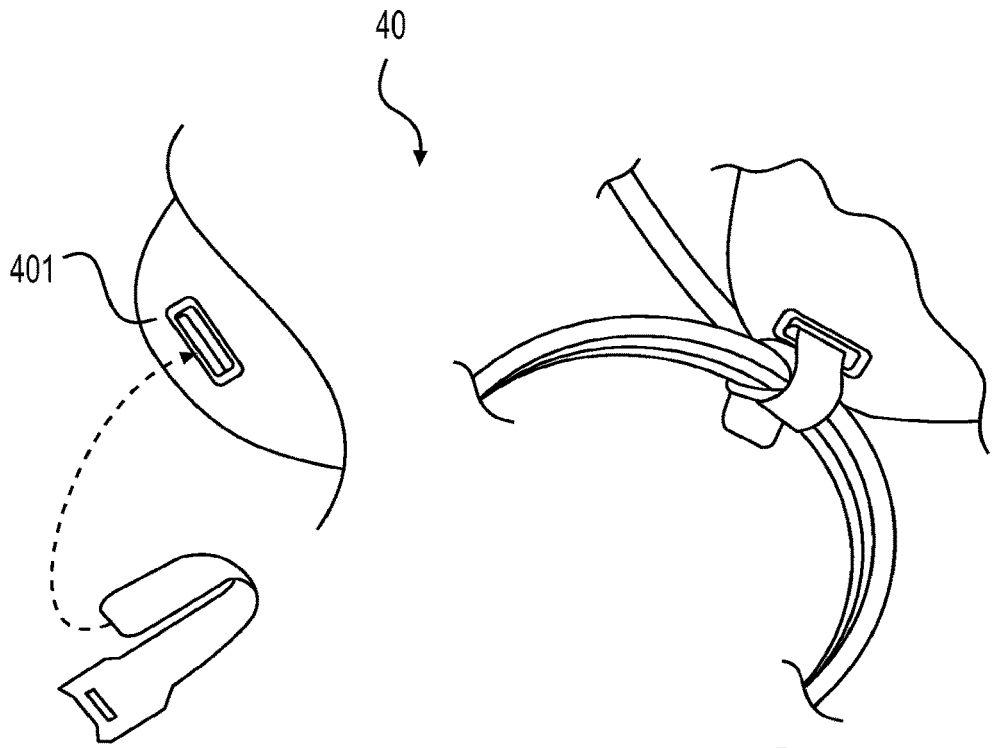
FIG. 6A
FIG. 6B
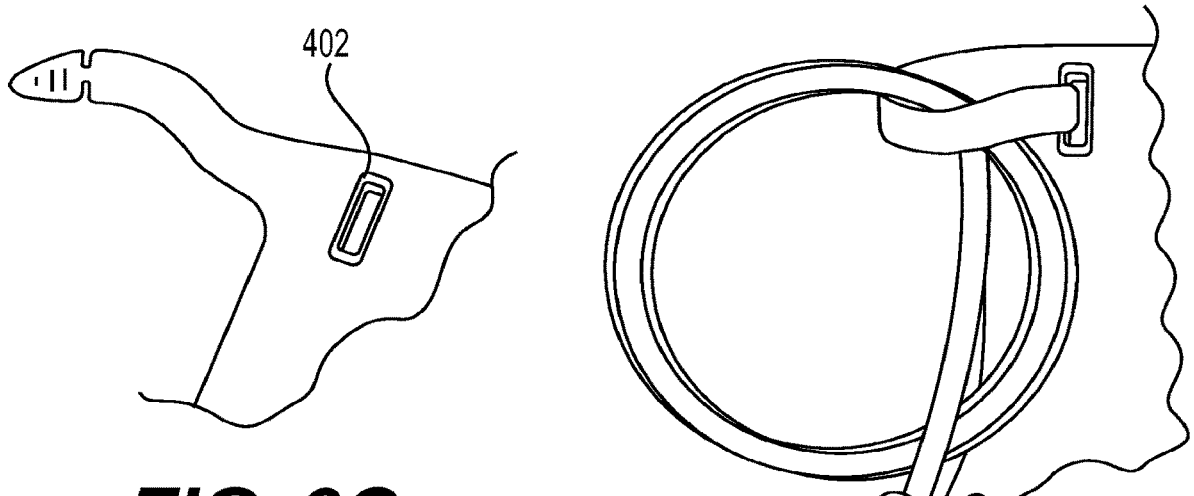
FIG. 6C
FIG. 6D

ANAEROBIC BLOOD STORAGE CONTAINERS

CROSS-REFERENCE TO RELATED APPLICATIONS

This application is a continuation application of U.S. application Ser. No. 15/708,925 filed Sep. 19, 2017 (now U.S. Pat. No. 10,849,824), which is a continuation of U.S. application Ser. No. 15/475,898 filed Mar. 31, 2017 (now U.S. Pat. No. 9,801,784), which is a continuation of International Application No. PCT/US2016/029069 filed Apr. 22, 2016, which claims priority to U.S. Provisional Patent Application No. 62/151,957 filed Apr. 23, 2015, and U.S. Provisional Patent Application No. 62/151,839 filed Apr. 23, 2015, each of which are incorporated herein in their entireties.

FIELD OF THE INVENTION

The present disclosure relates to an improved anaerobic storage bag (ASB) and methods for the improved preservation of whole blood and blood components. More particularly, the disclosure relates to improved devices and methods for the anaerobic storage of oxygen and oxygen and carbon dioxide depleted blood and blood components that provide for an extended shelf life prior to use, improved usability in a collection center, and reduced ingression of oxygen. The methods, devices and kits of the present disclosure provide for improved quality of blood and blood components for transfusion and improved patient safety and outcome.

BACKGROUND OF THE INVENTION

The supplies of liquid blood and blood components are currently limited by storage systems used in conventional blood storage practices. Using current systems, stored blood expires after a period of about 42 days of refrigerated storage at a temperature above freezing (i.e., 4° C.) as packed blood cell preparations. For example, in 2007, more than 45 million units of red blood cells (RBCs) were collected and stored globally (15.6 million in the US). During refrigerated storage, RBCs become progressively damaged by complicated biological changes collectively referred to as "storage lesions." When transfused within the current 6-week limit, stored RBCs have lower quality as well as potential toxicity, which can be manifested as side effects of transfusion therapy. Among the observed storage lesions are altered biochemical and physical parameters associated with stored red blood cells. Examples of these alterations include in vitro measured parameters such as reduced metabolite levels (adenosine triphosphate (ATP) and 2,3 diphosphoglycerate (2,3-DPG)), increased levels of cell-free iron, hemolysis, increased levels of microparticles, reduced surface area, echinocytosis, phosphatidylserine exposure, and reduced deformability. Expired blood cannot be used and must be discarded because it may harm the ultimate recipient. These reasons and others limit the amount of readily available high quality blood needed for transfusions.

When stored conventionally, stored blood undergoes a steady deterioration which is associated with various storage lesions including, among others, hemolysis, hemoglobin degradation, and reduced ATP and 2,3-DPG concentrations. When transfused into a patient, the effects of the steady deterioration during storage manifest, for example, as a reduction in the 24-hour in vivo recovery. Because of these and other medical sequelae of transfusion of stored blood, a variety of approaches have been developed to minimize the effects of storage on blood and to improve medical outcomes. See, for example, Zimring et al., "Established and theoretical factors to consider in assessing the red cell storage lesion" in *Blood*, 125:2185-90 (2015).

A number of approaches have been developed aimed at minimizing storage lesions and improving transfusion outcomes. One approach has been the development of additive solutions included during storage. Examples of this approach include U.S. Pat. No. 4,769,318 to Hamasaki et al. and U.S. Pat. No. 4,880,786 to Sasakawa et al. which are directed to additive solutions for blood preservation and activation. For example, Rejuvesol (available from Citra Lab LLC, Braintree, MA) is added to blood after cold storage (i.e., 4° C.) just prior to transfusion or prior to freezing (i.e., at −80° C. with glycerol) for extended storage. U.S. Pat. No. 6,447,987 to Hess et al. is directed to additive solutions for the refrigerated storage of human red blood cells. An alternative approach is to freeze the blood and prevent the development of storage lesions. Storage of frozen blood is known in the art, but such frozen blood has limitations. U.S. Pat. No. 6,413,713 to Serebrennikov is directed to a method of storing blood at temperatures below 0° C. See Chaplin et al., "Blood Cells for Transfusion," *Blood*, 59: 1118-20 (1982), and Valeri et al., "The survival, function, and hemolysis of human RBCs stored at 4 degrees C. in additive solution (AS-1, AS-3, or AS-5) for 42 days and then biochemically modified, frozen, thawed, washed, and stored at 4 degrees C. in sodium chloride and glucose solution for 24 hours," *Transfusion*, 40:1341-5 (2000). Another approach relates to the containers for blood storage as provided by U.S. Pat. No. 4,837,047 to Sato et al.

One approach that has proven successful in improving blood quality and extending its utility is through the depletion of oxygen and storage under anaerobic conditions. U.S. Pat. No. 5,624,794 to Bitensky et al., U.S. Pat. No. 6,162,396 to Bitensky et al., and U.S. Pat. No. 5,476,764 to Bitensky are directed to the storage of red blood cells under oxygen-depleted conditions. U.S. Pat. No. 5,789,151 to Bitensky et al. is directed to blood storage additive solutions. Among the benefits of storing blood under oxygen depleted conditions are improved levels of ATP and 2,3-DPG, reduced hemolysis. Storing blood under oxygen depleted conditions can also result in reduced microparticle levels, reductions in the loss of deformability, reduced lipid and protein oxidation and higher post transfusion survival when compared to blood stored under conventional conditions.

U.S. Pat. No. 6,162,396 to Bitensky et al. (the '396 patent) discloses anaerobic storage bags for blood storage that comprise an oxygen impermeable outer layer, a red blood cell (RBC) compatible inner layer that is permeable to oxygen having an oxygen scrubber placed between the inner and outer layers. The blood storage device further comprises at least two ports for conventional sterile connections for introducing whole blood or RBCs into the device. The '396 patent generally discloses oxygen impermeable outer layers but does not provide guidance regarding specific types of materials or suitable construction methods. Similarly, the '396 patent discloses inner blood compatible layers generally but does not provide guidance regarding appropriate materials and construction methods. Similarly, the '396 patent does not provide guidance on tubing materials and methods to gain access to the inner blood bag and contents while maintaining a reduced oxygen environment.

During the course of research to develop an ASB for use in blood collection and blood banking operations, it was observed that additional considerations were necessary.

First, in preparing oxygen impermeable outer layers, it was observed that not all of the materials identified as suitable in the '396 patent could be used in practicable devices. Specifically, it was observed that certain aluminum foil laminated membranes became compromised when creased, wrinkled or folded. More problematic, is that upon introduction of blood into such bags, the increase in volume directly led to the formation of such integrity compromising creases. To avoid this complication, appropriate materials having sufficient flexibility are required. Alternatively, ASBs having suitable expansion features that provide for the accommodation of the blood are required.

Also during the course of development, it was observed that the bag integrity needed to be maintained at the various ports to prevent ingress of oxygen prior to use and also during storage. Another source of oxygen ingress was observed at seams and joints wherein wider seals provided for both decreasing oxygen leakage and preventing outer and inner bag failure. It was further observed that the standard PVC tubing used in blood banking operations had significant permeability to oxygen and incompatibility with methods to create an oxygen impermeable seal where it passed through the outer oxygen impermeable barrier. Even further, conventional blood collection kits require transfer tubing ranging in length from about greater than or equal to 200 mm as well as collection tubing having a length greater than or equal to 800 mm that are also potential sources of oxygen introgression. See ISO 3826-1:2013. Thus, blood collection kits for anaerobic storage of blood must account for this source of oxygen that can diminish the capacity of an oxygen sorbent placed in the ASB and significantly reduce the shelf life of the resulting bags.

Therefore, there is a need for improved anaerobic blood storage bags that provide for extended shelf life a blood collection kit including such bags. There is also a need for improved anaerobic storage bags that can provide for the ingression of oxygen through the tubing associated with blood collection kits. Finally, there is a need to identify suitable materials that can accommodate routine handling of blood storage bags that do not compromise the integrity of the oxygen barrier.

Finally, the integration of oxygen indicators into improved anaerobic blood storage bags provides additional levels of quality control that helps inform the users of possible oxygen ingress that are large enough to compromise the ability to the storage bag to maintain the depleted blood in an oxygen depleted condition.

SUMMARY OF THE INVENTION

The present disclosure provides for, and includes, a blood storage device for storing oxygen depleted blood comprising an outer receptacle substantially impermeable to oxygen, a collapsible blood container and at least one inlet/outlet passing through the outer receptacle and that is in fluid communication with the collapsible container and that is substantially impermeable to oxygen.

The present disclosure provides for, and includes, a blood storage device for storing oxygen depleted blood comprising an outer receptacle substantially impermeable to oxygen, a collapsible blood container and at least one inlet/outlet passing through the outer receptacle and that is in fluid communication with the collapsible container and that is substantially impermeable to oxygen, and an oxygen sorbent situated within the outer receptacle.

The present disclosure provides for, and includes, a blood storage device for storing oxygen depleted blood comprising a multilayered membrane that combines an outer receptacle substantially impermeable to oxygen, a collapsible blood container and at least one inlet/outlet passing through the outer receptacle and that is in fluid communication with the collapsible container and that is substantially impermeable to oxygen, and an oxygen sorbent situated within the multilayered membrane.

The present disclosure provides for, and includes, a blood storage device for storing oxygen depleted blood comprising a blood compatible outer receptacle that is substantially impermeable to oxygen, a collapsible blood container and at least one inlet/outlet passing through the outer receptacle and that is in fluid communication with the collapsible container and that is substantially impermeable to oxygen wherein oxygen depleted blood having an oxygen saturation level of less than 20% is maintained in an oxygen depleted state for at least 64 days.

The present disclosure provides for, and includes, a method for storing deoxygenated blood comprising placing deoxygenated blood into a blood storage device as described herein.

The present disclosure provides for, and includes, a method of further reducing the oxygen saturation of blood during storage comprising transferring oxygen depleted blood for storage having an oxygen saturation level of less than 20% to a blood storage device and storing the oxygen depleted blood for storage for a time period wherein the time period is at least 1 week.

BRIEF DESCRIPTION OF THE DRAWINGS

Some aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description, taken with the drawings, makes apparent to those skilled in the art how aspects of the disclosure may be practiced.

FIGS. 6A to 6F illustrate tubing management features according to aspects of the present disclosure.

Corresponding reference characters indicate corresponding parts throughout the several views. The examples set out herein illustrate several embodiments of the invention but should not be construed as limiting the scope of the invention in any manner.

DETAILED DESCRIPTION

Figure 1A:
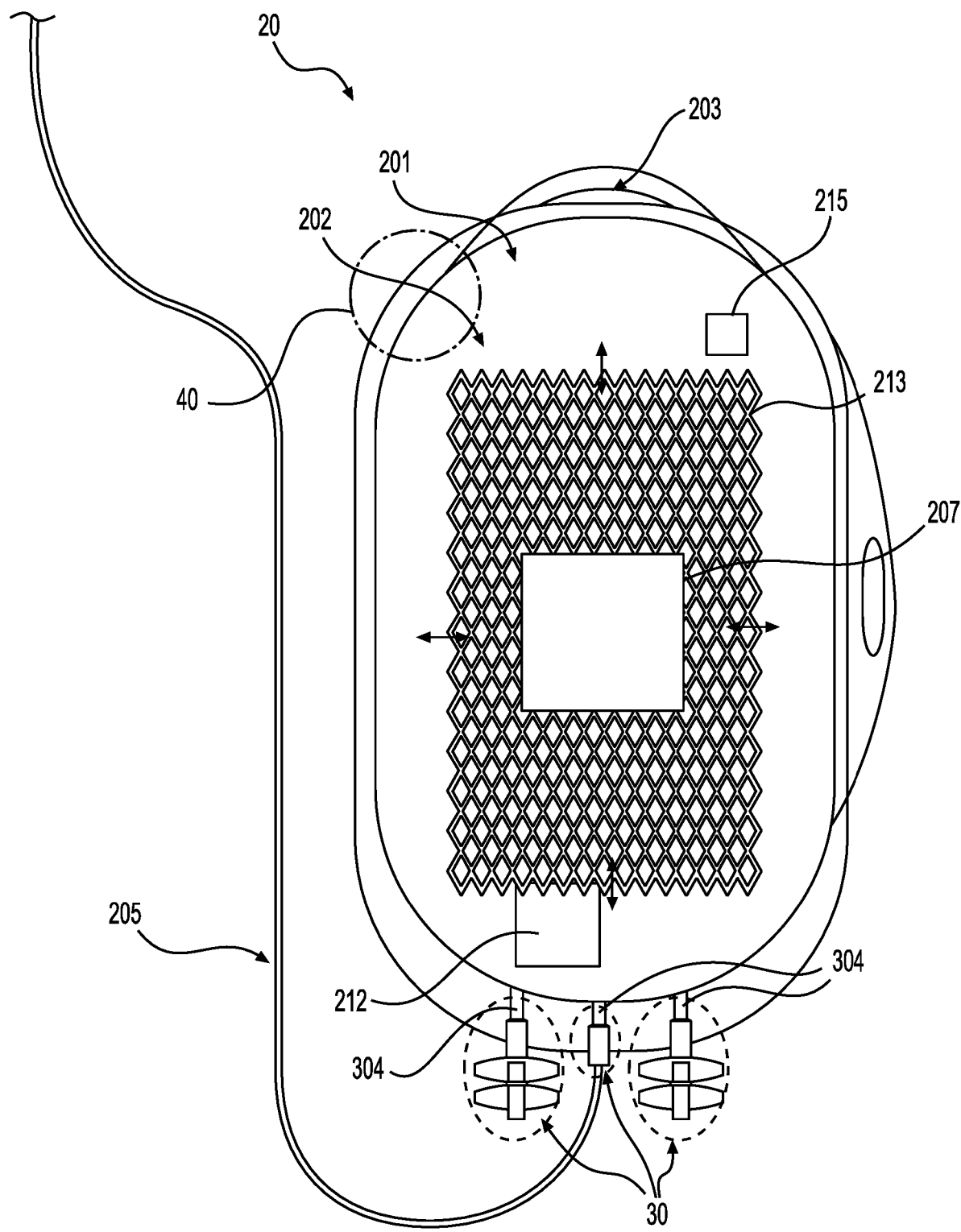
FIGS. 1A to 1C illustrate an exemplary embodiment of an improved anaerobic storage bag according to the present disclosure.
Figure 1B:
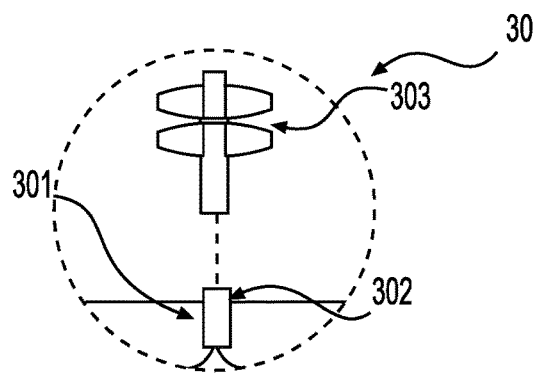

Unless defined otherwise, technical and scientific terms as used herein have the same meaning as commonly understood by one of ordinary skill in the art. One skilled in the art will recognize many methods can be used in the practice of the present disclosure. Indeed, the present disclosure is in no way limited to the methods and materials described. Any references cited herein are incorporated by reference in their entireties. For purposes of the present disclosure, the following terms are defined below.

As used herein, the term "bag" refers to collapsible containers prepared from a flexible material and includes pouches, tubes, and gusset bags. As used herein, and included in the present disclosure, the term includes folded bags having one, two, three, or more folds and which are sealed or bonded on one, two, three, or more sides. Bags may be prepared using a variety of techniques known in the art including bonding of sheets of one or more materials. Methods of bonding materials to form bags are known in the art. Also included and provided for in the present disclosure are containers prepared by injection and blow molding. Methods to prepare blow molded and injection molded containers are known in the art. Preferred types of blow molded or injection molded containers are flexible containers that can be reduced in size for efficient packing and shipping while being capable of expanding to accommodate blood or blood components for reduction of oxygen. They also may be designed to conform to the volume of the blood until they are fully expanded. As used throughout the present disclosure, the bags are a form of collapsible container and the two terms are used interchangeably throughout the present disclosure.

As used herein, the term "collapsible container" includes bags, containers, enclosures, envelopes, pouches, pockets, receptacles, and other devices that can contain and retain a liquid or fluid. In certain aspects, the collapsible container may be manufactured by conventional means such as injection molding or insert molding. In other aspects, the collapsible container may be prepared from sheets of polymer materials that are bonded together using methods known in the art to prepare containers capable of holding a volume. Such collapsible containers are well known in the art. See, for example, U.S. Pat. No. 3,942,529 issued to Waage; U.S. Pat. No. 4,131,200 issued to Rinfret; and U.S. Pat. No. 5,382,526 issued to Gajewski et al. Suitable methods for bonding polymer materials to prepare collapsible containers according to the present disclosure include heat welding, ultrasonic welding, radio frequency (RF) welding, and solvent welding. In certain aspects, multiple bonding methods may be used to prepare collapsible containers according to the present disclosure. Collapsible container according to the present disclosure include enclosures having one or more pleats, folds, diaphragms, bubbles, and gussets. Methods for preparing collapsible containers are known in the art. See, for example, U.S. Pat. No. 3,361,041 issued to Grob; U.S. Pat. No. 4,731,978 issued to Martensson; U.S. Pat. No. 4,998,990 issued to Richter et al.; and U.S. Pat. No. 4,262,581 issued to Ferrell. Also included and provided for in the present disclosure are containers having combinations of both flexible and inflexible parts, wherein the flexible parts allow for the expansion of the volume through, for example, pleats, folds or gussets and other similar geometric features in the packaging shape, whereas the inflexible parts may provide rigidity and geometry definition to the container. Methods and designs for preparing collapsible containers having both flexible and inflexible parts are known in the art, such as described by Randall in U.S. Pat. No. 6,164,821 and by LaFleur in U.S. Pat. No. 5,328,268. Others are described by Yeager in U.S. Pat. No. 6,076,664 and by David in U.S. Patent Application Publication No. 2014/0248005A1, also known in the art as a "stand up pouch."

As used herein, the term "ingressed oxygen" refers to oxygen that enters the blood storage device during the period of storage of oxygen depleted blood. Ingressed oxygen further includes oxygen that enters the blood storage device during shelf storage. Such ingressed oxygen can render the blood storage device inoperative during shelf storage if not minimized or preferably eliminated. In an aspect, ingressed oxygen can result in the consumption of the gas binding capacity of the sorbent (either oxygen or carbon dioxide) rendering the device deficient and unable to maintain the blood storage device in an anaerobic state and further unable to maintain the oxygen reduced stored blood. Ingressed oxygen includes oxygen that enters the device through the substantially impermeable barriers of the device and it is recognized that absolute integrity in typical devices is either not possible or is cost prohibitive. More generally, ingressed oxygen can enter the device through the seals or welds of the outer receptacle 201, the inlet/outlet 30, tubing 304, and tubing 205. More specifically, it was discovered that standard tubing used in blood collection devices (e.g., collection and transfer tubes) were significant sources of ingressed oxygen that rendered anaerobic blood storage devices known previously in the art inadequate. As shown in the examples below, the tubing was the primary source of ingressed oxygen. Even further, while the present design eliminates the majority of the ingressed oxygen observed in previous anaerobic storage bags, it will be appreciated that the absolute elimination of ingressed oxygen may not be possible. The problem of ingressed oxygen manifests in a significantly decreased shelf life of unused blood storage devices as well as the inability to maintain the blood in a suitably oxygen depleted state. Moreover, even with the incorporation of the elements of the blood storage device 20 of the present disclosure, it is preferable to include an oxygen sorbent 207 that is capable of absorbing not only any residual oxygen present in the oxygen depleted blood, but also that amount of unwanted ingressed oxygen that still enters into the system.

As used herein, the term "blood" refers to whole blood, leukoreduced RBCs, platelet reduced RBCs, and leukocyte and platelet reduced RBCs. The term blood further includes packed red blood cells, platelet reduced packed red blood cells, leukocyte reduced packed red blood cells (LRpRBC), and leukocyte and platelet reduced packed red blood cells. The temperature of blood can vary depending on the stage of the collection process, starting at the normal body temperature of 37° C. at the time and point of collection, but decreasing rapidly to about 30° C. as soon as the blood leaves the patient's body and further thereafter to room temperature in about 6 hours when untreated, and ultimately being refrigerated at between about 4° C. and 6° C.

As used herein, the term "whole blood" refers to a suspension of blood cells that contains red blood cells (RBCs), white blood cells (WBCs), platelets suspended in plasma, and includes electrolytes, hormones, vitamins, antibodies, etc. In whole blood, white blood cells are normally present in the range between 4.5 and $11.0 \times 10^9$ cells/L and the normal RBC range at sea level is $4.6$-$6.2 \times 10^{12}$/L for men and $4.2$-$5.4 \times 10^{12}$/L for women. The normal hematocrit, or percent packed cell volume, is about 40-54% for men and about 38-47% for women. The platelet count is normally $150$-$450 \times 10^9$/L for both men and women. Whole blood is collected from a blood donor, and is usually combined with an anticoagulant. Whole blood, when collected is initially at about 37° C. and rapidly cools to about 30° C. during and shortly after collection, but slowly cools to ambient temperature over about 6 hours. Whole blood may be processed according to methods of the present disclosure at collection, beginning at 30-37° C., or at room temperature (typically about 25° C.). As used herein, a "unit" of blood is about 450-500 ml including anticoagulant.

As used herein, "red blood cells" (RBCs) includes RBCs present in whole blood, leukoreduced RBCs, platelet reduced RBCs, and leukocyte and platelet reduced RBCs. Human red blood cells in vivo are in a dynamic state. The red blood cells contain hemoglobin, the iron-containing protein that carries oxygen throughout the body and gives red blood its color. The percentage of blood volume composed of red blood cells is called the hematocrit. As used herein, unless otherwise limited, RBCs also includes packed red blood cells (pRBCs). Packed red blood cells are prepared from whole blood using centrifugation techniques commonly known in the art. As used herein, unless otherwise indicated, the hematocrit of pRBCs is about 70%.

As used herein the term "about" refers to ±10%.

The terms "comprises," "comprising," "includes," "including," "having," and their conjugates mean "including but not limited to."

The term "consisting of" means "including and limited to."

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a," "an," and "the" include plural references unless the context clearly dictates otherwise. For example, the term "a compound" or "at least one compound" may include a plurality of compounds, including mixtures thereof.

Throughout this application, various aspects of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3," "from 1 to 4," "from 1 to 5," "from 2 to 4," "from 2 to 6," "from 3 to 6," etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques, and procedures for accomplishing a given task including, but not limited to, those manners, means, techniques, and procedures either known to or readily developed from known manners, means, techniques, and procedures by practitioners of the chemical, pharmacological, biological, biochemical, and medical arts.

Referring to FIG. 1A, there is provided an illustration of an exemplary aspect of the present disclosure. The blood storage device 20 includes an outer receptacle 201 substantially impermeable to oxygen, a collapsible blood container 202 comprising, at least one inlet/outlet 30 passing through said outer receptacle 201 comprising a seal adaptor 301 and a bond 302, and an oxygen sorbent 207 situated within said outer receptacle 201, wherein said seal adaptor 301 and said bond 302 are substantially impermeable to oxygen, and said inlet/outlet 30 is in fluid communication with said collapsible container 202.

Figure 1C:
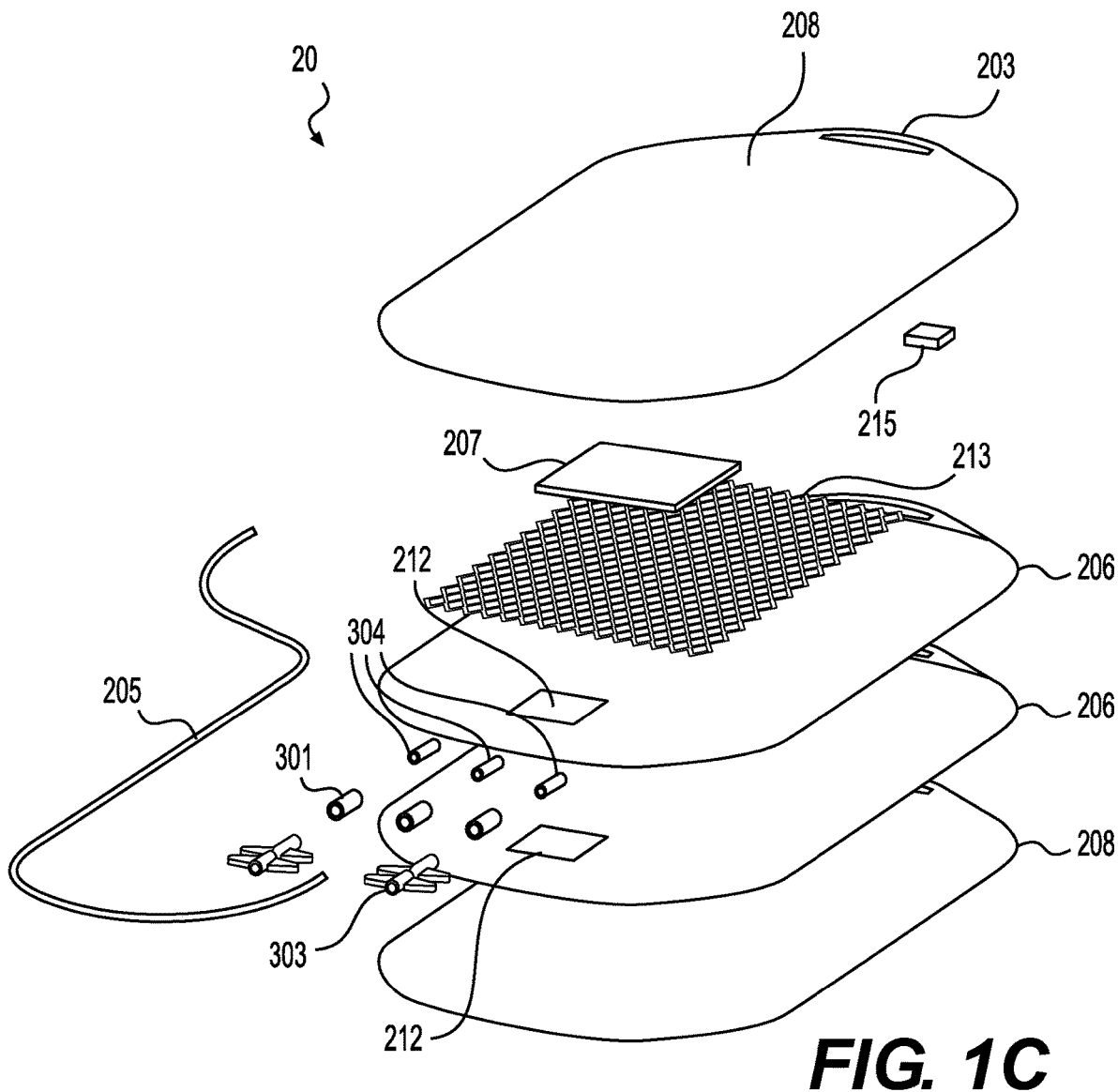
Figure 2A:
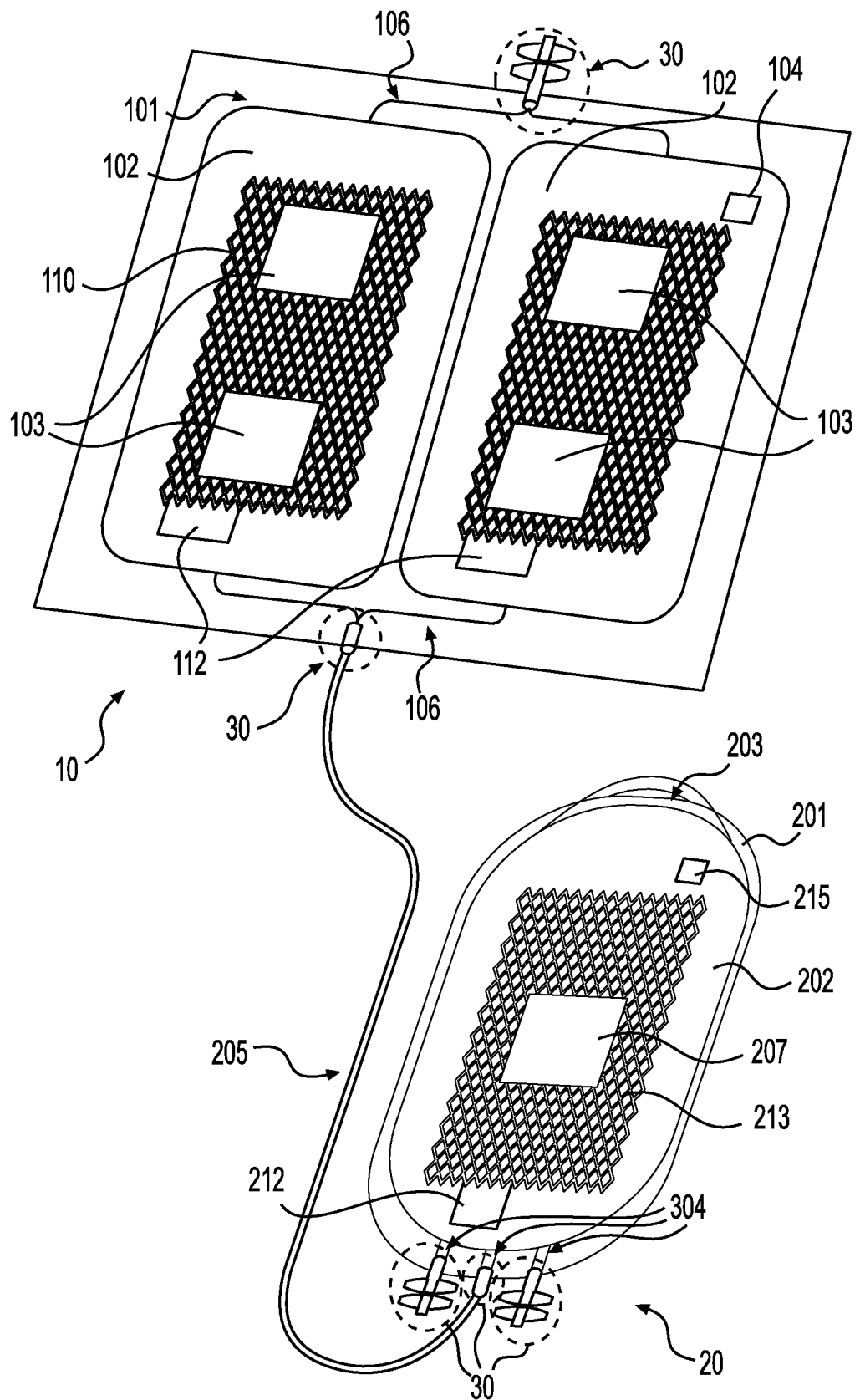
FIGS. 2A and 2B illustrate an exemplary embodiment of an oxygen reduction disposable storage system having a blood depletion device having two or three compartments, respectively, and an anaerobic storage bag according to the present disclosure.
Figure 2B:
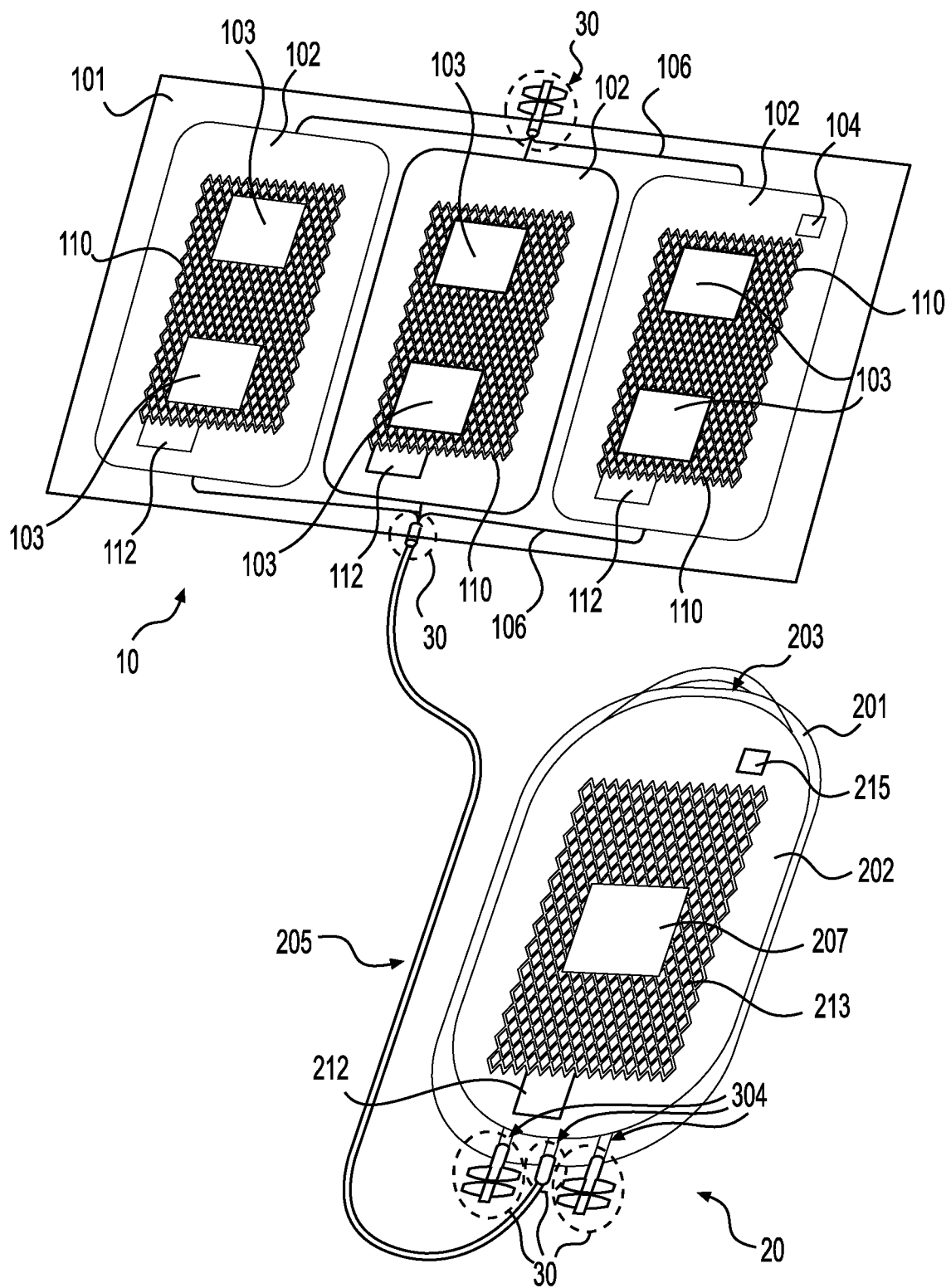

As used herein, the outer receptacles 201 are prepared from membrane materials 208 that are substantially impermeable to oxygen and optionally impermeable to carbon dioxide. In certain aspects, an outer receptacle 201 is prepared from flexible membrane materials 208. As illustrated in non-limiting aspects of the present disclosure in FIG. 1C, outer receptacle 201 may be prepared from one or more sheets of membrane material 208. In other aspects, and as described below, outer receptacle 201 may be prepared as a tube and sealed at the ends to create an outer receptacle. Also provided by the present disclosure is an outer receptacle 201 comprising a single sheet of membrane material 208, folded and sealed to prepare an outer receptacle 201. In further aspects, outer receptacle 201 may comprise two sheets of a membrane material 208 joined together. In yet other aspects, outer receptacle 201 may be prepared from two different membrane materials 208, each of which are substantially impermeable to oxygen and optionally impermeable to carbon dioxide. As discussed below, additional sheets of membrane material 208 may be joined together to prepare an outer receptacle 201 having an expansion feature 217 to accommodate an increase in volume of a collapsible blood container 202 that occurs upon transferring oxygen depleted blood to the blood storage device 20. The present disclosure provides blood storage device 20 with a hanging feature 203. The present disclosure also provides for and includes blow molded outer receptacles 201 comprising a suitable membrane material 208 that is substantially impermeable to oxygen and optionally impermeable to carbon dioxide.

The present disclosure provides for, and includes, an outer receptacle 201 substantially impermeable to oxygen. As used herein, an outer receptacle 201 that is substantially impermeable to oxygen is sufficiently impermeable to oxygen to allow no more than 10 cc of oxygen inside the receptacle over a period of 3 months, and more preferably no more than 5 cc of oxygen over 6 months. As used herein, the term "substantially impermeable to oxygen" (SIO) refers to materials and compositions that provide a barrier to the passage of oxygen from one side of the barrier to the other, sufficient to prevent significant increases in the partial pressure of oxygen. In certain aspects, a substantially impermeable membrane suitable for use in the preparation of an outer receptacle 201 is characterized by a Barrer value of less than 1.0 Barrer. In other aspects, a substantially impermeable membrane suitable for use in the preparation of an outer receptacle 201 is characterized by a Barrer value of between 0.001 and 0.2 Barrer. In certain aspects, a membrane suitable for use in the preparation of an outer receptacle and other elements of the present disclosure are materials characterized by a Barrer value of less than 0.02 Barrer. In certain aspects, a membrane suitable for use in the preparation of an outer receptacle and other elements of the present disclosure are materials characterized by a Barrer value of less than 0.002 Barrer.

The present disclosure also provides for, and includes, an outer receptacle 101 that is substantially impermeable to oxygen having a permeability to oxygen of less than about 0.5 cc of oxygen per square meter per day. In certain aspects, a membrane suitable for use in the preparation of an outer receptacle and other elements of the present disclosure are materials characterized by a Barrer value of less than 1.0 Barrer. In certain aspects, a membrane suitable for use in the preparation of an outer receptacle and other elements of the present disclosure are materials characterized by a Barrer value of less than 0.2 Barrer.

It is notable that few materials provide complete impermeability and that even the high impermeability of materials can be compromised when joining, welding, folding, and otherwise assembling an outer receptacle 201. As will be discussed below, blood storage device 20 may further incorporate one or more inlets/outlets 30 comprising a seal adaptor 301 and a bond 302 to the outer receptacle 201. In other aspects, the inlet/outlet 30 may comprise a single unitary tube that is substantially impermeable to oxygen that incorporates tubing 304, bond 302, and tubing 205. In other aspects, the unitary tube substitutes for tubing 304 and tubing 205 and is bonded to the outer receptacle 201. The outer receptacle 201 must also be designed to accommodate changes in volume of the inner collapsible blood container 202. In aspects according to the present disclosure, integrity of the impermeable barrier can be maintained by including a manifold as a seal adapter 301 or inlet/outlet 30 formulated in a diamond wedge shape according to FIG. 3C. Accordingly, special care is taken to incorporate specific design elements and manufacturing methods to ensure the integrity of the impermeable barrier.

Figure 3A:
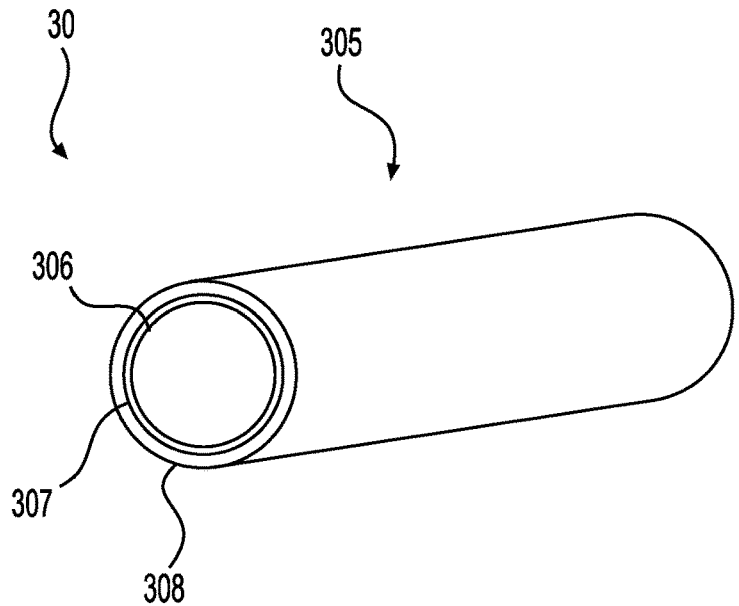
FIGS. 3A to 3C illustrate an exemplary embodiment of inlet/outlet barrier traversing tubes 305.
Figure 3B:
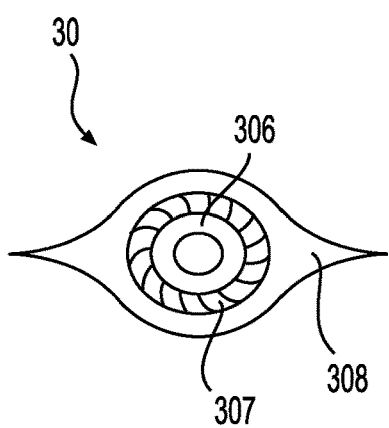
Figure 3C:
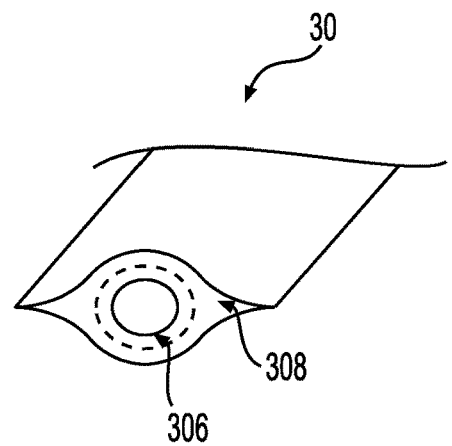

In one aspect of the present disclosure, a manifold is a seal adapter 301. In other aspects, the inlet/outlet 30 may be comprised of a plurality of inlet/outlets. In an aspect, the inlet/outlet 30 incorporates two barrier traversing tubes 305 and a manifold 301. In an aspect, the inlet/outlet 30 incorporates three barrier traversing tubes 305 and a manifold 301. An example of an manifold seal adaptor 301 having three inlet/outlets 30 and having three barrier traversing tubes 305 is provided in FIG. 3D. The present disclosure further provides for, and includes, barrier traversing tubes 305 having different diameters and functions. In one aspect of the present disclosure a barrier traversing tube 305 is a bilayer tube, for example as illustrated in FIG. 3C. In another aspect a barrier traversing tube(s) 305 is a trilayer tube, for example as illustrated in FIGS. 3A and 3B. In an aspect, an inlet/outlet 30 has a tube enabling a blood transfusion (e.g., an outlet for flowing blood from the inner collapsible blood container 202) and for spiking the inner collapsible blood container 202 of the blood storage device 20 with nutrients (e.g., a spike port). Also provided for and included is the use of a such spike ports to introduce oxygen into the inner collapsible blood container 202 to re-oxygenate the blood prior to transfusion.

The present disclosure also provides for, and includes, an outer receptacle 201 that is substantially impermeable to oxygen having a permeability to oxygen of less than about 0.5 cc of oxygen per square meter per day. In certain aspects, a membrane suitable for use in the preparation of an outer receptacle and other elements of the present disclosure are materials characterized by a Barrer value of less than 1.0 Barrer. In certain aspects, a membrane suitable for use in the preparation of an outer receptacle and other elements of the present disclosure are materials characterized by a Barrer value of less than 0.2 Barrer. In certain aspects, a membrane suitable for use in the preparation of an outer receptacle and other elements of the present disclosure are materials characterized by a Barrer value of less than 0.02 Barrer. In certain aspects, a membrane suitable for use in the preparation of an outer receptacle and other elements of the present disclosure are materials characterized by a Barrer value of less than 0.002 Barrer.

Materials and methods to prepare an outer receptacle 201 are known in the art. See, for example, U.S. Pat. No. 7,041,800 issued to Gawryl et al., U.S. Pat. No. 6,007,529 issued to Gustafsson et al., and U.S. Patent Application Publication No. 2013/0327677 by McDorman, each of which are hereby incorporated by reference in their entireties.

Impermeable materials are routinely used in the art and any suitable material can be used. In the case of molded polymers, additives are routinely added to enhance the oxygen (and $CO_2$) barrier properties. See, for example, U.S. Pat. No. 4,837,047 issued to Sato et al. For example, U.S. Pat. No. 7,431,995 issued to Smith et al. describes an oxygen- and carbon dioxide-impermeable receptacle composed of layers of ethylene vinyl alcohol copolymer and modified ethylene vinyl acetate copolymer, impermeable to oxygen and carbon dioxide ingress. In another aspect, the outer receptacle 201 is impermeable to oxygen and carbon dioxide.

In certain aspects, membranes that are substantially impermeable to oxygen may be laminated membranes. In an aspect, a laminated membrane that is substantially impermeable to oxygen is a laminated foil membrane. Membrane materials can be polymers or foil materials or multilayer constructions that are combinations of foils and polymers. In an aspect, a laminated membrane may be a polyester membrane laminated with aluminum. An example of a suitable aluminum laminated membrane, also known as a laminated foil, that is substantially impermeable to oxygen is known in the art. For example, U.S. Pat. No. 4,798,728 to Sugisawa discloses aluminum laminated foils of nylon, polyethylene, polyester, polypropylene, and vinylidene chloride. Other laminated films are known in the art. For example, U.S. Pat. No. 7,713,614 to Chow et al. discloses multilayer containers comprising an ethylene-vinyl alcohol copolymer (EVOH) resin that is substantially impermeable to oxygen. Additional materials suitable for an outer receptacle 201 include silicone oxide coated polyester, silicone oxide coated polypropylene, and silicone oxide coated nylon films. Suitable silicone oxide coated films include, but are not limited to, CERAMIS® silicone oxide coated films (available from Celplast Metallized Products Limited, Ontario, Canada). In an aspect, an outer receptacle 201 may be a barrier bag constructed by sealing three or four sides by means of heat sealing. The bag is constructed of a multilayer construction that includes materials that provide enhancement to $O_2$ and $CO_2$ barrier properties. The bag is constructed of a multilayer construction that includes materials that provide enhancement to $O_2$ and $CO_2$ barrier properties.

Table 1 below shows the oxygen transfer rate in Barrer for various bulk polymer materials tested at 23° C. and 0% R.H. using 25.4 μm (1 mil) thick samples:

TABLE 1

Oxygen transfer rate (OTR) in Barrer for various bulk polymer materials

| Bulk Material Properties (25 μm, 23° C., 0% R.H.) | OTR (Barrer) |
| --- | --- |
| EVOH (ethylene vinyl alcohol) | 0.00003-0.00007 |
| Barex ® 210 (acrylonitrile-methyl acrylate copolymer) | 0.0001-0.0002 |
| Barex ® 218 | 0.0002 |
| Biax Nylon-6 | 0.007-0.014 |
| OPET (oriented polyester) | 0.01-0.03 |
| OPP (oriented polypropylene) | 0.6-0.9 |
| Cast PP (polypropylene) | 0.8-1.1 |
| HDPE (high density polyethylene) | 0.8-1.1 |
| OPS (oriented polystyrene) | 1.6-2.2 |
| LDPE (low density polyethylene) | 2.5-3.0 |

Although EVOH has excellent barrier properties as a neat film, it rapidly loses these properties upon exposure to water vapor and especially with exposure to >70% R.H. Similarly, nylon-6 has good barrier properties that are susceptible to degradation in high moisture conditions. It is well known in the art to create multilayer laminated and/or coated structures to enhance the barrier properties over those of the bulk materials shown above. Such techniques and compositions include using a layer of EVOH disposed between layers of other polymers such as PA, PET, PE, PP or PVC to provide moisture protection to the EVOH layer and other desirable properties, thereby yielding a multilayer structure with excellent barrier properties. Such compositions are well known in the art and commercially available, such as the EVAL™ series of EVOH films from Kurary Company of America (Pasadena, TX).

Another method of producing an enhanced multilayer structure that is known in the art is by coating or metalizing a polymer substrate. Examples of such enhanced barrier films are shown in Table 2 below; since these are composite structures, the OTR is not dependent on the bulk film properties or thickness. An example of a suitable aluminum laminated membrane, also known as a laminated foil, that is substantially impermeable to oxygen is obtainable from Protective Packaging Corp. (Carrollton, TX).

TABLE 2

Enhanced Barrier Films

| Enhanced Barrier Films (23° C., 0% R.H.) | OTR (Barrer) |
| --- | --- |
| Metallized OPET (oriented polyester) | 0.022-0.24 |
| PVOH-coated OPP (ExxonMobil AOH) | 0.04 |
| Metallized biax Nylon-6 | 0.11 |
| PVDC (polyvinylidene chloride)-coated OPET | 0.7-1.1 |
| High Barrier PVDC-coated OPP | 0.7-1.3 |
| PVDC-coated biax Nylon-6 | 0.7-1.1 |
| Metallized OPP | 2.7-22.5 |
| Sealable PVDC-coated OPP | 3.2-7.6 |

(source: Polyprint.com)

Another method of producing an enhanced multilayer structure that is known in the art is by coating a polymer substrate with a barrier coating of silica or alumina, followed by an additional coating or polymer laminate to protect the silica or alumina coating. In an aspect, the silica can be silicon oxide (SiOx). Examples of such enhanced barrier films are shown in Table 3 below.

TABLE 3

RollPrint ® ClearFoil ® Enhanced Barrier Films

| RollPrint ® ClearFoil ® Enhanced Barrier Films | OTR (Barrer) | MVTR (gm/m$^2$-day-bar) |
| --- | --- | --- |
| ClearFoil ® V2 | 0.022 | 0.47 |
| ClearFoil ® D | 0.131 | 0.93 |
| ClearFoil ® V | 0.110 | 0.31 |
| ClearFoil ® M | 0.044 | 0.31 |
| ClearFoil ® F | 0.007 | 0.31 |
| ClearFoil ® A | 0.087 | 0.62 |
| ClearFoil ® W3 | 0.015 | 0.062 |
| ClearFoil ® X | 0.008 | 0.047 |
| ClearFoil ® Z | 0.002 | 0.012 |

(source: Rollprint.com)

The preferred structures include a PET base polymer outer layer, having good inherent oxygen barrier properties as a bulk material, coated with a middle layer of alumina to provide enhanced oxygen barrier properties over the PET and better optical clarity over a silica middle layer, followed by a polyethylene inner layer for heat sealability in fabricating the outer receptacle 201. The relative thickness of the alumina or silica layer primarily determines the oxygen barrier properties of the final structure of the film used in the fabrication of the outer receptacle 201.

In another aspect, a preferred structure includes a PET base polymer outer layer, having good inherent oxygen barrier properties as a bulk material, coated with a middle layer of alumina to provide enhanced oxygen barrier properties over the PET and better optical clarity over silica middle layer, followed by a PVC inner layer for bonding to other PVC components and having good blood compatibility. In some aspects, the PVC can be plasticized with DEHP to provide for enhanced blood compatibility when blood is stored in contact with the surface.

Other manufacturers make similar products with similar oxygen transmission rates, such as Renolit Solmed Wrapflex® films (American Renolit Corp., City of Commerce, CA) and Celplast Ceramis® films (Celplast Metallized Products, Toronto, Ontario, Canada).

Another approach applicable to the preparation of SIO materials includes multilayer graphitic films made by gentle chemical reduction of graphene oxide laminates with hydroiodic and ascorbic acids. See Su et al., "Impermeable barrier films and protective coatings based on reduced graphene oxide," *Nature Communications* 5, Article number: 4843 (2014), hereby incorporated by reference in its entirety. Nanoparticles to enhance oxygen barrier properties are also known in the art, for example, the multilayer barrier stack films provided by Tera-Barrier (Tera-Barrier Films Pte, Ltd, The Aries, Singapore) and described by Rick Lingle in *Packaging Digest Magazine* on Aug. 12, 2014.

In aspects according to the present disclosure, an outer receptacle 201 may be prepared from a gas impermeable plastic. In an aspect, the gas impermeable plastic may be a laminate. In certain aspects, the laminate may be a transparent barrier film, for example, a nylon polymer or ethylene vinyl acetate (EVA). In an aspect, the laminate may be a polyester film. In an aspect, the laminate may be Mylar®. In certain aspects, the laminate may be a metalized film. In an aspect, the metalized film may be coated with aluminum. In another aspect, the coating may be aluminum oxide. In another aspect, the coating may be silicon oxide. In another aspect, the coating may be an ethylene vinyl alcohol copolymer (EVOH) laminated between layers of low density polyethylene (LDPE).

An outer receptacle 201 of the present disclosure may be formed of one or more parts prepared from a gas impermeable material including a plastic or other durable lightweight material. In some aspects, an enclosure may be formed of more than one material. In an aspect, an outer receptacle 201 may be formed of a material and coated with a gas impermeable material to prepare a gas impermeable enclosure. In an aspect, a rigid or flexible outer receptacle 201 may be prepared from a plastic that may be injection molded or blow molded. In aspects according to the instant disclosure, the plastic may be selected from polystyrene, polyvinyl chloride, or nylon. In an aspect, outer receptacle 201 materials may be selected from the group consisting of polyester (PES), polyethylene terephthalate (PET), polyethylene napthalate (PEN), polyethylene (PE), high-density polyethylene (HDPE), polyvinyl chloride (PVC), polyvinylidene chloride (PVDC), low-density polyethylene (LDPE), polypropylene (PP), polystyrene (PS), high impact polystyrene (HIPS), polyamides (PA) (e.g., nylon), acrylonitrile butadiene styrene (ABS), polyacrylonitrile (PAN), polycarbonate (PC), polycarbonate/acrylonitrile butadiene styrene (PC/ABS), polyurethanes (PU), melamine formaldehyde (MF), plastarch material, phenolics (PF), polyetheretherketone (PEEK), polyetherimide (PEI) (Ultem), polylactic acid (PLA), polymethyl methacrylate (PMMA), polytetrafluoroethylene (PTFE), and urea-formaldehyde ethylvinyl acetate (EVA). In some aspects, ethylene vinyl alcohol copolymer (EVOH) may be used when part of a multilayered laminate. In certain aspects, outer receptacle 201 comprises polyethylene terephthalate (PET). In certain aspects, outer receptacle 201 comprises nylon-6. In certain aspects, the outer receptacle 201 may be polyethylene. In some aspects, the polyethylene outer receptacle 201 may comprise one or more polyethylene components that are welded together.

The present disclosure provides for, and includes, the preparation of outer receptacles 201 and inner collapsible blood container 202 from a membrane or film. As used herein, membranes generally refer to materials used to prepare an inner collapsible blood container 202 and films are used to refer to materials used to prepare outer receptacle 201. A membrane comprises one or more layers of materials in the form of a sheet that allows or prevents one or more substances to pass through from one side of the sheet to the other side of the sheet. As used herein, membranes may also be prepared as tubes suitable for connecting together components of blood storage devices 20, blood collection kits, or connecting together elements of blood collection devices, additive solution bags, leukocyte reduction filters, and depletion devices including depletion devices provided in U.S. Provisional Application No. 62/131,130, filed Mar. 15, 2015. As used throughout, it is understood that a membrane of the present disclosure may be formed as a sheet or a tube depending on the application. Also as previously provided, membranes to prepare outer receptacles 201 are substantially impermeable to oxygen while an inner collapsible blood container 202 is permeable to oxygen.

The present disclosure provides for and includes the preparation of outer receptacles 201 using heat sealing, blow molding, and injection molding techniques. Suitable materials for preparing outer receptacles 201 using heat sealing, blow molding, vacuum forming and injection molding include PET, standard and multilayer, polypropylene, polyethylene, polycarbonate, ABS, and other polymers known to those skilled in the art. Methods to prepare blow molded and injection molded outer receptacles 201 are known in the art, for example, a multilayer structure comprised of a barrier layer of ethylvinyl alcohol (EVOH or EVA) situated between two layers of polypropylene (PP) and offered by Kortec (Kortec, Inc., Rowley, MA) and also as described in U.S. Pat. No. 5,906,285 issued to Slat. Additives that strengthen the oxygen and $CO_2$ barrier properties of the polymers prior to molding or during their formulation or during setup are known in the art. One example is multilayer polymer co-injection resulting in a multilayer PET. Such a barrier resin is typically incorporated at the preform stage as an inner layer with PET on both sides, making PET the liquid contact layer as well as the outside layer. As provided below, suitable blow molded or injection molded outer receptacles 201 are impermeable to oxygen. In certain aspects, suitable heat sealed, vacuum formed, blow molded, or injection molded outer receptacles 201 are substantially impermeable both oxygen and carbon dioxide.

The present disclosure provides for, and includes, two types of materials for the preparation of either permeable or substantially impermeable membranes. In an aspect, permeable membranes according to the present disclosure provide for the passage of substances through the material, specifically but not necessarily exclusively, oxygen. In certain aspects, membranes are selected to permit the passage of oxygen and carbon dioxide while preventing the passage of water, proteins, salts (e.g., plasma components) and cells (e.g., red blood cells, white blood cells, and platelets). The rate of passage through a material depends on one or more properties including particle size, phase of material (liquid vs. gas), hydrophilicity, hydrophobicity, or solubility. The rate of passage, or flux, through a material also depends on the presence or absence of a driving force such as a difference in pressure (or partial pressure), differences in temperature, or differences in concentration between one side of the membrane and the other. The flux through a membrane is known as the membrane permeation flux. The membrane permeation flux of substances through a membrane is inversely proportional to the thickness of the membrane.

Membrane permeation flux, for a gas, is defined as the volume flowing through the membrane per unit area per unit time. The SI unit used is $m^3/m^2 \cdot s$. For gases and vapors, the volume is strongly dependent on pressure and temperature. Accordingly, permeation fluxes for gases are often given in terms of standard temperature and pressure (STP) which is defined as 0° C. and 1 atmosphere (1.0013 bar) (e.g., 273° K and 760 Torr). As noted above, the rate of passage depends on a driving force or difference between the two sides of the membrane, and this dependence is incorporated in the permeability coefficient, P, or simply the permeability.

Permeability (P) is defined as the permeability flux per unit of driving force per unit of membrane thickness. The SI unit for the permeability coefficient P is provided in Table 4 A common unit for gas separation, as in the present disclosure, is the Barrer and is also presented in Table 4. The term "$cm^3$ gas (STP)/$cm^2$ s" refers to the volumetric trans-membrane flux of the diffusing species in terms of standard conditions of 0° C. and 1 atmosphere pressure, the term cm refers to the membrane thickness, and cm-Hg refers to the trans-membrane partial pressure driving force for the diffusing species. Permeability must be experimentally determined.

TABLE 4

Permeability Units

Units of Permeability

"Volumetric" permeability  $1\ Barrer = \dfrac{10^{-10} \cdot cm^3\ gas(STP) \cdot (cm\ membrane\ thickness)}{(cm^2\ membrane\ area) \cdot s \cdot (cmHg\ pressure)}$ "Molar" permeability  $\dfrac{mol}{m \cdot Pa \cdot s}(SI\ units) = \dfrac{(mol_t\ permeating) \cdot (m\ membrane\ thickness)}{(m^2\ membrane\ area) \cdot s \cdot (Pa\ pressure)}$ Membranes suitable for the methods and devices according to the present disclosure include dense membranes, porous membranes, asymmetric membranes, and composite membranes. In certain aspects, suitable membranes may be multilayered membranes. In other aspects, suitable membranes are prepared from inorganic materials. Dense membranes are membranes prepared from solid materials that do not have pores or voids. Materials permeate dense membranes by processes of solution and diffusion. Examples of dense membranes include standard blood bag materials such as PVC, PVC-DEHP, PVC-Citrate, PVC-DINCH, polyolefins such as PE, LDPE, UHMWPE, PP, and OPP, urethanes, and silicone membranes (polydimethyl siloxane, or PDMS). Also included and provided for in the present disclosure are porous membranes that have pores of a particular range of sizes that separate on the basis of size exclusion. Examples of porous membranes suitable for use according to the present disclosure include PVDF and polysulfone membranes. Examples of composite membranes suitable for use according to the present disclosure are EMD Millipore's GVHP hydrophobic PVDF having 1.0 µm or 0.22 µm pore sizes.

Included and provided for by the present disclosure are composite membranes that are made of more than one material, often as laminates, wherein a dense material is applied to a porous support layer. Examples of composite membranes suitable for use according to the present disclosure are EMD Millipore's GVSP superhydrophobic PVDF having 1.0 µm or 0.22 µm pore sizes.

The present disclosure provides for, and includes, inner collapsible blood containers 202 prepared from membranes 206 that are characterized primarily by their permeability to oxygen. Unless indicated otherwise, a "substantially impermeable membrane" refers to membranes that are substantially impermeable to oxygen. However, in certain devices and methods, the membranes may be further characterized by the permeability or impermeability to carbon dioxide. For certain applications, the membrane material is substantially impermeable to oxygen and provides a barrier to the introduction of oxygen to the blood, blood component, or a blood collection kit comprised of multiple components. Such substantially impermeable membranes are generally used to prepare outer receptacles of the present disclosure. Suitable substantially impermeable membranes may also be used to prepare tubing for connective components of the devices and kits. Substantially impermeable membranes may comprise a monolayer or be laminated sheets or tubes having two or more layers.

The present disclosure provides for, and includes, inner collapsible blood containers 202 having a permeability of at least 3 Barrer. In certain aspects, the collapsible blood container 202 is substantially permeable to oxygen and has a permeability between 3 and 350 Barrer. In certain aspects, the inner collapsible blood container 202 is substantially permeable to oxygen and has a permeability between 3 and 11 Barrer. In certain aspects, the inner collapsible blood container 202 is substantially permeable to oxygen and has a permeability of between 11 and 350 Barrer. In certain aspects, the inner collapsible blood container 202 is substantially permeable to oxygen and has a permeability of between 11 and 99 Barrer. In certain aspects, the inner collapsible blood container 202 is substantially permeable to oxygen and has a permeability of between 99 and 250 Barrer.

Applications for using inner collapsible blood containers 202 having a permeability of between 3 and 350 Barrer include those wherein the blood transferred into and contained within the inner collapsible blood container has a suitably reduced oxygen content and protection from oxygen ingress during storage is desired. In certain aspects, an inner collapsible blood container 202 has a permeability of

TABLE 5

Permeability of Fluoropolymers (200 µm thick; 23° C.):

|  | Silicone | PTFE | PFA | FEP | ETFE | CTFE | ECTFE | PVDF | PVF | THV |
|---|---|---|---|---|---|---|---|---|---|---|
| Water vapor | 36000 | 5 | 8 | 1 | 2 | 1 | 2 | 2 | 7 | 1.73 |
| Oxygen | 500 | 1500 | n/a | 2900 | 350 | 60 | 100 | 20 | 12 | 696 |
| Nitrogen | 280 | 500 | n/a | 1200 | 120 | 10 | 40 | 30 | 1 | 217 |
| $CO_2$ | 2700 | 15000 | 7000 | 4700 | 1300 | 150 | 400 | 100 | 60 | 2060 | between 3 and 11 Barrer. In certain aspects, an inner collapsible blood container 202 has a permeability of between 11 and 350 Barrer. In certain aspects, the inner collapsible blood container 202 is substantially permeable to oxygen and has a permeability of between 11 and 99 Barrer. In certain aspects, an inner collapsible blood container 202 has a permeability of between 99 and 250 Barrer. In an aspect, an inner collapsible blood container 202 does not have a permeability of more than 350 Barrer. In another aspect, an inner collapsible blood container 202 does not have a permeability of 350 to 500 Barrer.

The present disclosure provides for, and includes, inner collapsible blood containers 202 having membranes 206 that have an oxygen permeability of between 3 and 11 Barrer. In certain aspects, the inner collapsible blood container is permeable to oxygen and has a permeability of 3 to 11 Barrer, and are exemplified by inner collapsible blood containers made from PVC-DEHP, PVC-Citrate, or PVC-DINCH. In certain aspects, the inner collapsible blood container is permeable to oxygen and has a permeability of 4.3 Barrer, and is exemplified by inner collapsible blood containers made from PVC-DEHP.

In certain aspects, the use of an oxygen permeable inner collapsible blood container 202 having a permeability of between 3 and 11 Barrer include those wherein the ingress of oxygen into the blood through inlet tube 205 may be removed by gas transfer through the inner collapsible blood container 202 and adsorbed by the oxygen sorbent 207. In certain aspects, the use of an oxygen permeable inner collapsible blood container 202 having a permeability of between 11 and 99 Barrer include those wherein the ingress of oxygen into the blood through inlet tube 205 may be removed by gas transfer through the inner collapsible blood container 202 and adsorbed by the oxygen sorbent 207.

The present disclosure also provides for, and includes, inner collapsible blood containers 202 having membranes 206 that are substantially permeable to oxygen. Membranes 206 that are substantially permeable to oxygen are generally used in the present disclosure for the preparation of inner collapsible blood containers 202. Substantially permeable membranes 206 may comprise a monolayer or may comprise a laminated structure having two or more layers.

In an aspect, oxygen permeable membranes 206 having a permeability to oxygen of greater than 11 Barrer are used for the preparation of a collapsible blood container 202. In another aspect, oxygen permeable membranes 206 having a permeability to oxygen greater than 99 Barrer are used for the preparation of a collapsible blood container 202. In yet another aspect, oxygen permeable membranes 206 have a permeability to oxygen of greater than 200 Barrer. In certain aspects, oxygen permeable membranes 206 suitable for use in the preparation of a collapsible blood container 202 are characterized by a Barrer value of greater than 3. In other aspects, oxygen permeable membranes 206 suitable for use in the preparation of a collapsible blood container 202 are characterized by a Barrer value of greater than 11. In certain other aspects, oxygen permeable membranes 206 suitable for use in the preparation of a collapsible blood container 202 are characterized by a Barrer value of greater than 99. Examples of oxygen permeable membranes 206 suitable for use in the preparation of a collapsible blood container 202 include Membrana Accurel® PP flat sheet membranes (Membrana division of Celgard, LLC, Charlotte, NC), PP flat sheet membranes from Sterlitech (Kent, WA), Metricel® PP hydrophobic filter membranes (Pall Corp., Port Washington, NY), Propafilm™ RGP, RF and RGN series of biaxially oriented polypropylene (BOPP) films from Innovia (Innovia Films, Inc., Atlanta, GA), P-Derm™ PS-1033 and PS-1045 silicone sheets from Polymer Sciences (Polymer Sciences, Inc., Monticello, IN), Silpuran® silicone sheets from Wacker (Wacker Silicones, Inc., Adrian MI), PVDF microporous membranes such as the GVHP and GVSP series from Millipore (EMD Millipore, Bedford, MA), and polysulfone microporous membranes such as from Pacific Membranes (Pacific Membranes, Inc., San Diego, CA) or the MicroPES® membrane from Membrana.

In an aspect, a membrane 206 that is substantially permeable to oxygen can be dense membranes prepared from non-porous materials. Examples of suitable materials that are capable of high oxygen permeability rates include silicones, polyolefins, epoxies, and polyesters. In another aspect, membranes that are substantially permeable to oxygen can be porous membranes prepared from organic polymers. A membrane 206 that is substantially permeable to oxygen may be prepared from a material selected from the group consisting of PVDF rendered hydrophobic, polytetrafluoroethylene (PTFE), polyamide (nylon), cellulose esters, polysulfone, polyethersulfone, polypropylene rendered hydrophobic, and polyacrylonitrile.

The present disclosure provides for, and includes, preparing membranes 206 that are substantially permeable to oxygen, not only by selecting the material, but also by selecting and controlling the thickness. As provided above, permeability is proportional to the thickness of the membrane. Accordingly, improved permeability may be achieved by decreasing the thickness of the membrane. In certain aspects, the minimum thickness is determined by its strength and resistance to puncture and tearing.

The present disclosure also provides for, and includes, membranes 206 that are substantially permeable to oxygen that are prepared using blow molding and injection molding techniques. Suitable materials for preparing inner collapsible blood containers 202 using blow molding and injection molding include silicone materials such as Bluestar 4350, 50 durometer, Silbione grade liquid silicone rubber and Shin-Etsu KEG-2000-40A/B Liquid Silicone. The silicone durometer choice is carefully chosen for collapsibility and permeability, followed by a well controlled wall thickness. Thinner materials will have a higher permeability. Methods to prepare blow molded and injection molded collapsible blood containers 202 are known in the art, for example, U.S. Pat. No. 4,398,642 issued to Okudaira et al.; U.S. Pat. No. 7,666,486 issued to Sato et al.; U.S. Pat. No. 8,864,735 issued to Sano et al.; and U.S. Patent Application Publication No. 2012/0146266 by Oda et al. In an aspect, a blow molded collapsible blood container 202 can be prepared using LDPE used in the manufacture of collapsible water containers. As provided below, suitable blow molded or injection molded collapsible blood containers 202 have a permeability to oxygen of at least 3 Barrer.

Applications for using oxygen permeable inner collapsible blood containers 202 having a permeability of between 3 and 350 Barrer include those wherein the blood transferred into and contained within the inner collapsible blood container have reduced oxygen content, wherein further oxygen reduction during storage is desired.

The present disclosure provides for, and includes, a membrane 206 that is substantially permeable to oxygen and may further be permeable to water vapor. Those of skill in the art would recognize that permeability to oxygen is often, but not always, accompanied by permeability to water vapor, as well other gases. Further, a person of skill in the art would recognize that as the permeability to oxygen increases, without more, the permeability to water vapor may also increase. According to the present disclosure, a membrane 206 may be selected based on its selective permeability for oxygen or oxygen and carbon dioxide while minimizing the permeability to water. Membranes 206 for use in collapsible blood containers 202 are selected to minimize water vapor permeability and to prevent the escape of water from the plasma or additive solutions during storage. In order to properly preserve the blood in the storage container for extended periods, up to and including 64 days, the blood should not be allowed to lose significant amounts of moisture from its content plasma. Accordingly the collapsible blood containers 202 are prepared from membranes 206 that are selected with consideration of the Moisture Vapor Transfer Rate (MVTR) of the material. In aspects according to the present disclosure, membranes 206 that are substantially permeable to oxygen have measured MVTR of 30 g/m²/24 hrs or less when tested at 23° C. and 100% R.H. MVTR's above 30, without more, are unsuitable above 30 g/m²/24 hrs.

The MVTR of materials being used at temperatures and conditions lower than those typically used for standard MVTR testing, such as in ASTM F-1249, notably the temperatures and conditions used for the refrigerated storage of blood and blood components, have actual MVTR's much lower than the values reported for the standardized tests conducted at higher temperatures. The MVTR of most materials is strongly dependent on the temperature being used or tested. For example, Propafilm® RHX heavy duty barrier coated film (PVDC-coated BOPP, Innovia Films, Inc., Atlanta, GA) has a MVTR of 2.9 g/m²/24 hrs. when tested at 38° C. and 90% R.H., but only a MVTR of 0.3 g/m²/24 hrs. when tested at 23° C. and 85% R.H.

The OTR (Oxygen Transmission Rate) of most materials is not dependent on the R.H. conditions. For example, Propafilm® RHX heavy duty barrier coated film (PVDC-coated BOPP, Innovia Films, Inc., Atlanta, GA) has an OTR of 2.1 Barrer when tested at either 23° C. and 85% R.H. or when tested at 25° C. and 0% R.H. per ASTM F-1927.

The moisture loss performance of an exemplary collapsible blood container membrane, Renolit ES-3000 (PVC-DEHP), which has a reported MVTR of 8.06 g/m²/24 hrs at standardized test conditions of 23° C. and 100% R.H. per ASTM F-1249, is well known and accepted in the industry for refrigerated storage of blood and routinely provides less than 2% weight loss for a plastic blood storage container as required per ISO 3826-1:2013. Other exemplary membranes used for the processing and storage of blood and blood components include Renolit ES-4000 (PVC-Citrate) having a reported MVTR of 26.4 g/m²/24 hrs at 23° C. and 100% R.H., Renolit 3406 (PVC-DINCH) having a reported standard MVTR of 5.5 g/m²/24 hrs at 23° C. and 100% R.H., and Renolit 8300 (polyolefin-elastomer blend), having a reported MVTR of 3.5 g/m²/24 hrs at 23° C. and 100% R.H.

The outer receptacle 201 provides further moisture barrier protection in addition to the oxygen barrier protection of the inner collapsible blood container 202. Due to the added protection of the outer receptacle 201, materials having higher MVTR's relative to the exemplary Renolit ES-3000 PVC-DEHP material are suitable for use in fabricating the collapsible inner blood container 202 while providing for higher OTR for the deoxygenation of the stored blood.

In aspects according to the present disclosure, a collapsible blood container 202 is prepared from a membrane material 206 having an MVTR of between 30 and 0.001 g/m²/day. On certain aspects, the MVTR is between 0.1 and 10 g/m²/day. In yet other aspects, the MVTR is between 1 and 8 g/m²/day.

In aspects according to the present disclosure, the MVTR is measured in g/m²/day at 23° C. and 100% R.H., and the collapsible blood container 202 is prepared from membrane material 206 that is PVC having a MVTR of about 3 g/m²/day. In other aspects, the PVC may contain DEHP and have a MVTR of about 8 g/m²/day. In other aspects, the PVC may contain DINCH and have a MVTR of about 5 g/m²/day. In other aspects, the PVC may contain Citrate and have a MVTR of about 10 g/m²/day. Membrane material 206 may also be prepared from foil films such as an aluminum foil films that allow for very little moisture loss and can provide an MVTR as low as 0.001 g/m²/day.

Polyethylene films are well known for having good moisture barrier properties, but relatively poor oxygen barrier properties. For example, LDPE is reported to have a MVTR of 17 g/m²-day but an OTR of 2500 cc/m²-day, while in comparison nylon is reported to have a MVTR of 260 g/m²-day and an OTR of 95 cc/m²-day. The barrier performance of polyethylene is proportional to the polymer density, thus low density PE materials have lower barrier performance properties than high density PE materials. Films such as 76 micrometer thick polyethylene providing MVTR of 6 g/m²/day provide breathability of oxygen without compromising moisture content. Also films of MVTR of 52 or 97 g/m²/day can provide good moisture barrier for the blood products. Polyethylene and other polyolefin materials having good moisture barrier characteristics are suitable for use as a permeable membrane 206 in preparing inner collapsible blood container 202.

TABLE 6

Water vapor permeability and water vapor/N2 selectivity for various polymers at 30° C. extrapolated to water vapor activity 0

| Polymer | Abbreviation | H2O Permeability (Barrer) | Selectivity |
| --- | --- | --- | --- |
| Polyethylene | (PE) | 12 | 5.71 |
| Polyvinylalcohol | (PVA) | 19 | 33,300 |
| Polypropylene | (PP) | 68 | 230 |
| Polyamide 6 (Nylon 6) | (PA-6) | 275 | 11,000 |
| Polyvinylchloride | (PVC) | 275 | 12,500 |
| Polyacrylonitril | (PAN) | 300 | 1,875,000 |
| Polyimide (Kapton) | (PI) | 640 | 5,333,300 |
| Polystyrene | (PS) | 970 | 400 |
| Polycarbonate | (PC) | 1,400 | 4,700 |
| Polysulfone | (PSF) | 2,000 | 8,000 |
| Natural rubber | (NR) | 2,600 | 300 |
| Polyethersulfone | (PES) | 2,620 | 10,480 |
| Polyphenyleneoxide | (PPO) | 4,060 | 1,070 |
| Cellulose acetate | (CA) | 6,000 | 24,000 |
| Sulfonated polyethersulofon | (SPES) | 15,000 | 214,300 |
| Ethyl cellulose | (EC) | 20,000 | 6,060 |
| Polydimethylsiloxane | (PDMS) | 40,000 | 140 |
| Sulfonated polyetheretherketon | (SPEEK) | 61,000 | 10,166,700 |
| 1000PEO40PBT60 | PEO-PBT | 104,000 | 40,000 |

As used herein, an inner collapsible blood container 202 is permeable to oxygen. In certain aspects, an inner collapsible blood container 202 is permeable to oxygen and carbon dioxide. In other aspects, an inner collapsible blood container 202 is permeable to oxygen and impermeable to carbon dioxide.

The permeability of an inner collapsible blood container 202 need only be sufficient to provide for the transfer of oxygen away from stored blood that may leak into the stored blood from, for example tube 205. In other aspects, the permeability of an inner collapsible blood container 202 may be sufficiently permeable to provide for additional deoxygenation of stored blood when combined with a sufficient amount of sorbent 207. In certain aspects, the outer receptacle 201 and collapsible blood container 202 may be a single integrated device 20 comprising a multilayered membrane having a substantially impermeable layer and an innermost blood compatible layer. A single integrated device 20 may further include a sorbent 207 comprising as a layer between the substantially impermeable layer and the innermost blood compatible layer.

In the course of development of blood storage devices 20 of the present disclosure, it was observed that by the appropriate selection and design of inlet/outlet 30, tubing 304, tubing 205 and combinations thereof, the necessity to efficiently and continually remove ingressed oxygen could be significantly reduced. The selection of inner collapsible blood containers 202 having a permeability of between 3 and 11 Barrer is provided in devices wherein the ingressed oxygen has been essentially reduced or eliminated. Not to be limited by theory, it is believed that the ingressed oxygen enters the system largely through tubing 205 or its bond 302, which can form gap 209, and is transported to the collapsible blood container 202. In order to maintain the oxygen depleted state of the blood, it needs to be removed by passing out of an oxygen permeable collapsible blood container 202, diffusing through the headspace and binding to oxygen sorbent 207. Accordingly, the materials used to prepare collapsible blood container 202 should be selected to be as permeable as possible. In contrast, when ingressed oxygen can be largely eliminated, the choice of materials suitable for collapsible blood container 202 can include less permeable materials as provided herein.

As used herein, inner collapsible blood containers that are significantly less permeable to oxygen, are collapsible blood container 202 that have a permeability of between 3 and 11 Barrer.

The present disclosure provides for, and includes, a collapsible blood container 202 that is relatively permeable to oxygen and is a membrane 206 prepared from polyvinyl chloride (PVC). In aspects according the present disclosure, the collapsible blood container 202 can be prepared from a PVC membrane 206 having a thickness of between 25 µm and 450 µm, preferably from 50 µm to 400 µm, and more preferably between 150 µm and 400 µm. In some aspects, the collapsible blood container 202 can be prepared from a PVC membrane 206 having a thickness of between 25 µm and 250 µm. In other aspects, the collapsible blood container 202 can be prepared from a PVC membrane 206 having a thickness of between 350 µm and 450 µm. In some aspects, the collapsible blood container 202 is prepared from a PVC membrane 206 having a thickness of 381 µm.

The use of PVC in the manufacture of collapsible blood containers is well known in the art. The use of various plasticizers in various PVC formulations is also well known in the art, and includes the use of diethylhexyl phthalate (DEHP) for long term storage of red blood cells. In addition to increasing the flexibility of the PVC, DEHP also increases the permeability of PVC to oxygen. Accordingly, the present disclosure provides for, and includes, a collapsible blood container 202 comprising PVC doped with DEHP to increase permeability. Typical manufacture of collapsible blood containers from PVC-DEHP utilizes radiofrequency (RF) welding of a pair of films to conveniently fabricate a bag structure, with such individual films having a thickness of 350 µm to 400 µm. An exemplary PVC-DEHP film is the Renolit ES-3000 film (American Renolit Corp., City of Commerce, CA).

Due to the relatively low oxygen permeability of such films and the need for higher oxygen permeability for platelet storage, other plasticizers for PVC have found utility in the fabrication of collapsible blood containers and include the use of citrate, among others (see, for example, "The Role of Poly(Vinyl Chloride) in Healthcare" by Colin R. Blass, copyright 2001 Rapra Technology, Ltd., ISBN: 1-85957-258-8). A suitable example of a PVC-citrate film is the Renolit ES-4000 film (American Renolit Corp., City of Commerce, CA). The plasticity of PVC and the permeability of PVC may also be increased by the inclusion of DINCH, bis(7-methyloctyl) cyclohexane-1,2-dicarboxylate (also identifiable as E.C. Number 431-890-2 and available from BASF as Hexamoll® DINCH). A collapsible blood container 202 of the present disclosure may be comprised of PVC doped with DINCH to increase oxygen permeability. Among the advantages of using citrate or DINCH in a collapsible blood container 202 is that some concerns have been raised regarding the safety of DEHP, even while DEHP improves the storability of red blood cells. Not to be limited by theory, it is believed that deoxygenation of the red blood cells allows for the removal of DEHP from the blood storage system while not compromising the quality and storability of the red blood cells that would otherwise be provided by DEHP.

The present disclosure provides for suitable PVC materials for use in a collapsible blood container 202 that is permeable to oxygen. The use of a PVC-citrate film such as Renolit ES-4000 having a thickness of from 25 µm to 450 µm, preferably from 50 µm to 400 µm, and more preferably from 150 µm to 400 µm is suitable for providing a collapsible blood container having the desired characteristics of relatively high oxygen permeability for PVC membranes, having an oxygen permeability of at least 3 Barrer, and having good RF welding and joining characteristics and high tensile strength. In certain aspects the present disclosure provides for a collapsible blood container 202 prepared from a PVC membrane 206 that is relatively permeable to oxygen having a thickness of from 25 µm to 450 µm, suitable for the continued reduction of oxygen of the blood contained therein over the duration of storage for 42 days, or up to 64 days. In certain aspects the present disclosure provides for a collapsible blood container 202 prepared from a PVC membrane 206 that is relatively permeable to oxygen having a thickness of from 350 µm to 400 µm, suitable for the maintenance of the reduced oxygen level of the blood contained therein over the duration of storage for 42 days, or up to 64 days.

The present disclosure provides for, and includes, a collapsible blood container 202 that is substantially permeable to oxygen and is a membrane 206 prepared from silicone. In aspects according the present disclosure, the collapsible blood container 202 can be prepared from a silicone membrane 206 having a thickness of between 20 µm and 500 µm. In other aspects, the collapsible blood container 202 can have a thickness of between 30 µm and 400 µm. In other aspects, the collapsible blood container 202 can have a thickness of between 30 µm and 200 µm. In another aspect the collapsible blood container 202 is between 50 µm and 150 µm thick. In certain aspects, the present disclosure provides for a collapsible blood container 202 prepared from a silicone membrane 206 that is substantially permeable to oxygen having a thickness of from 50 µm to 150 µm, suitable for the continued reduction of oxygen of the blood contained therein over the duration of storage for 42 days, or up to 64 days.

In aspects according the present disclosure, the collapsible blood container 202 can be prepared from a silicone membrane 206 having a thickness of between 20 μm and 400 μm. In other aspects, the collapsible blood container 202 can have a thickness of between 20 μm and 200 μm. In other aspects, the collapsible blood container 202 can have a thickness of between 40 μm and 300 μm. In another aspect, the collapsible blood container 202 is between 40 μm and 400 μm thick. In yet another aspect, the collapsible blood container 202 is between 300 μm and 450 μm thick. In a further aspect, the thickness of the collapsible blood container 202 can be between 350 μm and 450 μm. The present disclosure provides for, and includes, a collapsible blood container 202 that is 450 μm in thickness. In another aspect, the collapsible blood container 202 is 425 μm thick. In yet another aspect, the collapsible blood container 202 is 400 μm thick. In an additional aspect, the collapsible blood container 202 is 350 μm thick. In certain aspects the present disclosure provides for a collapsible blood container 202 prepared from a silicone membrane 206 that is substantially permeable to oxygen having a thickness of from 350 μm to 500 μm, suitable for the maintenance of the reduced oxygen level of the blood contained therein over the duration of storage for 42 days, or up to 64 days.

Suitable silicone membranes 206 include commercially available membranes. Non-limiting examples of silicone membranes are available from Wacker Silicones, such as the Silpuran® brand of medical grade silicone sheet membranes (Wacker Silicones, Adrian, MI) and Polymer Sciences PS-1033 and PS-1044 P-Derm® silicone elastomer membranes (Polymer Sciences, Inc., Monticello, IN). In an aspect, the silicone membrane may be Polymer Sciences PS-1033 or Silpuran® 6000 silicone. Silicone membranes can be prepared from various liquid silicone rubber (LSR) materials, which are available from a number of silicone suppliers, such as Wacker Silicones (Adrian, MI), Shin-Etsu Silicones of America (Akron, OH), NuSil Technology (Carpenteria, CA), and Blue Star Silicones (East Brunswick, NJ), to name a few.

In an aspect according to the present disclosure, a collapsible blood container 202 can be manufactured from silicone by various molding methods such as compression molding, injection molding, and insert molding, and also adhesive bonding of silicone sheets using silicone adhesives. In one aspect according to the present disclosure, a pair of silicone sheets are bonded together around the periphery with a section of silicone inlet tubing in place in the seam using silicone adhesive. In another aspect according to the present disclosure, a silicone liquid rubber is injection molded over a form to create a three-sided shape, which is then further bonded to closure on the remaining fourth side around a silicone inlet tube using a silicone adhesive. In another aspect according to the present disclosure, a silicone liquid rubber is injection molded over a form to create a three-sided shape, which is then insert molded onto a closure shape on the remaining fourth side that incorporates an inlet tubing into the closure shape. In another aspect according to the present disclosure, a silicone liquid rubber is diluted in a suitable solvent, such as xylene, hexane or tetrahydrofuran, and dip coated over a form to create a three-sided shape, which is then insert molded onto a closure shape on the remaining fourth side that incorporates an inlet tubing into the closure shape.

Mixed Membrane Inner Bags

The present disclosure provides for, and includes, a collapsible blood container 202 that is prepared from more than one type of membrane 206. In an aspect, a collapsible blood container 202 comprises a first membrane 206 and a second different membrane 206 suitably bonded to prepare a container. In another aspect, a collapsible blood container 202 comprises a membrane 206 combined with a second membrane 206 that has a permeability of less than about 30% of the permeability of first membrane 206. In an aspect, the second membrane 206 may comprise a rigid structure joined to an oxygen permeable membrane 206. In aspects according to the present disclosure, the second membrane 206 is heat sealed, laminated or boned to membrane 206.

The present disclosure provides for, and includes, a collapsible blood container 202 that is substantially permeable to oxygen and is a microporous membrane 206 prepared from polytetrafluoroethylene, or polyvinylidene fluoride, also known as polyvinylidene difluoride (PVDF). In certain aspects, the PVDF membrane is a hydrophobic microporous membrane that is substantially permeable to oxygen.

In aspects according to the present disclosure, the microporous PVDF membrane 206 comprises pores having a range of between 0.01 μm and 2.0 μm. In other aspects, the microporous PVDF membrane 206 comprises pores having a range of between 0.01 μm and 1.0 μm. In some aspects, a microporous PVDF membrane 206 has a pore size of between 0.03 μm and 1.0 μm in diameter. In other aspects, a microporous PVDF membrane 206 has a pore size of between 0.03 μm and 0.45 μm in diameter.

In aspects according to the present disclosure, the void fraction of a PVDF membrane 206 used to prepare a collapsible blood container 202 is between 20 and 80%. In another aspect, the void fraction of a PVDF membrane 206 used to prepare a collapsible blood container 202 is between 35 and 50%.

In certain aspects, the permeability of PVDF membranes 206 having micropores greater than about 1.0 μm may allow fluid to permeate through the membrane, compromising both the fluid containment as well as the oxygen and carbon dioxide permeability. To overcome this permeability at high pore sizes, so called "super-hydrophobic" membranes can be employed wherein the contact angle is greater than 150°. As used herein and known in the art, the contact angle quantifies the wettability of a solid surface and is theoretically described by Young's equation. In certain aspects according the present disclosure, the use of non-hydrophobic PVDF materials is not recommended as the surface tension of the material is lower and allows for fluid to seep through the pores even at the ranges stated above.

In certain aspects according to the present disclosure, the collapsible blood container 202 is prepared from a PVDF permeable membrane 206 having a pore size of between 0.1 and 0.8 μm in diameter. In other aspects, micropores of porous PVDF membranes may be from 0.22 to 0.8 μm in diameter. In an aspect, the micropores of porous PVDF membranes are from 0.2 to 1.0 μm. In another aspect, the micropores of porous PVDF membranes may be greater than 0.1 and less than 1.0 μm. In a further aspect, the micropore of the porous PVDF membrane ranges from 0.05 to 1.0 μm. In some aspects, the micropores of porous PVDF membranes may be greater than 0.3 or 0.4 μm. In other aspects, the micropores of porous PVDF membranes may be greater than 0.5 or 0.6 μm.

In aspects according to the present disclosure, a blood storage device 20 comprises an inner collapsible blood container 202 comprising a PVDF membrane 206 having a micropore size of less than 1.0 μm. In another aspect according to the present disclosure, a blood storage device 20 comprises an inner collapsible blood container 202 comprising a PVDF membrane 206 having a micropore size of less than 0.8 µm. In certain aspects according to the present disclosure, a blood storage device 20 comprises an inner collapsible blood container 202 comprising a PVDF membrane 206 having a micropore size of less than 0.65 µm. In another aspect according to the present disclosure, a blood storage device 20 comprises an inner collapsible blood container 202 comprising a PVDF membrane 206 having a micropore size of less than 0.45 µm.

In an aspect according to the present disclosure, a blood storage device 20 comprises an inner collapsible blood container 202 comprising a PVDF membrane 206 having a micropore size of 0.1 µm. In another aspect, a blood storage device 20 comprises an inner collapsible blood container 202 comprising a PVDF membrane 206 having a micropore size of 0.22 µm. In another aspect, a blood storage device 20 comprises an inner collapsible blood container 202 comprising a PVDF membrane 206 having a micropore size of 0.20 µm. In a further aspect according to the present disclosure, a blood storage device 20 comprises an inner collapsible blood container 202 comprising a PVDF membrane 206 having a micropore size of 0.45 µm. In yet a further aspect, a blood storage device 20 comprises an inner collapsible blood container 202 comprising a PVDF membrane 206 having a micropore size of 0.65 µm. In another aspect according to the present disclosure, a blood storage device 20 comprises an inner collapsible blood container 202 comprising a PVDF membrane 206 having a micropore size of 0.8 µm.

In aspects according to the present disclosure, the PVDF membrane may be less than 250 µm thick. In certain aspects, the membrane is greater than 10 µm thick. In some aspects, the PVDF membrane may be between 10 and 250 µm thick. In other aspects, the PVDF membrane may be between 10 and 125 µm thick or between 25 and 150 µm thick. In an aspect, the PVDF membrane may be between 50 and 125 µm thick, 75 and 125 µm thick, 50 and 150 µm thick, 75 and 150 µm thick, 100 and 125 µm thick, 150 and 250 µm thick, or between 25 and 150 µm thick. In an aspect, the membrane 206 of inner collapsible blood container 202 is 20 µm thick. In another aspect, the membrane 206 of inner collapsible blood container 202 is 30 µm thick. In yet another aspect, the membrane 206 of inner collapsible blood container 202 is 50 µm thick. In a further aspect, the membrane 206 of inner collapsible blood container 202 is 76 µm thick. In an aspect, the membrane 206 of inner collapsible blood container 202 is 120 µm thick.

In certain aspects according to the present disclosure, the collapsible blood container 202 is prepared from a PVDF permeable membrane 206 that is between 100 and 125 µm thick. In certain aspects according to the present disclosure, the collapsible blood container 202 is prepared from a PVDF permeable membrane 206 having a pore size of between 0.1 µm and 0.8 µm in diameter and that is between 100 and 125 µm thick. In certain aspects according to the present disclosure, the collapsible blood container 202 is prepared from a PVDF permeable membrane 206 having a pore size of between 0.1 µm and 0.8 µm in diameter and that is between 50 and 150 µm thick.

Examples of suitable PVDF membranes for the preparation of inner collapsible blood containers that are permeable to oxygen according to the present disclosure include VVSP 115 µm thick/0.1 µm pore; GVSP 115 µm thick/0.22 µm pore; HVSP 115 µm thick/0.45 µm pore; DVSP 115 µm thick/0.65 µm pore; BVSP 115 µm thick/1.0 µm pore; VVHP 107 µm thick/0.1 µm pore; GVHP 125 µm thick/0.22 µm pore; HVHP 115 µm thick/0.45 µm pore; or DVHP 115 µm thick/0.65 µm pore.

Suitable PVDF membranes 206 include commercially available membranes. Non-limiting examples of PVDF membranes 206 are available from Millipore Corporation, Bedford, MA In an aspect, the PVDF membrane 206 may be obtained from Millipore Corporation, Bedford, MA An example of such a PVDF membrane 206 is the VVSP, GVSP, HVSP, DVSP, BVSP, VVHP, GVHP, HVHP, or DVHP.

The present disclosure provides for, and includes, a collapsible blood container 202 that is substantially permeable to oxygen and is a microporous membrane 206 prepared from polysulfone. In certain aspects, the polysulfone membrane 206 is a hydrophobic microporous membrane 206 that is substantially permeable to oxygen.

In aspects according to the present disclosure, the microporous polysulfone membrane 206 comprises pores having a range of between 0.01 µm and 2.0 µm. In other aspects, the microporous polysulfone membrane 206 comprises pores having a range of between 0.01 µm and 1.0 µm. In some aspects, a microporous polysulfone membrane 206 has a pore size of between 0.03 µm and 1.0 µm in diameter. In other aspects, a microporous polysulfone membrane 206 has a pore size of between 0.03 µm and 0.45 µm in diameter.

In aspects according to the present disclosure, the void fraction of a polysulfone membrane 206 used to prepare a collapsible blood container 202 is between 20 and 80%. In another aspect, the void fraction of a polysulfone membrane 206 used to prepare a collapsible blood container 202 is between 35 and 50%.

In certain aspects, the permeability polysulfone membranes having micropores greater than about 0.2 µm may allow fluid to permeate through the membrane, compromising both the fluid containment and the oxygen and carbon dioxide permeability. To overcome this permeability at high pore sizes, so called "super-hydrophobic" membranes can be employed wherein the contact angle is greater than 150°. As used herein and known in the art, the contact angle quantifies the wettability of a solid surface and is theoretically described by Young's equation. In certain aspects according the present disclosure, the use of non-hydrophobic polysulfone materials is not recommended as the surface tension of the material is lower and allows for fluid to seep through the pores even at the ranges stated above.

In certain aspects according to the present disclosure, the collapsible blood container 202 is prepared from a polysulfone permeable membrane 206 having a pore size of between 0.03 µm and 0.8 µm in diameter. In other aspects, micropores of porous polysulfone membranes may be from 0.22 µm to 0.8 µm in diameter. In an aspect, the micropores of porous polysulfone membranes are from 0.2 µm to 1.0 µm. In another aspect, the micropores of porous polysulfone membranes may be greater than 0.1 µm and less than 1.0 µm. In a further aspect, the micropore of the porous polysulfone membrane ranges from 0.05 µm to 1.0 µm. In some aspects, the micropores of porous polysulfone membranes may be greater than 0.3 µm or 0.4 µm. In other aspects, the micropores of porous polysulfone membranes may be greater than 0.5 µm or 0.6 µm.

In aspects according to the present disclosure, a blood storage device 20 comprises an inner collapsible blood container 202 comprising a polysulfone membrane 206 having a micropore size of less than 1.0 µm. In another aspect according to the present disclosure, a blood storage device 20 comprises an inner collapsible blood container 202 comprising a polysulfone membrane 206 having a micropore size of less than 0.8 µm. In certain aspects according to the present disclosure, a blood storage device 20 comprises an inner collapsible blood container 202 comprising a polysulfone membrane 206 having a micropore size of less than 0.65 µm. In another aspect according to the present disclosure, a blood storage device 20 comprises an inner collapsible blood container 202 comprising a polysulfone membrane 206 having a micropore size of less than 0.45 µm.

In an aspect according to the present disclosure, a blood storage device 20 comprises an inner collapsible blood container 202 comprising a polysulfone membrane 206 having a micropore size of 0.1 µm. In another aspect, a blood storage device 20 comprises an inner collapsible blood container 202 comprising a polysulfone membrane 206 having a micropore size of 0.22 µm. In another aspect, a blood storage device 20 comprises an inner collapsible blood container 202 comprising a polysulfone membrane 206 having a micropore size of 0.20 µm. In a further aspect according to the present disclosure, a blood storage device 20 comprises an inner collapsible blood container 202 comprising a polysulfone membrane 206 having a micropore size of 0.45 µm. In yet a further aspect, a blood storage device 20 comprises an inner collapsible blood container 202 comprising a polysulfone membrane 206 having a micropore size of 0.65 µm. In another aspect according to the present disclosure, a blood storage device 20 comprises an inner collapsible blood container 202 comprising a polysulfone membrane 206 having a micropore size of 0.8 µm. In another aspect according to the present disclosure, a blood storage device 20 comprises an inner collapsible blood container 202 comprising a polysulfone membrane 206 having a micropore size of 0.03 µm. In another aspect according to the present disclosure, a blood storage device 20 comprises an inner collapsible blood container 202 comprising a polysulfone membrane 206 having a micropore size of 0.05 µm. In another aspect according to the present disclosure, a blood storage device 20 comprises an inner collapsible blood container 202 comprising a polysulfone membrane 206 having a micropore size of 1.2 µm.

In aspects according to the present disclosure, the polysulfone membrane may be less than 250 µm thick. In certain aspects, the membrane is greater than 10 µm thick. In some aspects, the polysulfone membrane may be between 10 and 250 µm thick. In other aspects, the polysulfone membrane may be between 10 and 125 µm thick or 25 and 150 µm thick. In an aspect, the polysulfone membrane may be between 50 and 125 µm thick, 75 and 125 µm thick, 50 and 150 µm thick, 75 and 150 µm thick, 100 and 125 µm thick, 150 and 250 µm thick, or between 25 and 150 µm thick. In an aspect, the membrane 206 of inner collapsible blood container 202 is 20 µm thick. In another aspect, the membrane 206 of inner collapsible blood container 202 is 30 µm thick. In yet another aspect, the membrane 206 of inner collapsible blood container 202 is 50 µm thick. In a further aspect, the membrane 206 of inner collapsible blood container 202 is 76 µm thick. In an aspect, the membrane 206 of inner collapsible blood container 202 is 120 µm thick.

In certain aspects according to the present disclosure, the collapsible blood container 202 is prepared from a polysulfone permeable membrane 206 that is between 100 and 125 µm thick. In certain aspects according to the present disclosure, the collapsible blood container 202 is prepared from a polysulfone permeable membrane 206 having a pore size of between 0.1 µm and 0.8 µm in diameter and that is between 100 and 125 µm thick. In certain aspects according to the present disclosure, the collapsible blood container 202 is prepared from a polysulfone permeable membrane 206 having a pore size of between 0.1 µm and 0.8 µm in diameter and that is between 50 and 150 µm thick.

Examples of suitable polysulfone membranes 206 for the preparation of inner collapsible blood containers that are permeable to oxygen according to the present disclosure include SS003AH 10-250 µm thick/0.03 µm pore; SS005AH 10-250 µm thick/0.05 µm pore; SS010AH 10-250 µm thick/0.1 µm pore; SS020AH 10-250 µm thick/0.2 µm pore; SS045AH 10-250 µm thick/0.45 µm pore; SS065AH 10-250 µm thick/0.65 µm pore; SS080AH 10-250 µm thick/0.8 µm pore; or SS120AH 10-250 µm thick/1.2 µm pore.

Suitable polysulfone membranes 206 include commercially available membranes. Non-limiting examples of polysulfone membranes 206 are available from Pacific Membranes. In an aspect, the polysulfone membrane may be SS120AH, SS080AH, SS065AH, SS045AH, SS020AH, SS010AH, SS005AH, or SS003AH.

The present disclosure provides for, and includes, a collapsible blood container 202 that is substantially permeable to oxygen and is a microporous membrane 206 prepared from polyolefin. The present disclosure also provides for, and includes, a collapsible blood container 202 that is impermeable to oxygen prepared from a polyolefin film. In certain aspects, the polyolefin membrane is a hydrophobic microporous membrane that is substantially permeable to oxygen. Examples of oxygen permeable polyolefin membranes 206 suitable for use in the preparation of a collapsible blood container 202 include Membrana Accurel® PP flat sheet membranes (Membrana division of Celgard, LLC, Charlotte, NC), PP flat sheet membranes from Sterlitech (Kent, WA), Metricel® PP hydrophobic filter membranes (Pall Corp., Port Washington, NY), Propafilm™ RGP, RF and RGN series of biaxially oriented polypropylene (BOPP) films from Innovia (Innovia Films, Inc., Atlanta, GA). In certain aspects, the polyolefin membrane is a biaxially oriented polypropylene (BOPP) film that is substantially permeable to oxygen. Examples of suitable polyolefin films include the Propafilm™ RGP, RF and RGN series of biaxially oriented polypropylene (BOPP) coextruded films from Innovia (Innovia Films, Inc., Atlanta, GA), having an oxygen permeability of 140 to 450 Barrer.

In aspects according to the present disclosure, the microporous polyolefin membrane 206 comprises pores having a range of between 0.01 µm and 2.0 µm. In other aspects, the microporous polyolefin membrane 206 comprises pores having a range of between 0.01 µm and 1.0 µm. In some aspects, a microporous polyolefin membrane 206 has a pore size of between 0.03 µm and 1.0 µm in diameter. In other aspects, a microporous polyolefin membrane 206 has a pore size of between 0.1 µm and 0.45 µm in diameter.

In certain aspects according to the present disclosure, the use of non-hydrophobic polyolefin materials is not recommended as the surface tension of the material is lower and allows for fluid to seep through the pores even at the ranges stated above.

In certain aspects according to the present disclosure, the collapsible blood container 202 is prepared from a polyolefin permeable membrane 206 having a pore size of between 0.1 µm and 0.45 µm in diameter. In other aspects, micropores of porous polyolefin membranes may be from 0.1 µm to 0.2 µm in diameter.

In aspects according to the present disclosure, a blood storage device 20 comprises an inner collapsible blood container 202 comprising a polyolefin membrane 206 having a micropore size of less than 1.0 µm. In another aspect according to the present disclosure, a blood storage device 20 comprises an inner collapsible blood container 202 comprising a polyolefin membrane 206 having a micropore size of less than 0.5 μm. In certain aspects according to the present disclosure, a blood storage device 20 comprises an inner collapsible blood container 202 comprising a polyolefin membrane 206 having a micropore size of less than 0.2 μm.

In an aspect according to the present disclosure, a blood storage device 20 comprises an inner collapsible blood container 202 comprising a polyolefin membrane 206 having a micropore size of 0.1 μm. In another aspect, a blood storage device 20 comprises an inner collapsible blood container 202 comprising a polyolefin membrane 206 having a micropore size of 0.2 μm. In a further aspect according to the present disclosure, a blood storage device 20 comprises an inner collapsible blood container 202 comprising a polyolefin membrane 206 having a micropore size of 0.45 μm.

In aspects according to the present disclosure, the polyolefin membrane may be less than 250 μm thick. In certain aspects, the membrane is greater than 50 μm thick. In some aspects, the polyolefin membrane may be between 50 and 250 μm thick. In other aspects, the polyolefin membrane may be between 75 and 110 μm thick or between 140 and 180 μm thick.

In certain aspects according to the present disclosure, the collapsible blood container 202 is prepared from a polyolefin permeable membrane 206 that is between 50 and 250 μm thick. In certain aspects according to the present disclosure, the collapsible blood container 202 is prepared from a polyolefin permeable membrane 206 having a pore size of between 0.1 μm and 0.45 μm in diameter and that is between 75 μm and 200 μm thick. In certain aspects according to the present disclosure, the collapsible blood container 202 is prepared from a polyolefin permeable membrane 206 having a pore size of between 0.1 μm and 0.2 μm in diameter and that is between 75 μm and 200 μm thick. In certain aspects according to the present disclosure, the collapsible blood container 202 is prepared from a polyolefin permeable membrane 206 having a pore size of between 0.2 μm and 0.45 μm in diameter and that is between 140 μm and 200 μm thick.

Examples of suitable polyolefin membranes for the preparation of inner collapsible blood containers that are permeable to oxygen according to the present disclosure include those described in U.S. Pat. No. 4,440,815 issued to Zomorodi et al., Membrana Accurel® PP flat sheet membranes (Membrana division of Celgard, LLC, Charlotte, NC), PP flat sheet membranes from Sterlitech (Kent, WA), Metricel® PP hydrophobic filter membranes (Pall Corp., Port Washington, NY), Propafilm™ RGP, RF and RGN series of biaxially oriented polypropylene (BOPP) films from Innovia (Innovia Films, Inc., Atlanta, GA).

In certain aspects, suitable membranes 206 that are substantially permeable to oxygen may be multilayered membranes. In certain aspects, the multilayered membranes are hydrophobic microporous membranes that are substantially permeable to oxygen. Suitable multilayered membranes 206 include multilayered membranes having two or more materials selected from the group consisting of PVDF rendered hydrophobic, PTFE, nylon, cellulose esters, polysulfone, polyethersulfone, polypropylene rendered hydrophobic, and polyacrylonitrile.

The present disclosure provides for, and includes, a collapsible blood container 202 that is substantially permeable to oxygen and is a microporous membrane 206 prepared from an extruded, woven, non-woven single layer or multilayered membrane. In certain aspects, the multilayered membrane is a hydrophobic microporous membrane that is substantially permeable to oxygen.

In aspects according to the present disclosure, the microporous multilayered membrane comprises pores having a range of between 0.01 μm and 2.0 μm. In other aspects, the microporous multilayered membrane 206 comprises pores having a range of between 0.01 μm and 1.0 μm. In some aspects, a microporous multilayered membrane 206 has a pore size of between 0.03 μm and 1.0 μm in diameter. In other aspects, a microporous multilayered membrane 206 has a pore size of between 0.03 μm and 0.45 μm in diameter.

In aspects according to the present disclosure, the void fraction of a multilayered membrane 206 used to prepare a collapsible blood container 202 is between 20 and 80%. In another aspect, the void fraction of a multilayered membrane 206 used to prepare a collapsible blood container 202 is between 35 and 50%.

In certain aspects, the permeability of multilayered membranes having micropores greater than about 1.0 μm may allow fluid to permeate through the membrane, compromising both the fluid containment and the oxygen and carbon dioxide permeability. To overcome this permeability at high pore sizes, so called "super-hydrophobic" membranes can be employed wherein the contact angle is greater than 150°. As used herein and known in the art, the contact angle quantifies the wettability of a solid surface and is theoretically described by Young's equation. In certain aspects according the present disclosure, the use of non-hydrophobic multilayered materials is not recommended as the surface tension of the material is lower and allows for fluid to seep through the pores even at the ranges stated above.

In certain aspects according to the present disclosure, the collapsible blood container 202 is prepared from a multilayered permeable membrane 206 having a pore size of between 0.1 μm and 0.8 μm in diameter. In other aspects, micropores of porous multilayered membranes may be from 0.22 μm to 0.8 μm in diameter. In an aspect, the micropores of porous multilayered membranes are from 0.2 μm to 1.0 μm. In another aspect, the micropores of porous multilayered membranes may be greater than 0.1 μm and less than 1.0 μm. In a further aspect, the micropore of the porous multilayered membrane ranges from 0.05 μm to 1.0 μm. In some aspects, the micropores of porous multilayered membranes may be greater than 0.3 or 0.4 μm. In other aspects, the micropores of porous multilayered membranes may be greater than 0.5 or 0.6 μm.

In aspects according to the present disclosure, a blood storage device 20 comprises an inner collapsible blood container 202 comprising a multilayered membrane 206 having a micropore size of less than 1.0 μm. In another aspect according to the present disclosure, a blood storage device 20 comprises an inner collapsible blood container 202 comprising a multilayered membrane 206 having a micropore size of less than 0.8 μm. In certain aspects according to the present disclosure, a blood storage device 20 comprises an inner collapsible blood container 202 comprising a multilayered membrane 206 having a micropore size of less than 0.65 μm. In another aspect according to the present disclosure, a blood storage device 20 comprises an inner collapsible blood container 202 comprising a multilayered membrane 206 having a micropore size of less than 0.45 μm.

In an aspect according to the present disclosure, a blood storage device 20 comprises an inner collapsible blood container 202 comprising a multilayered membrane 206 having a micropore size of 0.1 μm. In another aspect, a blood storage device 20 comprises an inner collapsible blood container 202 comprising a multilayered membrane 206 having a micropore size of 0.22 µm. In another aspect, a blood storage device 20 comprises an inner collapsible blood container 202 comprising a multilayered membrane 206 having a micropore size of 0.20 µm. In a further aspect according to the present disclosure, a blood storage device 20 comprises an inner collapsible blood container 202 comprising a multilayered membrane 206 having a micropore size of 0.45 µm. In yet a further aspect, a blood storage device 20 comprises an inner collapsible blood container 202 comprising a multilayered membrane 206 having a micropore size of 0.65 µm. In another aspect according to the present disclosure, a blood storage device 20 comprises an inner collapsible blood container 202 comprising a multilayered membrane 206 having a micropore size of 0.8 µm.

In aspects according to the present disclosure, the multilayered membrane 206 may be less than 250 µm thick. In certain aspects, the membrane is greater than 10 µm thick. In some aspects the multilayered membrane 206 may be between 10 and 250 µm thick. In other aspects, the multilayered membrane may be between 10 and 125 µm thick or 25 and 150 µm thick. In an aspect, the multilayered membrane 206 may be between 50 and 125 µm thick, 75 and 125 µm thick, 50 and 150 µm thick, 75 and 150 µm thick, 100 and 125 µm thick, 150 and 250 µm thick or between 25 and 150 µm thick, 100 and 125 µm thick, 150 and 250 µm thick or between 25 and 150 µm thick. In another aspect, the membrane 206 of inner collapsible blood container 202 is 30 µm. In yet another aspect, the membrane 206 of inner collapsible blood container 202 is 50 µm. In a further aspect, the membrane 206 of inner collapsible blood container 202 is 76 µm. In an aspect, the membrane 206 of inner collapsible blood container 202 is 120 µm thick In certain aspects according to the present disclosure, the collapsible blood container 202 is prepared from a multilayered permeable membrane 206 that is between 100 and 125 µm thick. In certain aspects according to the present disclosure, the collapsible blood container 202 is prepared from a multilayered permeable membrane 206 having a pore size of between 0.1 µm and 0.8 µm in diameter and that is between 100 µm and 125 µm thick. In certain aspects according to the present disclosure, the collapsible blood container 202 is prepared from a multilayered permeable membrane 206 having a pore size of between 0.1 µm and 0.8 µm in diameter and that is between 50 µm and 150 µm thick.

The present disclosure provides for, and includes, a collapsible blood container 202 having resistance to tearing. As used herein, "tear resistance" or "tear strength" is measured in kN/m. In aspects according the present disclosure, the collapsible blood container 202 should be prepared from oxygen permeable materials that are also resistant to tearing. Measures of tear resistance are known in the art, for example, ASTM D-412, which can also be used to measure tensile strength, modulus, and elongations. In certain aspects, collapsible blood container 202 should be prepared from oxygen permeable materials that are resistant to the formation of a tear (e.g., tear initiation). Methods of measuring tear initiation and tear propagation are known in the art, for example, ASTM D-624. Other methods include measuring the tensile strength and the elongation at break according to DIN 53 504-S1.

In an aspect according to the present disclosure, a collapsible blood container 202 should be prepared from oxygen permeable materials having a tear strength of at least 10 N/mm according to test method ASTM D-1004. In an aspect, the tear strength is at least 25 N/mm. In some aspects, the tear strength is at least 50 N/mm. In some aspects, the tear strength is at least 100 N/mm. The blood storage devices 20 further provide for, and include, collapsible blood containers 202 prepared from materials having a tear strength of between 10 to 100 N/mm. In aspects of the present disclosure, a reduced tear strength is provided for collapsible blood containers 202 wherein the outer receptacle 201 has a tear strength of at least 50 N/mm. Generally, the tear strength of a collapsible blood container 202 decreases with increasing permeability. It will be appreciated by those of skill in the art, that materials are to be selected to maintain the overall integrity of the blood storage device 20 so that the potentially biohazardous blood materials are contained should the device 20 be mishandled during processing (e.g., dropped or crushed).

The present disclosure includes and provides for a blood storage device 20 having an inner collapsible blood container 202 and further including one or more spacers 213 that ensure the separation of the outer receptacle 201 and the inner collapsible blood container 202. The spacer 213 provides for the maintenance of the headspace in the blood storage device 20 to ensure efficient diffusion of the oxygen to the sorbent 207. A spacer 213 can be prepared from one or more of the materials selected from the group consisting of a mesh, a molded mat, a woven mat, a non-woven mat, a strand veil, and a strand mat. In certain aspects, the spacer 213 can be integrated directly into the collapsible blood container 202 as ribs, dimples, or other raised feature that maintains a separation between the outer receptacle 201 and the inner collapsible blood container 202. The present specification also includes and provides for a spacer 213 to be integrated into the outer receptacle 201 as ribs, dimples, or other suitable raised feature capable of maintaining a separation between the outer receptacle 201 and the inner collapsible blood container 102. In certain aspects, the presence of spacer 213 provides consistency to the assembly from a standpoint of manufacturing technique and layering of the inner and outer films allowing for repeatable oxygen level maintenance. In other aspects, the presence of spacer 213 facilitates further oxygen reduction for during a storage period. By providing a spacer 213, an inner membrane 206 can be prevented from become laminated or "stuck to" the membrane or material of outer receptacle 201 via mechanical or physical means. Not to be limited by theory, it is thought that if sticking or lamination were to occur, the oxygen preservation or further oxygen reduction of the assembly may be compromised as the oxygen encounters additional barriers to diffusion.

In certain aspects, the spacer 213 can also provide for a protective surrounding layer around the collapsible blood container 202, increasing the resistance to burst fracture of the collapsible blood container, such as when inadvertently dropped or subjected to other traumatic forces in handling. In an aspect, a spacer 213 providing a protective layer includes an open cell reticulated polyurethane foam as the spacer 213 material. Such spacer 213 material can have from about 10 pores per inch (ppi) to about 100 ppi. In an aspect, the spacer 213 has 45 ppi with a height of 3.2 mm (0.125 in).

In addition to the pores, a spacer 213 providing a protective layer has a height from about 3.2 mm (0.125 in) to about 12.8 (0.5 in). In another aspect the spacer 213 has a height of about 6.4 mm (0.25 in). In another aspect the spacer 213 has a height from about 1.5 mm (0.064 in) to about 12.8 mm (0.50 in). In another aspect, spacer 213 has a height from about 1.2 mm (0.05 in) to about 10 mm (0.4 in). In another aspect, spacer 213 has a height from about 1.2 mm (0.05 in) to about 12.8 mm (0.5 in).

The present disclosure provides for and includes blood storage devices 20 for storing oxygen depleted blood comprising an outer receptacle 201, a collapsible blood container 202, at least one inlet/outlet 30, and an oxygen sorbent 207 situated within said outer receptacle 201. In certain aspects, the oxygen sorbent 207 is situated between outer receptacle 201 and the collapsible blood container 202. In other aspects, the oxygen sorbent is located within the collapsible blood container 202 and contained in a second blood compatible container. In yet other aspects, the oxygen sorbent 207 is situated as a layer in a multilayered membrane, wherein the outer layer is outer receptacle 201 and the innermost layer is collapsible blood container 202.

The present disclosure provides for, and includes, sorbents 207 capable of binding to and removing oxygen from an environment. Unless provided otherwise, the term "sorbent" refers to oxygen sorbents and scavengers. As used herein, "oxygen scavenger" or "oxygen sorbent" is a material that binds irreversibly to or combines with $O_2$ under the conditions of use. The term "oxygen sorbent" may be used interchangeably herein with "oxygen scavenger." In certain aspects according the present disclosure, a material may bind to or combines with oxygen irreversibly. In other aspects, oxygen may bind to a sorbent material and have a very slow rate of release, $k_{off}$. In an aspect, the oxygen may chemically react with some component of the material and be converted into another compound. Any material where the off-rate of bound oxygen is much less than the residence time of the blood can serve as an oxygen scavenger.

As used herein, the amount of sorbent is provided as having a certain binding capacity of oxygen as measured by volume (e.g., cubic centimeters (cc) or milliliters (ml)) at standard temperature and pressure (e.g., 0° C. (273.15 Kelvin) and $1.01 \times 10^5$ pa (100 kPa, 1 bar, 0.986 atm, 760 mmHg) of pressure). In other aspects, oxygen sorbents and scavengers are further capable of binding to and removing carbon dioxide from an environment. In certain aspects, sorbent 103 may be a mixture of non-toxic inorganic and/or organic salts and ferrous iron or other materials with high reactivity toward oxygen, carbon dioxide, or oxygen and carbon dioxide. In certain aspects, an oxygen sorbent or scavenger is combined with a carbon dioxide sorbent. In other aspects, the presence or absence of carbon dioxide binding capabilities of an oxygen sorbent is not necessary.

Suitable oxygen sorbents or scavengers are known in the art. Suitable oxygen sorbents according to the present disclosure have minimum oxygen adsorption rates of 0.8 ml/min. Sorbents having suitable adsorption profiles bind at least 45 ml $O_2$ within 60 minutes, 70 ml $O_2$ within 120 minutes, and 80 ml $O_2$ within 180 minutes. Suitable sorbents may have both higher capacity and binding rates.

Non-limiting examples of oxygen scavengers or sorbents include iron powders and organic compounds. Examples of $O_2$ sorbents include chelates of cobalt, iron, and Schiff bases. Additional non-limiting examples for 02 sorbents may be found in U.S. Pat. No. 7,347,887 issued to Bulow et al., U.S. Pat. No. 5,208,335, issued to Ramprasad et al., and U.S. Pat. No. 4,654,053 issued to Sievers et al., U.S. Pat. No. 4,366, 179 issued to Nawata et al.; each of which is hereby incorporated by reference in their entireties. Oxygen sorbent materials may be formed into or incorporated in fibers, microfibers, microspheres, microparticles, and foams.

In certain aspects, suitable sorbents include those obtainable from Multisorb Technologies (Buffalo, NY), Sorbent Systems/Impak Corporation (Los Angeles, CA), Dessicare, Inc. (Reno, NV) or Mitsubishi Gas Chemical America (MGC) (New York, NY). Exemplary oxygen sorbents include iron-based oxygen scavengers, such as Multisorb Technologies StabilOx® packets, Sorbent Systems P/N SF100PK100 100 cc oxygen absorber, and Mitsubishi Gas Chemical America (MGC) Ageless® SS-200 oxygen absorber. MGC also provides sorbents suitable for the methods and devices of the present disclosure. Such suitable oxygen sorbents include the MGC Ageless® SS-200 oxygen absorber.

In aspects according to the present disclosure, a sorbent may be an oxidizable organic polymer having a polymeric backbone and a plurality of pendant groups. Examples of sorbents with a polymeric backbone include a saturated hydrocarbon (<0.01% carbon-carbon double bonds). In some aspects, the backbone can contain monomers of ethylene or styrene. In an aspect, a polymeric backbone may be ethylenic. In another aspect, an oxidizable organic compound may be ethylene/vinyl cyclohexene copolymer (EVCH). Additional examples of substituted moieties and catalysts are provided in U.S. Patent Publication No. 2003/0183801 by Yang et al., hereby incorporated by reference in its entirety. In additional aspects, an oxidizable organic polymer can also comprise substituted hydrocarbon moieties. Examples of oxygen scavenging polymers include those described by Ching et al., International Patent Publication WO 99/48963, hereby incorporated by reference in its entirety. Oxygen scavenging materials may include those provided in U.S. Pat. No. 7,754,798 issued to Ebner et al., U.S. Pat. No. 7,452,601 issued to Ebner et al., or U.S. Pat. No. 6,387,461 issued to Ebner et al., each of which is hereby incorporated by reference in its entirety.

As used herein, sorbents of the present disclosure may be either free or contained in a permeable enclosure, container, envelope, etc. In certain aspects, sorbent is provided in one or more sachets made of materials having high porosity and essentially no resistance to the transport of gases. Examples of such materials include spun polyester films, perforated metallic foils, spun polyethylene films (Tyvek®), perforated foils, polymers, paper, and combinations thereof.

The present disclosure further includes, and provides for, sorbent 207 incorporated as one or more laminated layers of an outer receptacle 201 substantially impermeable to oxygen. Polymeric sorbents such as those described above may be laminated to sheets used to prepare an outer receptacle using methods known in the art, including soft contact lamination, thermal lamination, or solvent lamination.

The present disclosure further includes, and provides for, sorbents 207 formed inside the pores of porous micro-glass fibers or encapsulated in other inert materials. The encapsulation of transition-metal complexes within the pores of a porous material may be achieved by using a ship-in-a-bottle synthesis in which the final molecule is prepared inside the pores by reacting smaller precursors. Examples of such encapsulated sorbents are known in the art, for example, as described by Kuraoka et al., "Ship-in-a-bottle synthesis of a cobalt phthalocyanine/porous glass composite membrane for oxygen separation," *Journal of Membrane Science,* 286(1-2):12-14 (2006), herein incorporated by reference in its entirety. In some aspects, porous glass fibers may be manufactured as provided in U.S. Pat. No. 4,748,121 issued to Beaver et al., herein incorporated by reference in its entirety. In another aspect, a sorbent can formed as a porous sheet product using papermaking/non-woven wet-laid equipment. Sheets with $O_2$ scavenging formulations may be as described in U.S. Pat. No. 4,769,175 issued to Inoue, herein incorporated by reference in its entirety, which can be formed and then encapsulated with a silicone film.

The present disclosure provides for, and includes, a suitable amount of sorbent 207 sufficient to absorb and retain residual oxygen present after manufacture, ingressed oxygen ingressed during storage of the device 20 and prior to use, oxygen introduced during filling of device 20, residual oxygen contained in the oxygen depleted blood, and oxygen that ingresses during the blood storage period. Prior anaerobic blood storage devices, such as those described by Bitensky, do not recognize nor address the problem of oxygen ingress, particularly through the transfer tubing and collection tubing. Traditional inlets and outlets fail to provide a sufficient oxygen barrier. Moreover, while the present disclosure provides for certain elements that minimize, or even largely eliminate oxygen ingress, absolute impermeability is not practicable. Accordingly, the blood storage devices 20 of the present disclosure incorporate sorbent 207 having both sufficient capacity and appropriate binding kinetics to ensure that the anaerobic environment is maintained. In addition, in certain aspects, sorbent 207 may be further provided to further reduce the level of oxygen in oxygen depleted blood. Finally, the amount of sorbent 207 must also provide for a reliable and reproducible shelf life of blood storage devices 20.

In aspects according to the present disclosure, a blood storage device 20 has an amount of oxygen sorbent 207 having an oxygen binding capacity of at least 20 cc oxygen. In an aspect, the oxygen binding capacity of sorbent 207 in a blood storage device 20 is at least 30 cc oxygen. In an aspect, the oxygen binding capacity of sorbent 207 in a blood storage device 20 is at least 50 cc oxygen. In an aspect, the oxygen binding capacity of sorbent 207 in a blood storage device 20 is at least 100 cc oxygen. In another aspect, the oxygen binding capacity of sorbent 207 is at least 25 or 30 cc oxygen. In yet further aspects, the oxygen binding capacity of sorbent 207 is at least 30 or 45 cc oxygen.

In aspects according to the present disclosure, the oxygen capacity of sorbent 207 is at least 20 cc. In an aspect, the oxygen capacity of sorbent 207 is at least 20 cc but less than 100 cc. In an aspect, the oxygen capacity of sorbent 207 is at least 20 cc but less than 75 cc. In an aspect, the oxygen capacity of sorbent 207 is at least 30 cc but less than 50 cc. In an aspect, the oxygen capacity of sorbent 207 is at least 20 cc but less than 250 cc. In certain aspects, the oxygen capacity of sorbent 207 is between 50 and 200 cc. In other aspects, the oxygen capacity of sorbent 207 is between 100 and 200 cc. In other aspects, the oxygen capacity of sorbent 207 is between 20 and 50 cc.

In other aspects according to the present disclosure, the oxygen capacity of sorbent 207 may be little as 6 cc. In certain aspects, the oxygen capacity of sorbent 207 is between 6 cc and 20 cc. In other aspects, the oxygen capacity of sorbent 207 is about 6 cc. In an aspect, the oxygen capacity of sorbent 207 is between 6 and 10 cc. In another aspect, the oxygen capacity of sorbent 207 is 10 cc. The present disclosure provides for, and includes, an oxygen sorbent 207 having a suitable capacity and suitable rate of oxygen binding to maintain oxygen depleted blood in its depleted state and ensure an appropriate shelf life of blood storage device 20. In aspects according to the present disclosure, sorbent 207 has a minimal oxygen absorption rate of at least 11 cc/week/gram. In another aspect, sorbent 207, having an oxygen absorption rate of at least 11 cc/week/gram and can bind at least 22 cc of oxygen within 2 weeks. In an aspect, sorbent 207, having an oxygen absorption rate of at least 11 cc/week/gram and can bind at least 54 cc of oxygen within 4 weeks. In yet another aspect, sorbent 207, having an oxygen absorption rate of at least 11 cc/week/gram and can bind at least 99 cc of oxygen within 9 weeks.

As used herein, "carbon dioxide scavenger" is a material that binds to or combines with carbon dioxide under the conditions of use. The term "carbon dioxide sorbent" may be used interchangeably herein with "carbon dioxide scavenger." In certain aspects, carbon dioxide sorbents may be non-reactive, or minimally reactive with oxygen. In other aspects, oxygen sorbents may exhibit a secondary functionality of carbon dioxide scavenging. Carbon dioxide scavengers include metal oxides and metal hydroxides. Metal oxides react with water to produce metal hydroxides. The metal hydroxide reacts with carbon dioxide to form water and a metal carbonate. In certain aspects according the present disclosure, a material may bind to or combine with $CO_2$ irreversibly. In aspects according to the present disclosure, a material may bind $CO_2$ with higher affinity than hemoglobin. In other aspects, a sorbent material may bind $CO_2$ with high affinity such that the carbonic acid present in the blood or RBC cytoplasm is released and absorbed by the sorbent. In other aspects, $CO_2$ binds to a sorbent material and has a very slow rate of release, $k_{off}$. In an aspect, the carbon dioxide can chemically react with some component of the material and be converted into another compound.

Carbon dioxide scavengers are known in the art. In certain aspects according to the present disclosure, a carbon dioxide scavenger may be calcium oxide. Reaction of calcium oxide with water produces calcium hydroxide that may react with carbon dioxide to form calcium carbonate and water. In certain aspects according the present disclosure, the water for the production of calcium hydroxide is obtained via diffusion of blood derived water vapor through the inner oxygen permeable container. In another aspect, the water may be provided by the environment through the outer receptacle that is substantially impermeable to oxygen. In yet another aspect, the water may be included with the outer receptacle of the oxygen depletion device.

Non-limiting examples of $CO_2$ scavengers include oxygen scavengers and carbon dioxide scavengers provided by Multisorb Technologies (Buffalo, NY) and Sodasorb® from Grace. Oxygen scavengers may exhibit a secondary functionality of carbon dioxide scavenging.

In aspects according to the present disclosure, $O_2$ depletion media and $CO_2$ depletion media may be blended to a desired ratio to achieve desired results. In another aspect, the sorbent chemistry may have an affinity to both $O_2$ and $CO_2$.

The present disclosure further includes and provides for sorbents contained in sachets. As used herein, a "sachet" is any enclosure that encloses and contains an oxygen sorbent, a carbon dioxide sorbent, or a combination of oxygen and carbon dioxide sorbent(s). Sachets according the present disclosure are contained within overwrap material that is both oxygen and carbon dioxide permeable. In certain aspects, the overwrap material may be a combination of two or more materials, at least one of the materials being oxygen and carbon dioxide permeable. Suitable overwrap materials have a known biocompatible profile or meet ISO 10993.

Sachets are sealed so that the sorbent contents are wholly contained within the overwrap material and do not allow the sorbent to leak, leach, migrate, or otherwise exit its overwrap package. Sachets may take any shape, though typically take a rectangular or square shape. In an aspect, the sachet is about 50×60 mm. In an aspect, the oxygen sorbent 207 binds 20 cc oxygen per sachet at STP. In an aspect, the oxygen sorbent 207 binds 10 cc oxygen per sachet at STP. In an aspect, the oxygen sorbent 207 binds 25 cc oxygen per sachet at STP. In an aspect, the oxygen sorbent 207 binds from 10 to 50 cc oxygen per sachet at STP. In an aspect, the oxygen sorbent 207 binds from 10 to 75 cc oxygen per sachet at STP. In an aspect, the oxygen sorbent 207 binds from 10 to 20 cc oxygen per sachet at STP. In certain aspects according to the present disclosure, a sachet has a total oxygen adsorption capacity of 50 cc $O_2$ at STP. In certain other aspects of the present disclosure, a sachet has a total oxygen absorption capacity of at least 100 cc $O_2$ at STP.

In aspects according to the present disclosure, the oxygen sorbent 207 may be provided in one or more sachets. In another aspect, the oxygen sorbent 207 is provide in a single larger sachet. In other aspects, the oxygen sorbent 207 is provided in two sachets distributed within the headspace between the inner collapsible container 202 and the outer receptacle 201. In yet other aspects, the oxygen sorbent 207 is provided in four sachets distributed within the headspace between the inner collapsible container 202 and the outer receptacle 201. In aspects according to the present disclosure, a blood storage device 20 may comprise 2 to 20 sorbent packages.

In aspects according to the present disclosure, a blood storage device 20 includes from 0.5 to 150 grams of sorbent 207 contained in one or more sachets. Suitable sorbents are provided above. In an aspect, a blood storage device 20 includes from 0.5 to 5 grams of sorbent 207 contained in one or more sachets. In other aspects, a blood storage device 20 includes from 8 to 24 grams of sorbent 207 contained in one or more sachets. In another aspect, a blood storage device 20 includes 8, 16, or 24 grams of sorbent 207. In an aspect, a blood storage device 20 includes of 8 grams of SS-200 sorbent 207, or its equivalent contained in one sachet. In another aspect, a blood storage device 20 includes 16 grams of SS-200 sorbent 207, or its equivalent contained in two sachets. In another aspect, a blood storage device 20 includes 24 grams of SS-200 sorbent 207, or its equivalent contained in three sachets. In a further aspect, a blood storage device 20 includes 14 grams of sorbent 207 contained in one Dessicare pack or its equivalent. In an aspect, a blood storage device 20 includes about 1 grams of sorbent 207. In yet another aspect, a blood storage device 20 includes about 2 grams of sorbent 103. In an aspect, a blood storage device 20 includes about 3 or 4 grams of sorbent 207 contained in one or more sachets. In an aspect, a blood storage device 20 includes about 0.75 or 1.0 grams of sorbent 207 contained in one or more sachets. The sachets can be square, rectangular, circular, or elliptical.

In aspects according to the present disclosure, the blood storage device 20 includes an oxygen indicator 215 that can serve as an early warning for users that the storage device has become compromised. In aspects according to the present disclosure, compromise of the outer barrier bag 102 or the inlet/outlets 30 results in oxygen within the outer bag headspace. Such unwanted oxygen ingress can occur prior to use (e.g., during shelf storage) or after the device 20 is filled with oxygen depleted blood. An oxygen indicator 215 according to the present disclosure includes devices that are usually constructed of a chemistry on paper or tablet form and enclosed in an oxygen permeable film pack. As used herein, an oxygen indicator 215 is sensitive enough to detect levels of oxygen above 1 Torr of partial oxygen pressure. In the presence of oxygen, an indicator will change color (for example, from pink to purple). This alerts the user of a device 20 that the oxygen impermeable protection may be compromised and to take additional precautions as appropriate. In an aspect, blood in a compromised device 20 may be treated as regular conventional blood during or at storage end. As provided herein, an oxygen indicator 215 is typically integrated into the blood storage bag during bag manufacture. In certain aspects, an oxygen indicator 215 is laminated to a transfer tape such as 3M 1524A and dispensed into the outer bag side facing the inner bag. A exemplary oxygen indicator 215 includes, but is not limited to, the Dry Pak Wondersensor (Dry Pak Industries, Inc., Encino, CA).

The present disclosure provides for, and includes, tubing 205 to connect a blood storage device 10, and other components of a blood collection kit together. Tubing 205 provides a number of functions in a blood collection kit, including but not limited to preventing contamination of blood collection kit and providing for sterile transfer and sterile docking when connections to external sterile tubing is necessary. In the course of development of anaerobic storage bags and as illustrated below in Example 8, it became evident that the primary source of ingressed oxygen both prior to, and during, blood storage device use was tubing 205. Accordingly, the devices and methods of the present disclosure overcome the limitations of the prior art and minimize the impact of oxygen in the storage environment.

In aspects according to the present disclosure, tubing 205 is prepared from materials that are substantially impermeable to oxygen and optionally impermeable to carbon dioxide. In many aspects, tubing 205 is prepared from dense materials that do not have pores or voids. In other aspects, tubing 205 is prepared as a barrier traversing tube 305 as illustrated in FIG. 3 having at least one oxygen barrier layer 307 and at least one blood compatible layer 306. In certain aspects, an oxygen barrier layer 307 and blood compatible layer 306 are the same layer. Also provided for and included in the present disclosure is barrier traversing tube 305, having an inner blood compatible layer 306, an intermediate oxygen barrier layer 307, and outer layer 308. In certain aspects, outer layer 308 provides protection for the oxygen barrier layer 307 and prevents the formation of holes, cracks or other breaches in the oxygen barrier. In certain aspects, outer layer 308 also provides for the formation of bond 302. The present disclosure provides for a barrier traversing tube 305, having a bilayer of a blood compatible layer 306 and a outer layer 308. In certain aspects, an oxygen barrier layer 307 and outer layer 308 are the same layer. In certain aspects, outer layer 308 is suitable to act as a seal adapter 301. In addition to permeability, tubing 205 should be suitable for sterile welding which provides for joining two opposing ends of the tube while maintaining a sterile fluid pathway. In some aspects, tubing 205 is comprised of a barrier traversing tube 305 suitable for sterile welding. In further aspects, tubing 205 should be resistant to kinking, twisting and collapsing. As discussed above, it would be understood by one of ordinary skill in the art that the thickness of the tubing wall is proportional to the permeability of the tubing. Accordingly, while many materials may be suitable when provided with sufficient thickness, such materials may not be suitable as they would lack flexibility or simply be too bulky or unwieldy for use in a blood collection set or to dock with other tubing.

As used herein, tubing 205 that is substantially impermeable to oxygen are materials characterized by a Barrer value of less than 1 Barrer, and preferably less than 0.2 Barrer. In other aspects, tubing 205 that is substantially impermeable to oxygen are materials characterized by a Barrer value of less than 0.01 Barrer. In other aspects, tubing 205 that is substantially impermeable to oxygen are materials characterized by a Barrer value of less than 0.002 Barrer. In other aspects, tubing 205 that is substantially impermeable to oxygen has an oxygen transmission rate of less than 100 cc/mil·100 in$^2$·day·atm. In other aspects, tubing 205 that is substantially impermeable to oxygen has an oxygen transmission rate of less than 80 cc/mil·100 in$^2$·day·atm. In other aspects, tubing 205 that is substantially impermeable to oxygen has an oxygen transmission rate of less than 35 cc/mil·100 in$^2$·day·atm. Examples of tubing suitable for use include PVC tubing, such as Renolit Medituub 3467 (American Renolit Corp., City of Commerce, CA) and Qosina T4306 (Qosina Corp., Edgewood, NY). In some aspects according to the present disclosure, tubing 205 has an oxygen permeability of between 0.002 and 1 Barrer. In aspects according to the present disclosure, tubing 205 has an oxygen permeability of between 0.002 and 0.20 Barrer. In some aspects according to the present disclosure, tubing 205 has an oxygen permeability of between 0.01 and 0.10 Barrer.

In aspects according to the present disclosure, tubing 205 may be prepared from materials selected from the group consisting of ethylene-vinyl acetate (EVA), poly(ethylene-vinyl) acetate (PEVA), polypropylene (PP), polyurethane (PU), polyester (PES), polyethylene terephthalate (PET), polyethylene (PE), high-density polyethylene (HDPE), polyvinyl chloride (PVC), polyvinylidene chloride (PVDC), low-density polyethylene (LDPE), polypropylene (PP), polystyrene (PS), high impact polystyrene (HIPS), polyamides (PA) (e.g., nylon), acrylonitrile butadiene styrene (ABS), polycarbonate (PC), polycarbonate/acrylonitrile butadiene styrene (PC/ABS), polyurethanes (PU), melamine formaldehyde (MF), plastarch material, phenolics (PF), polyetheretherketone (PEEK), polyetherimide (PEI) (Ultem), polylactic acid (PLA), polymethyl methacrylate (PMMA), polytetrafluoroethylene (PTFE), urea-formaldehyde, ethylene vinyl alcohol copolymer (EVOH), and polyamide. In an aspect, tubing 205 is prepared from polyethylene. In an aspect, tubing 205 is prepared from polyvinyl chloride.

The present disclosure also provides for and includes a blood storage device 20 having tubing 205 that is a barrier traversing tube 305 having at least one layer selected from the group consisting of ethylene-vinyl acetate (EVA), poly (ethylene-vinyl) acetate (PEVA), polypropylene (PP), biaxially oriented polypropylene (BOPP), biaxially oriented nylon, ethylvinyl alcohol (EVOH), polyethylene terephthalate (PET), polyethylene napthalate (PEN), polyurethane (PU), polyethylene (PE), polyvinylidene chloride (PVDC), and polyamide. In an aspect, a barrier traversing tube 305 used for tubing 205 includes an oxygen barrier layer 307 comprising PET. In another aspect, a barrier traversing tube 305 used for tubing 205 includes an oxygen barrier layer 307 comprising EVA. In another aspect, a barrier traversing tube 305 used for tubing 205 includes an oxygen barrier layer 307 comprising EVOH. In certain aspects, tubing 205 comprises a blood compatible inner layer 306 comprising PVC. In certain aspects, the barrier traversing tube 305 used for tubing 205 is comprised of an outer layer 308 of polyethylene (PE), and inner layer 306 of PVC (polyvinyl chloride), and an oxygen barrier layer 307 of EVA (ethyl-vinyl-acetate) (Pexco, Inc. Athol, MA). In some aspects, the barrier traversing tube 305 used for tubing 205 is comprised of an outer layer 308 of polyethylene (PE), and inner layer 306 of PVC (polyvinyl chloride), and an oxygen barrier layer 307 of EVA (ethyl-vinyl-acetate), wherein the PE outer layer 308 has a thickness of 150 μm, the EVA oxygen barrier layer 307 has a thickness of 10 μm, and the PVC inner layer 306 has a thickness of 350 μm, thereby providing a multilayer tubing that is easily used with current sterile tubing connection devices. Additives that strengthen the oxygen and $CO_2$ barrier properties of the polymers prior to molding or during their formulation or during setup are known in the art.

Current blood collection kits employ PVC in tubing that is equivalent to the tubing 205 of the present disclosure. Such PVC tubing is not suitable for use in some aspects of the blood storage devices of the present disclosure and would be a considerable source of ingressed oxygen if used as tubing 205. Such PVC tubing typically allows approximately 1 cc oxygen ingress per day over a 1 m length of tubing at ambient conditions; thus blood collection systems and kits of the present invention would require an oxygen barrier overpack with an oxygen sorbent to protect and maintain the internal spaces and volumes of the blood collection kit from undesired oxygen ingress. Since the majority of PVC tubing in the blood collection kit is discarded after collection and processing, and the anaerobic storage device 20 only has 150 mm length of exposed inlet tubing remaining prior to storage, the oxygen ingress rate through the remaining 150 mm length of exposed PVC tubing is limited to about 0.16 cc/day at ambient conditions, or about 7 cc oxygen at ambient conditions over 42 days and about 10 cc after 64 days. The actual amount of oxygen ingress is much lower at the refrigerated storage temperature of 4° C. used for long term blood storage than the amount of oxygen ingress measured at ambient conditions.

The present disclosure includes, and provides for, a blood storage device 10 having unitary tubing design that is substantially impermeable to oxygen that combines and incorporates tubing 205, bond 302, and tubing 304 into a single structure. The advantage of this design is that it decreases the number of individual parts and eliminates potential sources of oxygen ingress. Moreover, the incorporation of a unitary tubing design comprising a multilayered, oxygen impermeable tube provides for the preparation of simplified blood storage device 20 comprising a blood compatible outer receptacle 201 capable of storing oxygen depleted blood bonded directly to one or more inlets or outlets comprising the impermeable tubing. By essentially eliminating the potential sources of oxygen, suitably oxygen depleted blood may be stored directly in the blood compatible outer receptacle 201 while eliminating the collapsible blood container 202 and the oxygen sorbent 207. The present disclosure also provides for the preparation of a blood storage device comprising a multilayered container which combines the outer receptacle 201, oxygen sorbent 207, and the collapsible blood container 202 as a single multilayered device bonded to one or more tubings 205 through an oxygen impermeable bond.

In aspects according to the present disclosure, the outer receptacle 201 includes one or more inlets/outlets 30. In certain aspects, the one or more inlet/outlets 30 further comprise a spike port 303. In some aspects, the outer receptacle 201 includes a second inlet/outlet 30 in fluid communication with said collapsible blood container 202. In yet other aspects, the outer receptacle 201 includes a third inlet/outlet 30 in fluid communication with said collapsible blood container 202. Each inlet/outlet 30 may further include a spike port 303.

It is notable that few materials provide complete impermeability and that even the high impermeability of materials can be compromised when joining, welding, folding, or otherwise assembling an outer receptacle 201. As will be discussed below, blood storage device 20 may further incorporate optional spike ports 303 and inlets/outlets 30 and must also be designed to accommodate changes in volume of the inner collapsible blood container 202. Accordingly, special care is taken to incorporate specific design elements and manufacturing methods to ensure the integrity of the impermeable barrier and the maximization of material performance integrity.

Spike ports 303 for use in blood collection kits and systems are commonly known in the art and include products such as Vitalmed #20391 (Vitalmed, Inc., Lakeville, MA) and Qosina #65842 (Qosina Corp., Edgewood, NY). These ports are typically molded from PVC and have a removable cap that provides for a sterile barrier before use, and also provides for some degree of oxygen impermeability to the contents. In some aspects, a spike port 303 is covered by a sealed, frangible section of the outer receptacle film, thereby providing for a sterile barrier and also providing an additional degree of oxygen impermeability. Improved oxygen impermeability is desirable as it increases the shelf life of kits and systems having a blood storage device 20.

As will be appreciated, conventional ports, inlets, and outlets are potential sources of unwanted oxygen ingression that depend both on the selection of the material and the methods used to bond the port, inlet, or outlet to the outer receptacle 201. Methods of bonding materials to prepare a bond 302 are well known in the art. As provided herein, inlet/outlet 30 comprises a seal adaptor 301 joined to the outer receptacle 201 using bond 302 which creates an oxygen impermeable seal to the outer receptacle 201. In one aspect of the present disclosure, a manifold is a seal adapter 301. As used herein, a bond 302 that is substantially impermeable to oxygen has a Barrer value of less than 1 Barrer, preferably less than 0.10 Barrer, and more preferably less than 0.01 Barrer.

As provided in the present disclosure, a bond 302 that is substantially impermeable to oxygen may be solvent sealed, heat sealed, adhesive bonded, ultrasonic welded, or radio frequency welded. In an aspect, bond 302 is achieved by using constant heat sealing dies heated to and maintained at about 260° F. In an aspect, films are placed between heated dies and clamped together for about 3 to 7 seconds to achieve a thermally welded seam. In certain aspects, a heat seal is created in about 5 seconds. In certain aspects, the sealing dies have a grooved section machined out of them to accommodate an intermediary component. In some aspects seal adaptor 301 comprises an intermediary component that may be a length of barrier traversing tubing as discussed below or a small block of machined, extruded, molded or laminated polymer wedge. In aspects according to the present disclosure, the groove is dimensioned about 5% smaller than the features of the component, thereby providing for compression and material flow during sealing.

In some aspects, an oxygen impermeable bond is comprised of a section of barrier traversing tube (e.g., seal adaptor 301) that is heat sealed into the seam of the outer receptacle 201. In certain aspects, the barrier traversing tube is comprised of an outer layer of EVA (ethyl-vinyl-acetate) and an inner layer of PVC (polyvinyl chloride) (Pexco, Inc., Athol, MA). In certain aspects, the barrier traversing tube is comprised of an outer layer of polyethylene, and inner layer of PVC (polyvinyl chloride), and an intermediary layer of EVA (ethyl-vinyl-acetate) (Extrusion Alternatives, Inc., Portsmouth, NH). In some aspects, additional sections of PVC tubing are solvent bonded into the multilayer tube using, for example, cyclohexanone.

In some aspects, an inlet/outlet 30 is comprised of a seal adaptor 301 that is a small device that is a machined, extruded, molded or laminated polymer wedge or a block. The molded device may be prepared from a polyolefin, such as polyethylene, for example Dowlex® 2517 resin. In other aspects the machined, extruded, molded or laminated polymer device may be prepared from a polyether block amide (e.g., PEBAX®). In yet another aspect, the machined, extruded, molded or laminated polymer may be ethylene-vinyl acetate (e.g., EVA). In certain aspects, the machined, extruded, molded or laminated polymer device may be a small diamond, oval or other suitably shaped, block of polymer, with a hole through the center, such that the shaped device is heat sealed into the seam of the outer receptacle to provide an oxygen impermeable bond 302 while the center through-hole provides for fluid connectivity with the contents. In an aspect, a section of PVC tubing is bonded into the center hole of a diamond shaped seal adaptor 301 using an oxygen impermeable adhesive capable of bonding to polyethylene, such as Loctite 4310, Masterbond X17, or 3M Scotchweld 4693, thereby providing for fluid connectivity through the oxygen impermeable outer receptacle to the contents therein. In other aspects, a barrier traversing tubing can be bonded to the center hole of the diamond shaped seal adaptor 301 using methods known in the art. In other aspects, barrier traversing tubing can be insert molded into a diamond shaped seal adaptor 301 using methods known in the art. In other aspects, barrier traversing tubing can be utilized in place of standard PVC intravenous tubing to provide for enhanced oxygen barrier properties.

The present disclosure provides for and includes a locating feature to align the outer receptacle 201, collapsible blood container 202 and inlet/outlet 30 and ensure the integrity of the oxygen impermeable barrier. Misalignment can result in breaches to the barrier and ingress of oxygen during storage and prior to use. In accordance with the present disclosure, the locating feature may be selected from the group consisting of a geometric cutout, a tactile surface marking, die cut fiducials, spacers, interlocking cutouts, tubing fittings, and a printed marking.

The present disclosure provides for and includes an expansion feature 217 to accommodate the volume of blood and to avoid creases and folds. During the development of anaerobic storage bags, it was observed that creases and folds that developed during the filling of certain anaerobic storage bags, for example foil coated bags, results in breaches of the impermeable barrier. Such folds and creases result in unacceptable levels of oxygen ingress and leads to unacceptable increases in oxygen saturation in stored blood during storage. Expansion features also provide for unrestricted filling of the storage device 20, the outer enclosure 201, and the collapsible blood container 202.

Figure 8:
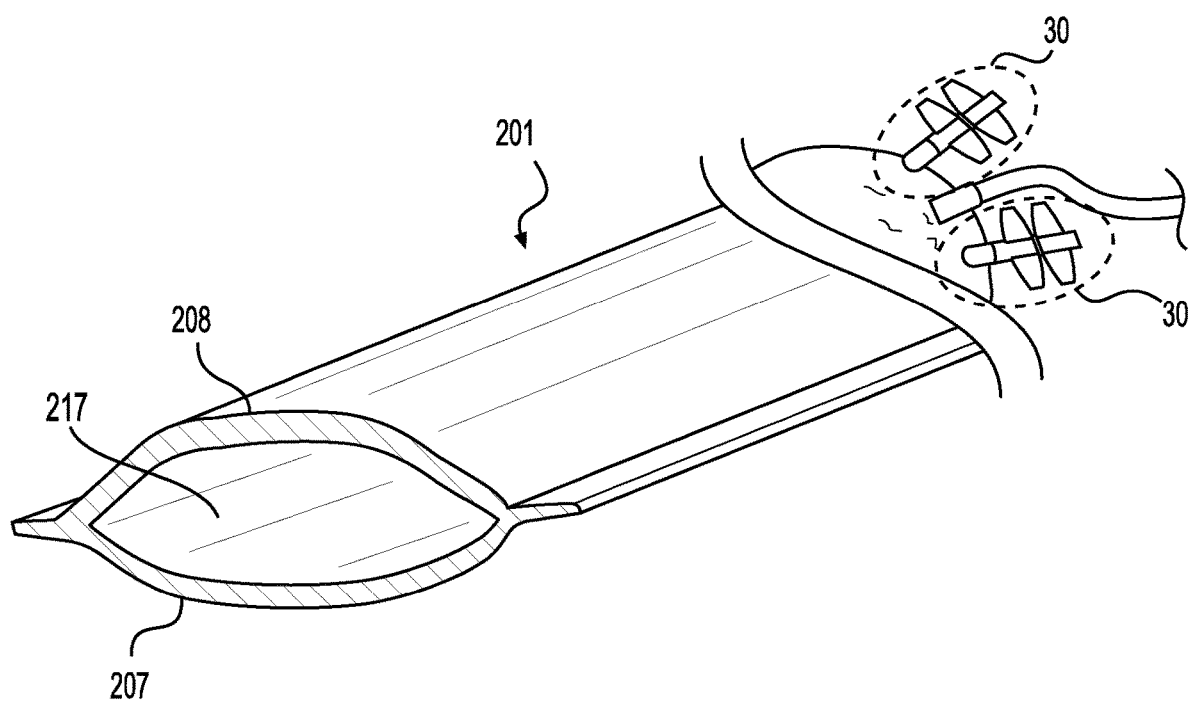
FIG. 8 illustrates an outer receptacle 201 incorporating an expansion feature 217 according to an aspect of the present disclosure.

In aspects according to the present disclosure, an expansion feature 217 is selected from a group consisting of a pleat, a diaphragm, a bubble, one or more folds, a folded pouch, and a geometric expansion in the packaging shape. In some aspects, the expansion feature 217 is comprised of a gusseted fold along one or more edges of the outer receptacle 201. In an aspect, a fold of about ⅛ to ¼ inch is adequate to provide for expansion of the inner container 202, and the pleats of the fold are sealed into the seams at the ends. In some aspects, and as illustrated in FIG. 8, the expansion feature 217 is comprised of a third panel or trifold of barrier film sealed along the bottom of the outer receptacle 201, providing for a three-dimensional bag.

In certain aspects, the collapsible blood container 202 may also include expansion features to facilitate filling of the container, though the oxygen impermeable integrity of the container 202 is obviously not of concern.

Figure 6E:
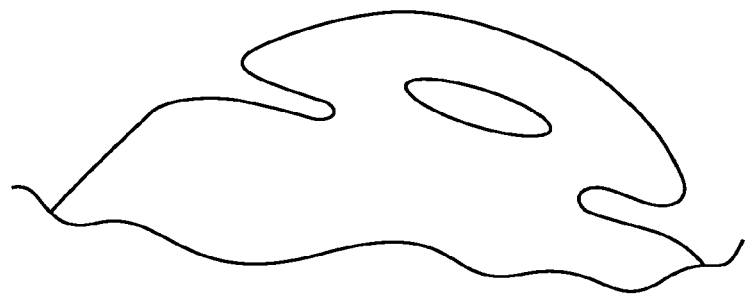
Figure 6F:
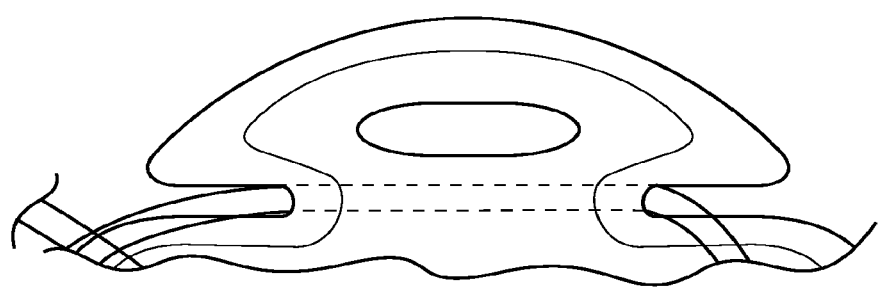

The present disclosure provides for and includes methods and systems to manage the tubing 205 and other tubes that are associated with a complete blood collection kit. A blood storage device 20 having an outer receptacle 201, collapsible blood container 202 at least one inlet/outlet 30, and oxygen sorbent 207 may further comprise tube management component 40. Tube management component 40 may be selected from the group consisting of a separate clip or strap as illustrated in FIGS. 6A and 6B, a strap attached to the outer surface of said outer receptacle such as that illustrated in FIGS. 6C and 6D, and a hook and loop fastener (VELCRO®). In certain aspects, and as illustrated for example in FIGS. 6E and 6F, tube management component 40 is a cut out feature of the outer surface of said outer receptacle. In another aspect, tube management component 40 is a clip attached outer surface of said outer receptacle.

Figure 7:
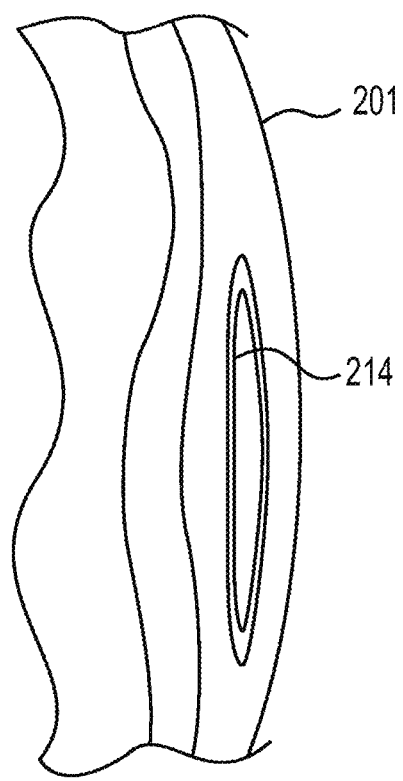
FIG. 7 illustrates an integrated handle 214 according to an aspect of the present disclosure.

The present disclosure provides for and includes an integrated handle 214 in the outer receptacle 201, for example as illustrated in FIG. 7.

The present disclosure provides for and includes one or more transparent or translucent windows 212 to provide for the visual inspection of the blood. Such a window allows for the inspection of the color of the blood, and also for visualizing undesirable features or contaminants, such as blood clots or bacterial colonies, if present in the blood.

Among other factors, the shelf life and stability of a blood storage device 20 can be significantly affected by temperature. Specifically, a blood storage device 20, or one or more of the components thereof, may degrade when exposed to high temperatures. Such degraded devices are unsuitable for the storage of blood and may result in unwanted patient outcomes. As would be known to a person of skill in the art, the amount of time the device is exposed to undesirable temperatures is important as well. Accordingly, the present disclosure provides for devices that further include temp-time monitors. Such monitors are known in the art for example as provided in U.S. Pat. Nos. 7,517,146, 6,042,264, and 5,709,472. In an aspect, a BT-10 time strip from Genesis (GenesisBPS, Ramsey, NJ) can be incorporated on the collapsible blood container to monitor the duration of any temperature incursions above 10° C.

The present disclosure provides for an includes a blood storage device 20 for storing oxygen depleted blood that provide for maintaining a headspace comprising a volume between said outer receptacle 201 and said collapsible blood container 202 at a low partial pressure of oxygen during a storage period. In some aspects, the blood storage device can maintain the headspace of the blood storage device 20 without the need to include sorbent 207, however such configurations required a higher level of oxygen barrier integrity. As provided by the present disclosure, a blood storage device 20 maintains the headspace at a partial pressure of oxygen of about 1 mmHg, or less, for a period of 64 days when stored at a temperature of between 2 to 6° C. In some aspects, a blood storage device 20 maintains the headspace at a partial pressure of oxygen of about 1 mmHg, or less, for a period of 64 days when stored at a temperature of between 2 to 6° C., without the inclusion of sorbent 207. The present disclosure also provides for an includes a blood storage device that maintains a partial pressure of oxygen in the headspace of 1 mmHg or less for at least 6 months prior to use.

The present disclosure further includes a blood storage device 20 having an inlet/outlet 30 that is substantially impermeable to oxygen that maintains the headspace at a partial pressure of oxygen 1 mmHg, or less, for a period of at least 21 days. In some aspects, a blood storage device 20 having an inlet/outlet 30 that is substantially impermeable to oxygen is a blood storage device 20 that maintains the headspace at a partial pressure of oxygen 1 mmHg, or less, for a period of at least 21 days without sorbent 207. The present disclosure also provides for a blood storage device 20 having an inlet/outlet 30 that is substantially impermeable to oxygen is a blood storage device 20 wherein the headspace is maintained at a partial pressure of oxygen 1 mmHg, or less, for a period of at least 28 days. In some aspects, the headspace is maintained at a partial pressure of oxygen 1 mmHg, or less, for a period of at least 28 days without sorbent 207. In further aspects, the headspace is maintained at a partial pressure of oxygen 1 mmHg, or less, for a storage period of at least 28 days. In some aspects, the headspace is maintained at a partial pressure of oxygen 1 mmHg, or less, for a period of at least 21 days without sorbent 207. In further aspects, the headspace is maintained at a partial pressure of oxygen 1 mmHg, or less, for a period of at least 48 days. In some aspects, the headspace is maintained at a partial pressure of oxygen 1 mmHg, or less, for a period of at least 48 days without sorbent 207. In another aspect, the headspace is maintained at a partial pressure of oxygen 1 mmHg, or less, for a period of at least 56 days. In some aspects, the headspace is maintained at a partial pressure of oxygen 1 mmHg, or less, for a period of at least 56 days without sorbent 207. In another aspect, is maintained at a partial pressure of oxygen 1 mmHg, or less, for a storage period of at least 64 days. In some aspects, the headspace is maintained at a partial pressure of oxygen 1 mmHg, or less, for a storage period of at least 64 days without sorbent 207.

The present disclosure further includes a blood storage device 20 having an inlet/outlet 30 that is substantially impermeable to oxygen that maintains the headspace at a partial pressure of oxygen 3 mmHg, or less, for a period of at least 21 days. In some aspects, a blood storage device 20 having an inlet/outlet 30 that is substantially impermeable to oxygen is a blood storage device 20 that maintains the headspace at a partial pressure of oxygen 3 mmHg, or less, for a period of at least 21 days without sorbent 207. The present disclosure also provides for a blood storage device 20 having an inlet/outlet 30 that is substantially impermeable to oxygen is a blood storage device 20 wherein the headspace is maintained at a partial pressure of oxygen 3 mmHg, or less, for a period of at least 28 days. In some aspects, the headspace is maintained at a partial pressure of oxygen 3 mmHg, or less, for a period of at least 28 days without sorbent 207. In further aspects, the headspace is maintained at a partial pressure of oxygen 3 mmHg, or less, for a storage period of at least 28 days. In some aspects, the headspace is maintained at a partial pressure of oxygen 3 mmHg, or less, for a period of at least 21 days without sorbent 207. In further aspects, the headspace is maintained at a partial pressure of oxygen 3 mmHg, or less, for a period of at least 48 days. In some aspects, the headspace is maintained at a partial pressure of oxygen 3 mmHg, or less, for a period of at least 48 days without sorbent 207. In another aspect, the headspace is maintained at a partial pressure of oxygen 3 mmHg, or less, for a period of at least 56 days. In some aspects, the headspace is maintained at a partial pressure of oxygen 3 mmHg, or less, for a period of at least 56 days without sorbent 207. In another aspect, is maintained at a partial pressure of oxygen 3 mmHg, or less, for a storage period of at least 64 days. In some aspects, the headspace is maintained at a partial pressure of oxygen 3 mmHg, or less, for a storage period of at least 64 days without sorbent 207.

The present disclosure further includes a blood storage device 20 having an inlet/outlet 30 that is substantially impermeable to oxygen that maintains the headspace at a partial pressure of oxygen 5 mmHg, or less, for a period of at least 21 days. In some aspects, a blood storage device 20 having an inlet/outlet 30 that is substantially impermeable to oxygen is a blood storage device 20 that maintains the headspace at a partial pressure of oxygen 5 mmHg, or less, for a period of at least 21 days without sorbent 207. The present disclosure also provides for a blood storage device 20 having an inlet/outlet 30 that is substantially impermeable to oxygen is a blood storage device 20 wherein the headspace is maintained at a partial pressure of oxygen 5 mmHg, or less, for a period of at least 28 days. In some aspects, the headspace is maintained at a partial pressure of oxygen 5 mmHg, or less, for a period of at least 28 days without sorbent 207. In further aspects, the headspace is maintained at a partial pressure of oxygen 5 mmHg, or less, for a storage period of at least 28 days. In some aspects, the headspace is maintained at a partial pressure of oxygen 5 mmHg, or less, for a period of at least 21 days without sorbent 207. In further aspects, the headspace is maintained at a partial pressure of oxygen 5 mmHg, or less, for a period of at least 48 days. In some aspects, the headspace is maintained at a partial pressure of oxygen 5 mmHg, or less, for a period of at least 48 days without sorbent 207. In another aspect, the headspace is maintained at a partial pressure of oxygen 5 mmHg, or less, for a period of at least 56 days. In some aspects, the headspace is maintained at a partial pressure of oxygen 5 mmHg, or less, for a period of at least 56 days without sorbent 207. In another aspect, is maintained at a partial pressure of oxygen 5 mmHg, or less, for a storage period of at least 64 days. In some aspects, the headspace is maintained at a partial pressure of oxygen 5 mmHg, or less, for a storage period of at least 64 days without sorbent 207.

The present disclosure further includes a blood storage device 20 having an inlet/outlet 30 that is substantially impermeable to oxygen that maintains the headspace at a partial pressure of oxygen 15 mmHg, or less, for a period of at least 21 days. In some aspects, a blood storage device 20 having an inlet/outlet 30 that is substantially impermeable to oxygen is a blood storage device 20 that maintains the headspace at a partial pressure of oxygen 15 mmHg, or less, for a period of at least 21 days without sorbent 207. The present disclosure also provides for a blood storage device 20 having an inlet/outlet 30 that is substantially impermeable to oxygen is a blood storage device 20 wherein the headspace is maintained at a partial pressure of oxygen 15 mmHg, or less, for a period of at least 28 days. In some aspects, the headspace is maintained at a partial pressure of oxygen 15 mmHg, or less, for a period of at least 28 days without sorbent 207. In further aspects, the headspace is maintained at a partial pressure of oxygen 15 mmHg, or less, for a storage period of at least 28 days. In some aspects, the headspace is maintained at a partial pressure of oxygen 15 mmHg, or less, for a period of at least 21 days without sorbent 207. In further aspects, the headspace is maintained at a partial pressure of oxygen 15 mmHg, or less, for a period of at least 48 days. In some aspects, the headspace is maintained at a partial pressure of oxygen 15 mmHg, or less, for a period of at least 48 days without sorbent 207. In another aspect, the headspace is maintained at a partial pressure of oxygen 15 mmHg, or less, for a period of at least 56 days. In some aspects, the headspace is maintained at a partial pressure of oxygen 15 mmHg, or less, for a period of at least 56 days without sorbent 207. In another aspect, is maintained at a partial pressure of oxygen 15 mmHg, or less, for a storage period of at least 64 days. In some aspects, the headspace is maintained at a partial pressure of oxygen 15 mmHg, or less, for a storage period of at least 64 days without sorbent 207.

The present disclosure provides for and includes, a blood storage device 20 comprising an outer receptacle 201, a collapsible blood container 202, at least one inlet/outlet 30 and an oxygen sorbent 207, wherein blood stored in said collapsible blood container 202 maintains an oxygen saturation level (SO2) during a storage period that is approximately equal to the oxygen saturation level at the beginning of storage. In an aspect, the storage period is 21 days and the initial SO2 level is 20% or less. In another aspect, the storage period is 28 days and the initial SO2 level is 20% or less. In a further aspect, the storage period is 42 days and the initial SO2 level is 20% or less. In a further aspect, the storage period is 56 days and the initial SO2 level is 20% or less. In yet another aspect, the storage period is 64 days and the initial SO2 level is 15% or less. In an aspect, the storage period is 21 days and the initial SO2 level is 15% or less. In another aspect, the storage period is 28 days and the initial SO2 level is 15% or less or the storage period is 42 days and the initial SO2 level is 15% or less. In a further aspect, the storage period is 56 days and the initial SO2 level is 15% or less or the storage period is 64 days and the initial SO2 level is 15% or less. In an aspect, the storage period is 21 days and the initial SO2 level is 10% or less or the storage period is 28 days and the initial SO2 level is 10% or less. In a further aspect, the storage period is 42 days and the initial SO2 level is 10% or less. In a further aspect, the storage period is 56 days and the initial SO2 level is 10% or less or the storage period is 64 days and the initial SO2 level is 10% or less. In an aspect, the storage period is 21 days and the initial SO2 level is about 5%. In another aspect, the storage period is 28 days and the initial SO2 level is about 5% or the storage period is 42 days. In a further aspect, the storage period is 56 days and the initial SO2 level is about 5%, or the storage period is 64 days. In yet another aspect, the storage period is 21 days and the initial $SO_2$ level is about 3%. In another aspect, the storage period is 28 days and the initial SO2 level is about 3% or the storage period is 42 days and the initial SO2 level is about 3%. In a further aspect, the storage period is 56 days and the initial SO2 level is about 3%. In yet another aspect, the storage period is 64 days and the initial SO2 level is about 3%.

The present disclosure provides for and includes, a blood storage device 20 comprising an outer receptacle 201, a collapsible blood container 202, at least one inlet/outlet 30, and an oxygen sorbent 207, that provides for an oxygen saturation level (SO2) during a storage period that is less than the oxygen saturation level at the beginning of storage, wherein said storage period is at least 1 week. In aspects according to the present disclosure, oxygen saturation level is 2% less after one week of storage than the oxygen saturation level at the beginning of storage. In other aspects, according to the present disclosure, the oxygen saturation level decreases at a rate of at least 0.00010% SO2/minute. In certain aspects, the oxygen saturation level decreases at a rate of at least 0.00020% SO2/minute. In other aspects, the oxygen saturation level decreases at a rate of between 0.0003 and 0.0001% $SO_2$/minute. In other aspects, the storage period is 21 days or 28 days. In yet other aspects, the storage period is 42 of 56 days. In other aspects, the blood storage device 20 provides for a decreased oxygen saturation level after 64 days.

The present disclosure provides for and includes, a blood storage device 20 comprising an outer receptacle 201, a collapsible blood container 202, at least one inlet/outlet 30, wherein blood and said blood stored in said collapsible blood container 202 provides for an oxygen saturation level (SO2) during a storage period that increases less than 5% over the oxygen saturation level at the beginning of storage, wherein said storage period is 64 days. In other aspects, the oxygen saturation level (SO2) during a storage period that increases less than 3% over the oxygen saturation level at the beginning of storage, wherein said storage period is 64 days.

The present disclosure provides for, and includes, different methods to manufacture a collapsible blood container 202. In an aspect, a collapsible blood container 202 is prepared by blow molding. In another aspect, a collapsible blood container 202 is prepared by compression molding. In a further aspect, a collapsible blood container 202 is prepared by insert molding. Methods of blow molding, compression molding, or insert molding are known in the art, for example, "Rupture resistant blow molded freezer bag for containing blood products" in US Patent Application Publication No. 2004/0254560A1 and "Blowbag manufacturing method" in U.S. Pat. No. 5,368,808 issued to Koike et al., and "Blow or vacuum molding thermoplastic resins, then expanding or shaping using compressed air; medical equipment" in U.S. Pat. No. 6,878,335.

In some aspects according to the present disclosure, a collapsible blood container 202 is prepared by heat sealing one or more membranes 206. In another aspect, a collapsible blood container 202 is prepared by adhesive bonding one or more membranes 206. In other aspects, a collapsible blood container 202 is prepared by ultrasonic welding one or more membranes 206. In other aspects, a collapsible blood container 202 is prepared by radio frequency welding one or more membranes 206. In yet other aspects, a collapsible blood container 202 is prepared by one or more methods selected from heat sealing, adhesive bonding, ultrasonic welding, or radio frequency welding.

In aspects according to the present disclosure, the collapsible blood container 202 is prepared from one or more membranes 206 that comprise one or more seals having a width of at least ⅛ inch.

In an aspect according to the present disclosure, the collapsible blood container 202 can be manufactured from microporous membrane 206 by various sealing methods such as heat sealing, thermal staking, and adhesive bonding. In one aspect according to the present disclosure, a pair of PVDF microporous membranes are bonded together around the periphery with a section of PVC inlet tubing in place in the seam using an adhesive such as Loctite 4011 in conjunction with an adhesive primer such as Loctite 770. In another aspect according to the present disclosure, a collapsible blood container can be manufactured from a pair of microporous membranes by heat sealing the 3 or 4 edges of the pair of membranes together with a section of multilayer tubing sealed into the seam to provide for fluid connectivity.

The present disclosure provides for, and includes, methods of using a blood storage device 20 to store deoxygenated blood for up to 64 weeks, resulting in reduced storage lesions relative to blood stored in the presence of oxygen. According to the methods of the present disclosure, a blood storage device 20 as described above is used to for blood storage. In an aspect, the blood comprises packed red blood cells. In other aspects, the blood comprises whole blood. In yet other aspects, the blood for storage comprises oxygen reduced packed red blood cells further comprising an additive solution.

In an aspect, according to a method of the present disclosure, deoxygenated blood, having an oxygen saturation of less than 20% is placed in a blood storage device 20, and stored. In certain aspects, the storage period is between 1 day and 64 days. In other aspects, the storage period is one week. In another aspect the storage period is two weeks. In another aspect, the storage period is three of four weeks. On other aspects, the storage period is 8 weeks. In yet another aspect the storage period is 9 weeks. According to the methods of the present disclosure, the blood storage device 20 maintains the oxygen depleted state of the oxygen depleted blood at, or less than the initial saturation level, $SO_2$.

The present disclosure also provides for and includes, methods of blood storage, comprising placing oxygen reduced blood into a blood storage device 20 and storing the oxygen reduced blood for a period of 1 to 64 days, wherein the oxygen saturation of the blood is further reduced during the storage period. In an aspect, the $SO_2$ of the stored blood is reduced by at least 3% after one week of storage. In an aspect, the initial oxygen saturation of the oxygen reduced blood is about 20% SO2 and is reduced during storage. In other aspects, the initial $SO_2$ is about 15% and is reduced during storage. In yet another aspect, the initial $SO_2$ is about 10% and is reduced during storage. In aspects according to the present disclosure, the stored blood has an oxygen saturation level of less than 20% after one week. In another aspect, the stored blood has an oxygen saturation level of less than 10% after two weeks. In yet another aspect, the stored blood has an oxygen saturation level of less than 5% after three weeks.

EXAMPLES

Example 1: Inner Collapsible Blood Containers Comprising PVC

A collapsible blood container 202 (blood bag) with two inlet/outlets 30 configured as spike ports and one inlet/outlet 30 configured as an I.V. inlet tube is fabricated from a pair of PVC sheets (Renolit Solmed ES-3000, Renolit America) by welding the edges together with radio frequency welding (RF welding). The blood bag is leak tested by insufflating with compressed air to 3 psig and submerging in water and observing for bubbles before use. Alternatively, the blood bag is leak tested by insufflating with compressed air and negative pressure changes are monitored with a pressure decay tester (Sprint MT, Zaxis). The leak-tested blood bag is then placed in an outer receptacle 201 fabricated from RollPrint Clearfoil® Z film #37-1275 having a heat sealable PE inner layer, and alumina barrier middle layer, and a PET outer layer (Rollprint Packaging Products, Inc., Addison, IL) as described in Example 2.

Example 2: Outer Receptacle 201

An outer receptacle 201 that is substantially impermeable to oxygen ("barrier bag") is fabricated by heat sealing an oxygen impermeable section of tubing into one edge with a custom heat sealer, and sealing the other remaining edges using conventional heat sealing methods and equipment. The custom heat sealer is comprised of a pair of 1 inch square aluminum bars 12 inches long having a ½ inch wide by ¼ inch high sealing surface machined on one side of each bar. Each of the sealing bars are fitted with a pair of ⅜ inch diameter by 5 inch long 200 watt heater cartridges (4 total, McMaster Carr #3618K315, McMaster Carr, Inc., Robbinsville, NJ) and maintained at 260° F. by an Athena Controls temperature controller and a K-type thermocouple (McMaster Carr #9251T93, McMaster Carr, Inc., Robbinsville, NJ)

inserted into a small hole drilled in one end of one of the aluminum bars. A transverse groove is machined into each of the two aluminum sealing bars with a 7/32 inch ball end mill to a depth of about 0.208 inches to provide for about 0.010 inches of compression when locating a seal adaptor comprising a section of oxygen impermeable tubing within the seal. The bars are bolted in opposition to each other on a Franklin Hot Stamp press, such that when the press is operated the transverse grooves and pair of sealing surfaces come into aligned contact with each other to provide a" inch wide seal along the 12 inch length of the aluminum sealing bars.

To prepare the outer receptacle 201, a sheet of the barrier film about 11×12 inches is folded in half along the 12 inch dimension with the polyethylene layer inside and a gusset fold of about ¼ inch incorporated into the folded edge. The gusset fold is maintained in place with a small clamp at each end and then the film is placed into the custom heat sealer aligning one of the short edges in the sealing dies. A piece of oxygen impermeable multilayer tubing (seal adaptor 301) having a polyethylene outer layer 308, a PVC inner layer 306, and an intermediary bonding layer of EVA 307, (Extrusion Alternatives, Inc., Portsmouth, NH) 0.156" I.D. by 0.218" O.D. by about ½ inch long is placed onto a solid aluminum mandrel about 0.156" diameter by about 1 inch length and then placed between the films and located in the transverse groove 703 or 704 of the sealing die 70. The press is activated and set to about 5 seconds duration at 80 pounds per square inch gage (psig) to create a continuous welded seal along the length of the dies, and sealing the short piece of multilayer tubing (seal adaptor 301) in place with bond 302. The combination of seal adaptor 301 and bond 302 short multilayer tubing provides for an oxygen impermeable seal around the outer diameter of the tubing while also providing fluid connectivity through the seal. The folded edge provides for expansion of the barrier bag when the collapsible blood container 202 is filled with fluid.

A length of standard I.V. tubing (PVC tubing 0.118 inch I.D.×0.161 inch O.D. (Pexco, Inc., Athol, MA) about 12 inches long (tubing 205) is solvent bonded using cyclohexanone into the multilayer tubing from the outside of the bag and heat sealed closed about ½ inch from the end. The inlet tubing (tubing 304) of the inner blood bag is trimmed to about 2 inches in length and the inner blood bag is placed inside the barrier bag. The inlet tubing 304 is solvent bonded into the multilayer tubing, thereby providing for fluid connectivity of the inner blood bag inlet tube through the oxygen impermeable seal of the barrier bag to the 12 inch length of tubing 205 outside the barrier bag.

The remaining short edge of the barrier film is sealed with an impulse heat sealer (Accu-Seal model 530, Accu-Seal, Inc., San Marcos, CA), leaving the last remaining long edge of the barrier bag unsealed to place a sorbent 207, plastic mesh spacer 213 configured as a plastic mesh, and oxygen sensor 215. An oxygen sensor 215 (Mocon #050-979, Mocon, Inc., Minneapolis, MN) is affixed to the inside of the barrier bag. A pair of plastic mesh spacers 213 (McMaster Carr #9314T29, NJ McMaster Carr, Inc., Robbinsville, NJ) are cut to about 5×7 inches and one sachet of oxygen sorbent 207 (SS-200 type, Mitsubishi Gas Chemical America, New York, NY) is affixed near the center of one piece of plastic mesh 213 prior to placing the plastic mesh spacers 213 between the blood bag 202 and barrier bag 201 and sealing the final long edge of the barrier bag with an impulse heat sealer (McMaster Carr #2054T35, McMaster Carr, Inc., Robbinsville, NJ). Care is taken to minimize the assembly time to reduce the exposure to atmospheric oxygen by performing the assembly in a nitrogen atmosphere glove box.

Example 3: Conventional Storage Bags Allow for Blood Reoxygenation

The extent and rate of reoxygenation of blood during storage in conventional PVC blood storage bags is determined by transferring 150 ml of packed Red Blood Cells (pRBC) having an initial SO2 of about 60% to a conventional PVC blood transfer bag. The pRBC containing bag is placed at 4° C. under ambient atmospheric conditions and allowed to stand, unmixed. Samples are removed and the average SO2 determined at days 0, 7, 14, 21, 28, 52, and 56. Six independent samples are taken per time point. The results are presented in Table 7 and presented graphically in FIG. 10.

TABLE 7

| Reoxygenation of blood during storage in conventional PVC bags | |
|---|---|
| Storage Time (days) | Average SO2 (%) |
| 0 | 62.4 |
| 7 | 80.8 |
| 14 | 95.5 |
| 21 | 98.3 |
| 28 | 98.2 |
| 42 | 97.9 |
| 56 | 97.6 |

Figure 10:
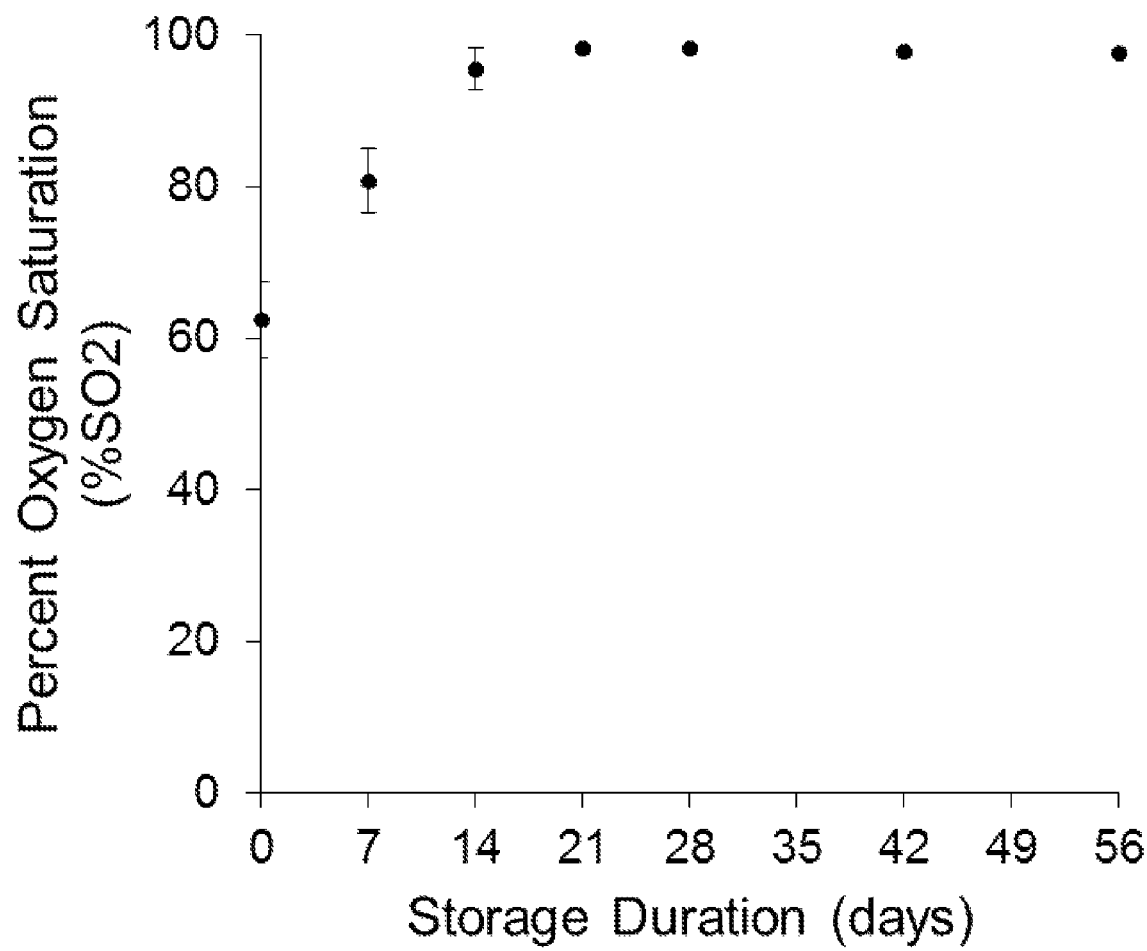
FIG. 10 presents a graph of oxygen absorption that occurs in conventional storage bags.

As shown in Table 7 and FIG. 10, blood becomes saturated over the 56 day storage period. $SO_2$ increases consistently for 14-21 days, until it reaches ~98%, after which there are no significant (n=6; p<0.001) changes in $SO_2$ for the remainder of the storage period.

Example 4: Oxygen Ingress Occurs Primarily Through Collection and Transfer Tubing Based on calculations and comparing to a bag made from the RollPrint 37-1275, 8.53 ml oxygen ingresses over 42 days with the majority coming through the 6" length of inlet tubing. Accordingly, a 20 cc minimum sorbent capacity, based on the 8.53 ingress+10 mL in blood is indicated.

Example 5: Continued Oxygen Depletion During Storage at 4° C.

The depletion of oxygen is significantly affected by temperature. To evaluate the ability to continue to deplete oxygen from blood during storage, conventional blood storage bags are prepared and filled with blood having differing initial levels of oxygen saturation. Packed red blood cells are prepared in PAGGSM or SAGM additive solution and are stored anaerobically within plastic canisters pressurized with ~5 mmHg, 100% nitrogen gas; additionally, each canister containing 2 ZB sorbent sachets to assist in keeping oxygen levels negligible. As shown in Table 8, at higher levels of oxygen saturation, the rate of the reaction is about twice that of the reaction rate at lower levels of saturation.

TABLE 8

First order rate constants of oxygen
depletion during cold storage

| Initial (Day 0) SO$_2$ | Kinetic Rate (% SO2/min) |
|---|---|
| 3 | −2.07917E−05 |
| 10 | −0.000102393 |
| 20 | −0.00019752 |
| 39 | −0.000250115 |
| 48 | −0.000270159 |
| 54 | −0.000268709 |

There also appears to be a logarithmic relationship between the initial set-point of SO$_2$, and the total amount of O$_2$ removed during storage, as indicated by a coefficient of determination (R$^2$) of 0.98. Deriving the line of best fit from this data also allows for the extrapolation of predicted O$_2$ variance for a given initial SO$_2$ set-point to inform (Eq. 1).

$$\Delta SO_2 = 7.195 \ln(SO_{2,i}) - 6.99$$

Equation 1 Logarithmic equation relating initial SO$_2$ to total SO$_2$ loss during storage. Deriving the equation of line of best fit from the plot of change in SO$_2$ ($\Delta SO_2$) and initial SO$_2$ values (SO$_{2,i}$)

Additionally, the time-dependent loss of SO$_2$ can be predicted by plotting the slopes of a linear regression and deriving the line of best fit. There appears to be a logarithmic relationship between the initial SO$_2$ value at the start of storage, and the linear rate at which SO$_2$ is lost during anaerobic storage (Eq 2).

$$k = -0.131 \ln(SO_{2,i}) + 0.1241$$

Equation 2 Logarithmic equation relating initial SO$_2$ to linear rate of SO$_2$ loss during storage. Derived equation for the line of best fit from the plot of rate of SO$_2$ loss (k) versus initial SO$_2$ value (SO$_{2,i}$)

Example 6: Preparation of Outer Receptacles

Pairs of oxygen barrier films are heat sealed together on all four sides to yield pouches having inner dimensions of about 160 by 240 mm. The pouches are sealed using an impulse heat sealer having about a 3 mm (⅛") wide seal (McMaster Carr #2054T35, McMaster Carr, Inc., Robbinsville, NJ). Samples are prepared from the following barrier films: Rollprint Clearfoil® Z film #37-1275 and Clearfoil® V film #27-1232 (Rollprint Packaging Products, Inc., Addison, IL), and Glenroy ESO 031-002 (Glenroy, Inc., Menomonee Falls, WI). Samples of the Rollprint Clearfoil® Z film are also prepared using an impulse heat sealer having about a 9.5 mm (⅜") wide seal (Accu-Seal model 530, Accu-Seal, Inc., San Marcos, CA).

Several samples of each configuration are prepared and tested for oxygen permeation using an Oxtran 2/61 oxygen permeability instrument (Mocon, Inc., Minneapolis, MN). For each configuration, two samples are selected for testing using a test gas comprising 100% oxygen at 50% relative humidity (RH) and 760 mmHg pressure. The carrier gas is 98% nitrogen/2% hydrogen at 100% RH and conducted at 23° C. The results are shown in the Table 9 below:

TABLE 9

Permeability of outer receptacles 201 prepared from different materials

| Description | Sample # 1 | Sample # 2 |
|---|---|---|
| Rollprint 37-1275 3-mm seal | 0.0053 | 0.0053 |
| Rollprint 37-1275 9.5-mm seal | 0.0049 | 0.0051 |
| Rollprint 27-1237 3-mm seal | 0.0457 | 0.0564 |
| Glenroy 031-002 3-mm seal | 0.0496 | 0.0504 |

While all samples showed a low oxygen ingress rate of less than 0.1 cc/package*day, the Clearfoil® Z film was clearly superior by an order of magnitude lower oxygen ingress rate than the other materials. The different two seal widths of the Rollprint Clearfoil® Z do not reveal a significant difference under the tested conditions.

Example 7: Blood Containers with Anaerobic Tube Fitments

Collapsible inner blood bags are utilized for testing (model KS-500, KS Mfg., Avon, MA) and utilize PVC films (Renolit ES-3000, Renolit America). The KS-500 blood bag has two transfusion spike ports (Vitalmed #20391, Vitalmed. Inc., Lakeville, MA) and one PVC inlet port adapted to accept standard I.V. inlet tubing having ~4-mm (0.161 inch) O.D.; the blood bags are supplied without any inlet tubing bonded to the inlet port 30. The blood bags are placed in outer barrier bags fabricated from RollPrint Clearfoil® Z film #37-1275 (Rollprint Packaging Products, Inc., Addison, IL) as follows.

For one group of samples an oxygen impermeable fitment adapter (reference NHS #A097-000—"PE wedge") is machined from solid polyethylene having flat tapered sealing surfaces for mating with the barrier film and a through hole in the center for the inlet tubing 30 to pass through. For the other group of samples an oxygen impermeable fitment adapter (reference NHS #A121-000—"Multilayer tube") is made from a trilayer tubing having a polyethylene outer layer 308, for mating with the barrier film, a thin EVA intermediary bonding layer 307, and an inner PVC layer 306, for the inlet tubing to bond to.

Barrier bags about 150 by 270 mm are fabricated from pairs of sheets of Rollprint Clearfoil® Z film by first heat sealing the oxygen impermeable fitment adapter (either PE Wedge version or Multilayer Tube version) into the seam created on one of the short edges of the film pairs using a custom heat sealer having a cutout area to accept the specific type of fitment adapter. The other short edge and one long edge of the barrier bags are then sealed using conventional heat sealing methods and equipment, leaving one long edge of each bag open.

For the PE Wedge samples an 800 mm length of PVC inlet tubing (Qosina #T4306, Qosina Corp., Edgewood, NY) is pushed through the hole in the fitment adapter and pulled through to expose about 25-30 mm inside the barrier bag seam. For the multilayer barrier traversing tube (tube 305) samples a ~750 mm length of PVC inlet tubing (Qosina #T4306, Qosina Corp., Edgewood, NY) is solvent bonded to the exposed end of the multilayer barrier traversing tube 305, outside the barrier bag using cyclohexanone. Another piece of PVC tube about 25-30 mm long is solvent bonded to the end of the multilayer barrier traversing tube 305, inside the barrier bag.

The inner blood bag is then placed inside the barrier bag and the short section of PVC inlet tubing (tubing 304) is solvent bonded into the PVC inlet port (inlet/outlet 30) of the inner blood bag using cyclohexanone. For the PE wedge samples the inlet tube (tubing 304) is bonded in place to the fitment adapter (PE Wedge) with Loctite 4310 adhesive (Henkel Corp., Rocky Hill, CT) and cured with UV light using a spot wand (Dymax PC-3 Lightwelder, Dymax Corp., Torrington, CT). No further bonding of the multilayer barrier traversing tube samples aside from the solvent bonding was performed.

The inlet tubing (tubing 304) on all samples is then heat sealed closed about 150 mm from the fitment adapter and at 50 mm intervals thereafter to create 12 dummy pilot sample segments as required for blood sampling by ISO 3826-1 using a tube sealer (Genesis SE340, Genesis BPS, Ramsey, NJ). Sealing of the remaining long edge of the barrier film is then performed with an impulse heat sealer (Accu-Seal model 530, Accu-Seal, Inc., San Marcos, CA) after squeezing as much air as possible out of the headspace between the bags.

Several such sample blood storage containers are sent to Mocon, Inc. for oxygen permeation testing using an Oxtran 2/21 oxygen permeability instrument (Mocon, Inc., Minneapolis, MN). To understand the sources of oxygen ingress, some samples are tested as prepared; some samples have the inlet tube trimmed off near the fitment face and the inlet tubing I.D. plugged with metalized epoxy; some samples have the inlet tubing (tubing 304) trimmed off and the fitment face/barrier bag seam area masked with metallized epoxy. A pair of each configuration is selected for testing. The test gas is 100% oxygen at 50% R.H. and 760 mmHg pressure, and the carrier gas is 98% nitrogen/2% hydrogen at 100% R.H.; the test is conducted at 23° C. The results of the testing for oxygen ingress (cc/package*day) of 100% $O_2$ is presented in Table 10:

TABLE 10

Oxygen ingress testing of seal adaptors

| Description | Sample # 1 | Sample # 2 |
|---|---|---|
| Full Pouch w/PE Wedge Adapter | 0.275* | 0.880 |
| With Inlet Tube Plugged | 0.275* | 0.0378 |
| With Fitment Masked | 0.149* | 0.027 |
| Full Pouch w/Multilayer Tube Adapter | 0.977 | 0.978 |
| With Inlet Tube Plugged | 0.0192 | 0.0174 |
| With Tube Masked | 0.0185 | 0.0150 |

*Results of sample # 1 with the polyethylene fitment adapter indicate a blockage in the tubing at a point close to the fitment, as well as a potential leak in the oxygen barrier pouch itself caused by the copper tubing used for gas introduction during testing. This leads to inconsistent results.

These results indicate that under ambient conditions (21% $O_2$, 23° C.) the blood container will introduce about 7.7-8.6 cc oxygen over 42 days, and 11.8-13.1 over 64 days, however most of oxygen this ingress is due to the PVC tubing. At the refrigerated temperature of 4° C. used for blood storage, these ingress rates will be greatly reduced. For the anaerobically sealed package with the inlet tube plugged near the seal, only about 0.15-0.24 cc of oxygen ingress is expected over 42 days duration, and about 0.23-0.36 cc oxygen over 64 days.

Example 8: Oxygen Ingress of Tubing

Several samples of PVC inlet tubing (Qosina #T4306, Qosina Corp., Edgewood, NY) are trimmed to either ~150 mm (6 inch) length or ~200 mm (8 inch) length and sealed at one end. In addition, the longer 200 mm samples are sealed again about 50 mm (2 inches) from the sealed end to mimic a pilot sample section. Several such samples are sent to Mocon, Inc. for oxygen permeation testing using an Oxtran 2/21 oxygen permeability instrument (Mocon, Inc., Minneapolis, MN). A pair of each configuration are selected for testing. The test gas is 100% oxygen at 50% R.H. and 760 mmHg pressure, and the carrier gas is 98% nitrogen/2% hydrogen at 100% R.H.; the test was conducted at 23° C. The testing results are presented in Table 11 for oxygen ingress (cc/day) of 100% $O_2$:

TABLE 11

Oxygen ingress testing of PVC inlet tubing

| Description | Sample # 1 | Sample # 2 | Mean |
|---|---|---|---|
| Qosina T4306 tubing 150-mm sealed one end | 0.959 | 0.965 | 0.962 |
| Qosina T4306 tubing 200-mm sealed one end with 50-mm pilot sample | 0.934 | 0.957 | 0.946 |

These results are consistent with the previous blood container testing, and show an oxygen ingress through the PVC tubing at ambient conditions (21% $O_2$, 23° C.) of about 8.2-8.5 cc over 42 days duration, and 12.6-13.0 cc oxygen over 64 days. Under the conditions tested, no substantial difference is observed between the shorter samples without a pilot segment and the longer samples with a pilot segment.

Example 9: Dynamic Oxygen Absorption of Commercial Sorbents

Three exemplary sorbents are tested for their ability to absorb oxygen in a dynamic test. The test chamber consists of a 4 inch diameter by 4 inch length 304 stainless steel quick flange fitting (McMaster Carr #4322K35) with end caps, wherein one end cap is modified for the connection of sensors, nitrogen purge and oxygen test gas inlets. A cylindrical polyethylene insert is made to reduce the interior chamber volume to about 50 cc total volume. A PreSens Fibox 3 Gas Analyzer fitted with a PSt6 oxygen sensor and a PT1000 temperature sensor (PreSens Precision Sensing GmbH, Regensburg, Germany) are used for the testing.

The system is purged with a 1% oxygen/balance nitrogen gas mixture and then a 100% nitrogen gas for two-point calibration before use. A sachet of the sorbent 207 under test is placed in the system in a nitrogen atmosphere glove box, the system sealed (cover clamped in place) and then purged with 100% nitrogen before removing from the glove box. A syringe pump with a Hamilton gas tight syringe is filled with >5 cc of 100% oxygen; the syringe line to the test chamber is purged by activating the syringe pump, leaving 5 cc of oxygen in the syringe. The syringe line valve is closed and connected to the system. The dynamic test is started by activating the syringe pump to inject 5 cc of oxygen over a period of 60 minutes. After 60 minutes the syringe pump line valve is closed and the sorbent allowed to continue to absorb the residual oxygen in a static test.

The test is performed at ambient conditions (23° C.) using a single sachet each of the following commercially available iron-based oxygen scavengers: Mitsubishi Gas Chemical America (MGC) Ageless® SS-200 sorbent (200 cc capacity, designed to work in cold environments), O-Buster® (300 cc capacity, standard grade) (Hsiao Sung Non-Oxygen Chemical Co., Ltd., Taiwan), and Sorbent Systems LTECC1K500CS (1000 cc capacity, "fast acting"—designed to work in cold environments) (Impak Corp., Los Angeles, CA).

Figure 11:
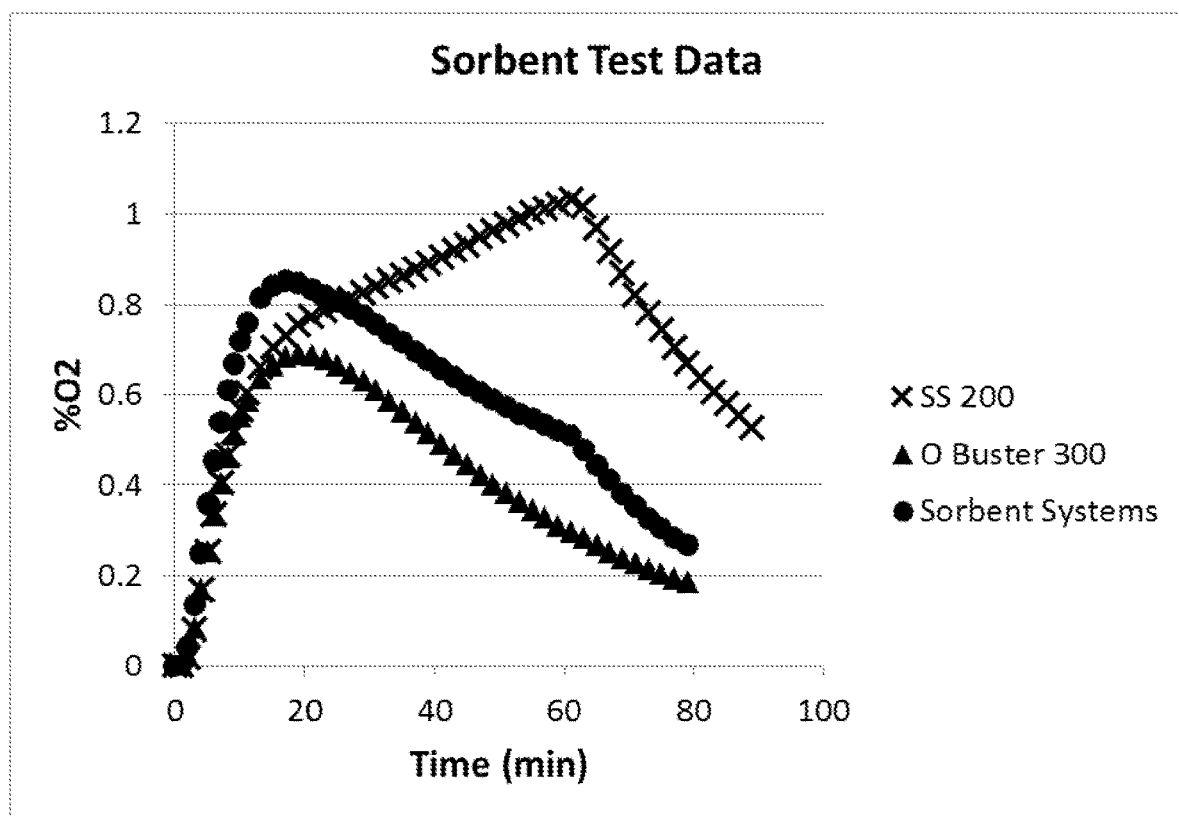
FIG. 11 presents a graphical presentation of sorbent test data according to example 9.

FIG. 11 shows that the introduction of oxygen rises to about 0.7-0.8% oxygen in about 10 minutes for each type of sorbent. At about 10-15 minutes both the O-Buster® and Sorbent Systems sorbents are able to reduce the level of oxygen in the system from about 0.75% to about 0.3-0.5% oxygen. The SS-200 sorbent is not able to reduce the oxygen level, which continued to increase up to about 1% oxygen at 60 minutes.

After 60 minutes, when the dynamic introduction of oxygen is terminated and the system is under static test, all sorbents showed continued reduction of the oxygen level. The SS-200 shows a dramatic increase in the rate of oxygen reduction under static conditions, whereas the Sorbent Systems sorbent shows a slight increase in the rate of oxygen reduction under static conditions; the O-Buster® sorbent shows no difference in the rate of oxygen reduction under static conditions. It is noted that the capacity of the sorbents, as claimed by the manufacturers, do not appear to have a direct impact on the rate of oxygen absorption, as evidenced by the relative performance of the 300 cc O-Buster® sorbent compared to the 1000 cc capacity Sorbent Systems sorbent. The two sorbents formulated to perform well in cold conditions (MGC SS-200 and Sorbent Systems LTECC1K500CS), as claimed by the manufacturers, did appear to perform more poorly than the standard O-Buster® sorbent. Test data is not performed or collected at temperatures other than 23° C.

Example 10: Dynamic Oxygen Absorption of Commercial Hand Warmers

Several commercially available hand warmers are tested for their ability to absorb oxygen in a dynamic test, using the same system and conditions as described in Example 9 above. Hand warmers are iron-based oxygen scavengers designed to react with ambient oxygen and generate heat. The iron-based chemistry is the same of commercially available sorbents used for food preservation as tested in Example 9, but the formulations may vary slightly to modify the kinetics of the reactions.

Figure 12:
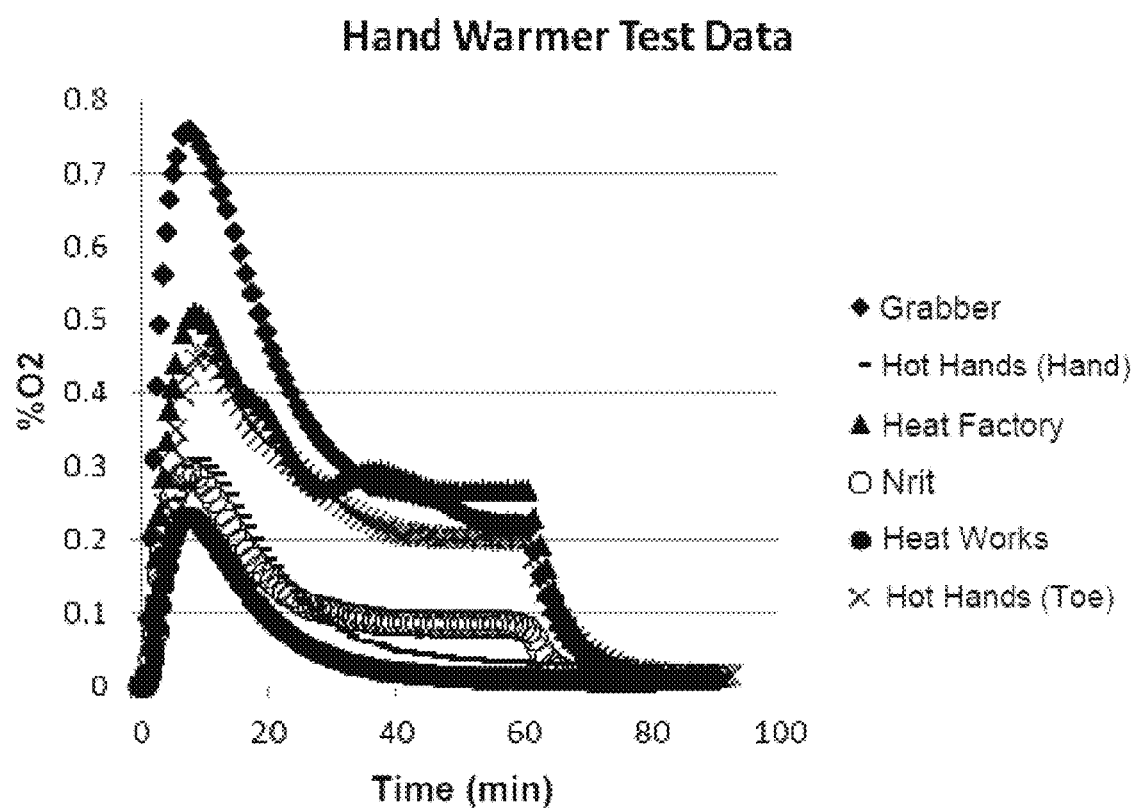
FIG. 12 presents a graphical presentation of hand warmers test data according to example 10.

FIG. 12 shows the data for several commercially available hand warmers tested as described above. The data shown in the table below shows that the introduction of oxygen raises the level to about 0.25% to about 0.75% oxygen in about 10 minutes, depending on the type of hand warmer. At about 10-15 minutes the data shows that all of the hand warmers are able to quickly reduce the oxygen level from the peak values, with noticeable variations between formulations. Most of the formulations appear to approach a steady state during the dynamic test, except for the Hot Hands (hand) and the Heat Works versions, which continued to reduce the oxygen levels to near zero under dynamic test conditions.

After 60 minutes, when the dynamic introduction of oxygen is terminated and the system is under static test, all sorbents showed a dramatic reduction of the oxygen level to near zero values, except for the Hot Hands (hand) and the Heat Works versions, which are already at near zero oxygen. These results show that the formulations used for the hand warmers have a faster rate of oxygen absorption than the food grade oxygen sorbents shown in Example 9, and are able to achieve lower oxygen levels over the period of study and conditions used in this test.

Example 11: Fabrication of Anaerobic Storage Bags

Several Anaerobic Storage Bags are fabricated as described in examples 1 and 2 above, and further completed by incorporating a sachet of SS-200 sorbent (Mitsubishi Gas Chemical America, New York, NY), a plastic spacer, and an oxygen sensor tab (Mocon, Inc., Minneapolis, MN) before heat sealing the final edge in a nitrogen atmosphere glove box. In addition, several Anaerobic Storage Bags were fabricated using Renolit ES-4000 PVC-Citrate and also using silicone sheets (McMaster Carr #87315K61, McMaster Carr, Robbinsville, NJ) to fabricate the inner collapsible blood container 202. The headspace oxygen level is measured through the outer receptacle film (Rollprint Clearfoil® Z) for several days after fabrication to verify the robustness of the seals. The results are shown in Table 12 to Table 14 below.

TABLE 12

ASB fabricated with Renolit ES-3000 Inner blood bag (Headspace oxygen in Torr)

| ASB # | Day 0 | Day 1 | Day 2 | Day 3 | Day 4 | Day 5 |
|---|---|---|---|---|---|---|
| 1 | 4.52 | 0.39 | 0.43 | 0.53 | 0.49 | 0.47 |
| 2 | 5.85 | 0.43 | 0.56 | 0.76 | 0.63 | 0.87 |
| 3 | 5.83 | 0.64 | 0.42 | 0.37 | — | — |
| 4 | 2.41 | 0.62 | 0.40 | 0.34 | 0.44 | 0.35 |
| 5 | 5.36 | 0.63 | 0.43 | 0.37 | — | — |
| 6 | 5.07 | 0.75 | 0.34 | 0.46 | 0.45 | 0.42 |
| 7 | 3.15 | 0.63 | 0.35 | 0.46 | 0.44 | 0.42 |
| 8 | 6.07 | 0.63 | 0.51 | 0.33 | 0.37 | 0.29 |
| 9 | 5.39 | 0.50 | 0.38 | 0.35 | 0.36 | 0.28 |
| 10 | 3.24 | 0.78 | 0.75 | 7.50 | 4.36 | 1.90 |
| 11 | 5.30 | 0.49 | 0.44 | 0.43 | 0.47 | 0.31 |
| 12 | 2.79 | 0.62 | 0.43 | 0.36 | 0.44 | 0.42 |

TABLE 13

ASB fabricated with Renolit ES-4000 Inner blood bag (Headspace oxygen in Torr)

| ASB # | Day 0 | Day 1 | Day 2 | Day 4 |
|---|---|---|---|---|
| 1 | 4.52 | 0.18 | 0.03 | 0.00 |
| 2 | 5.85 | 0.19 | 0.02 | 0.01 |
| 3 | 5.83 | 0.26 | 0.06 | 0.03 |
| 4 | 2.41 | 0.17 | 0.00 | 0.01 |
| 5 | 5.36 | 0.32 | 0.02 | 0.00 |
| 6 | 5.07 | 0.22 | 0.01 | 0.00 |
| 7 | 3.15 | 2.12 | 27.85 | 12.00 |
| 8 | 6.07 | 0.28 | 0.06 | 0.05 |
| 9 | 5.39 | 0.38 | 0.15 | 0.10 |
| 10 | 3.24 | 0.20 | 0.11 | 0.09 |

TABLE 14

ASB fabricated with Silicone Inner blood bag (Headspace oxygen in Torr)

| ASB # | Day 0 | Day 1 | Day 2 | Day 4 |
|---|---|---|---|---|
| 1 | 7.23 | 0.00 | 0.00 | 0.00 |
| 2 | 6.90 | 0.00 | 0.00 | 0.00 |
| 3 | 8.03 | 0.00 | 0.00 | 0.00 |
| 4 | 7.92 | 0.00 | 0.00 | 0.00 |
| 5 | 7.81 | 0.00 | 0.00 | 0.00 |
| 6 | 8.03 | 0.00 | 0.00 | 0.00 |
| 7 | 4.75 | 0.00 | 0.00 | 0.00 |
| 8 | 4.76 | 0.00 | 0.00 | 0.00 |
| 9 | 3.96 | 0.00 | 0.00 | 0.00 |
| 10 | 3.94 | 0.00 | 0.00 | 0.00 |

The mean oxygen level at day 0 is significantly higher for the silicone inner blood bag group vs. both of the PVC blood bag groups, with means of 6.33 Torr vs. 4.58 Torr (ES-3000) and 4.69 Torr (ES-4000), with $p<0.05$. The results also indicate that the sorbents are able to effectively reduce the headspace oxygen levels to less than 1 Torr oxygen, except in the case of sample #10 in the ES-3000 group and sample #7 in the ES-4000 group. Upon closer examination of the seals on these samples, a small crease or wrinkle is observed in the seam of the final seal.

Example 12: Intermediary Seal Adaptor 301 with Multilayer Barrier Traversing Tubes for Solvent Bonding of Tubing An anaerobic storage container with a substantially impermeable joint having fluid connectivity is fabricated by first insert molding 3 pieces of multilayer barrier traversing tubing 305 into polyethylene (Dowlex™ 2517) in the shape of a bar about 5 mm wide by about 57 mm total length with tapered ends ("diamond wedge", a seal adaptor 301) (Sonicron Corp., Westfield, MA). The multilayer barrier traversing tubes have a polyvinylchloride (PVC) inner layer 306, suitable for solvent bonding to PVC tubing, a polyethylene (PE) outer layer 308, suitable for heat bonding to PE and other heat weldable films, and an intermediary ethylvinylacetate (EVA) layer 307, suitable for achieving bonding between the PVC and PE layers (Extrusion Alternatives, Inc., Portsmouth, NH). The multilayer barrier traversing tubes 305, are suitably sized in inner diameter to accommodate solvent bonding to either standard PVC blood line transfer tubing of about 3.0 mm by about 4.1 mm according to ISO 3826-1:2013, or a blood transfer device such as a PVC spike port, for example Vitalmed #20391 (Vitalmed, Inc., Lakeville, MA) or Qosina #65842 (Qosina Corp., Edgewood, NY). The barrier traversing tubes 305 extend beyond the width of the diamond wedge by about 25 mm on both sides to facilitate these connections.

The diamond wedge with insert-molded multilayer tubes is placed between a pair of barrier films (RollPrint ClearFoil® Z, RollPrint Packaging Products Inc., Addison, IL) on a custom fabricated heat sealing die having a groove suitably sized and shaped to accept the diamond wedge shape and provide slight compression during heat sealing, which is performed on a modified Franklin model 2400 press (Franklin Mfg. Corp., Norwood, MA). The dies are constantly heated to about 140° C. by a pair of internal cartridge heaters (McMaster Carr #4877K143, McMaster Carr, Inc., Robbinsville, NJ) connected to a process controller (Omega model CNI-CB120-SB, Omega Engineering, Inc., Stamford, CT). The press is activated with the films and diamond wedge in the die to compress and heat the assembly for about 3-4 seconds to yield a completely sealed seam comprising one side of the outer receptacle 201.

One end of each multilayer tube is then solvent bonded to a transition PVC tube to connect a flexible collapsible blood container 202 inside the outer receptacle 201, and the other end of each multilayer tube is then solvent bonded to either a spike port or a section of standard blood line transfer tubing. A sachet of sorbent is then placed on a spacer sheet, which is then placed between the collapsible container and one of the outer receptacle films, and then the remaining three seams of the outer receptacle 201 are sealed using an impulse sealer to yield a completed anaerobic blood storage container.

Figure 3D:
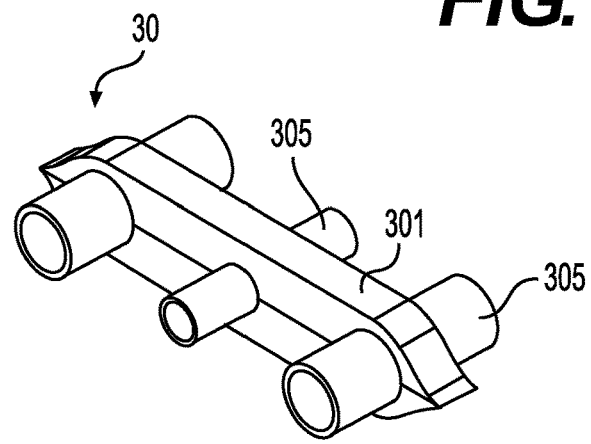
FIG. 3D is an illustration of an exemplary embodiment of a manifold 301 with 3 inlet/outlet ports to hold barrier traversing tubes 305.

Example 13: Intermediary Block Insert Molded with Bilayer Tubes for RF Welding of Tubing Similar to example 12 above, an anaerobic storage container with a substantially impermeable inlet/outlet 30 having fluid connectivity is fabricated by first insert molding 3 pieces of barrier traversing tubing 305 into polyethylene (Dowlex™ 2517) in the shape of a bar about 5 mm wide by about 57 mm total length with tapered ends ("diamond wedge") (Sonicron Corp., Westfield, MA), as shown in FIG. 3D.

In this example, however, the barrier traversing tube of example 12 is replaced with a bilayer barrier traversing tube comprised of a polyvinylchloride (PVC) inner layer 306, and an outer EVA layer 307, 308 (Extrusion Alternatives, Inc., Portsmouth, NH). Since EVA is known to have both good RF (radiofrequency) and heat weldability, and good adhesion to both PVC and PE, the need for any transition connection tubes to the collapsible blood container are eliminated in this configuration. The thickness of the EVA outer layer can be varied as desired and need only meet a minimum thickness to ensure adhesion of the PVC during insert molding to the PE; that is about 0.05-0.10 mm minimum thickness. The bilayer tubes are also similarly sized in inner diameter according to example 12 and extend beyond the width of the diamond wedge by about 25 mm on both sides to facilitate connections, however, the outer diameter of the bilayer tubes are suitably sized to fit into RF welding dies for use in fabricating a collapsible blood container.

In the first step of assembly the tubes on one end of the insert molded diamond wedge are RF welded to PVC films to form a collapsible blood container as follows: the three tubes in the diamond wedge are placed onto brass mandrels to support each of them, and then placed between a pair of collapsible blood container 202 films (Renolit ES-3000, American Renolit Corp., City of Commerce, CA). The assembly is then placed onto a custom RF sealing die 70 having three grooves suitably sized and shaped to accept the three tubes. The RF sealing die also seals the PVC collapsible blood container films between the tubes, and the perimeter seal in the outline shape of the collapsible blood container 202. The press is activated with the films and tubes in the dies to compress and heat the assembly for about 4-5 seconds by RF energy (Solidyne RF Welder, S/N 3657) to yield a completely sealed seam forming the collapsible blood container 202, which also has a substantially impermeable joint (diamond wedge) in place around the fluidly connected inlet tubes ready for sealing to the barrier films of the outer receptacle 201 in the next step.

Similar to example 12, the collapsible blood container RF welded to the tubes of the diamond wedge is now placed between a pair of barrier films (RollPrint ClearFoil® Z, RollPrint Packaging Products Inc., Addison, IL). The assembly is placed onto a custom fabricated heat sealing die and sealed on the Franklin press to yield a completely sealed seam comprising one side of the outer receptacle 201, plus the fluidly connected collapsible blood container. In the remaining steps the spike ports and PVC blood inlet tubing (inlet/outlet 30) are solvent bonded to the exposed remaining sections of bilayer tubes of the diamond wedge as in example 12, and the sorbent sachet and spacer are also similarly prepared before sealing the remaining three seams of the outer receptacle 201, to yield a completed anaerobic blood storage container.

Figure 4A:
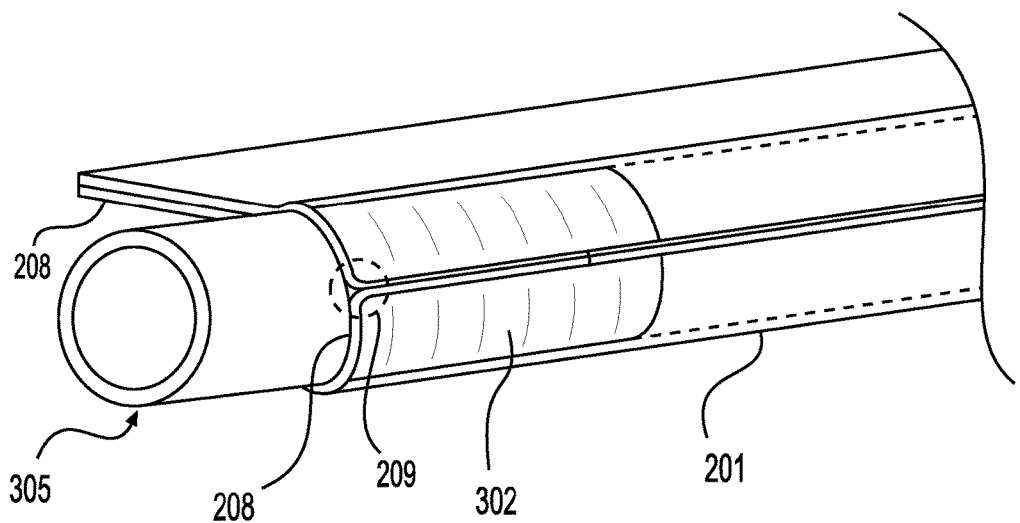
FIG. 4A is an illustration of a bonding layer joining a barrier traversing tube 305 onto membrane 208 and creating a bond 302 with gap 209.

Example 14: Barrier Traversing Tubes Heat Sealed "3-at-Once" for Solvent Bonding Tubing An anaerobic storage container with a substantially impermeable joint having fluid connectivity is fabricated by simultaneously heat sealing three individual pieces of barrier traversing tubing between a pair of barrier films (RollPrint ClearFoil® Z, RollPrint Packaging Products Inc., Addison, IL), as shown in FIG. 4A. The barrier traversing tubes have a polyvinylchloride (PVC) inner layer 306, suitable for solvent bonding to PVC tubing, a polyethylene (PE) outer layer 308, suitable for heat bonding to PE and other heat weldable films, and an intermediary ethylvinylacetate (EVA) layer 307, suitable for achieving bonding between the PVC and PE layers (Extrusion Alternatives, Inc., Portsmouth, NH). The barrier traversing tubes are suitably sized in inner diameter to accommodate solvent bonding to either standard PVC blood line transfer tubing of about 3.0 mm by about 4.1 mm according to ISO 3826-1:2013, or a blood transfer device such as a PVC spike port, for example Vitalmed #20391 (Vitalmed, Inc., Lakeville, MA) or Qosina #65842 (Qosina Corp., Edgewood, NY).

The barrier traversing tubes are solvent bonded to a short section of PVC tubing using cyclohexanone to connect each tube to the respective port on a collapsible blood container. Mandrels are inserted into the barrier traversing tubes, a sorbent sachet (Mitsubishi SS-200, Mitsubishi Gas Chemical America, Inc., NY, NY) is placed on a spacer sheet and the assembly is held between a pair of barrier films (Roll-Print ClearFoil® Z, RollPrint Packaging Products Inc., Addison, IL) on a custom fabricated heat sealing die. The sealing die (aluminum die 70) has three grooves suitably sized by reducing the diameter by about 0.25 mm and suitably shaped by providing a 0.5-0.8 mm radius to the corners to accept the tubes and provide slight compression during heat sealing. The sealing process is performed on a modified Franklin model 2400 hot stamp press (Franklin Mfg. Corp., Norwood, MA) at 80-85 psig. The upper die 701 is fabricated from a solid block of aluminum machined into a complimentary shape slightly larger than the perimeter of the collapsible blood container. The center region of the upper die 705 is relieved to accept and nest the collapsible blood container 202, and the die has grooves as described above for sealing the barrier traversing tubes. The upper die is heated by direct conduction to about 127° C. by mounting the upper die to the heated top platen of the Franklin press.

The lower die 702 is comprised of a metal insert section surrounded by thermally insulating Garolite® G-10 material. The lower die is similarly shaped as compared to the upper die, providing a nest for the collapsible blood container 202 and a flat mating surface 705 for the upper die to press against, while the metal insert section provides the grooves needed for sealing the barrier traversing tubes to the surrounding films to ensure a substantially impermeable seal. The lower die is constantly heated to about 132° C. by an internal cartridge heater (McMaster-Carr P/N: 3618K412) connected to process controller (Omega model CNI-CB120-SB, Omega Engineering, Inc., Stamford, CT). Thus, the entire perimeter is heated from the top die and also from the insert portion 706 of the lower die.

The press is activated with the films, sorbent and spacer sheet, and tubes in place in the dies as described and held for about 2 seconds dwell time to yield a completely sealed seam on the outer receptacle 201, having three barrier traversing tubes with substantially impermeable seals fluidly connected to the collapsible blood container 202 inside. The remaining end of each barrier traversing tube is then solvent bonded to either a spike port or a section of standard blood line PVC tubing (inlet/outlet 30) to yield an anaerobic blood storage container.

Figure 4B:
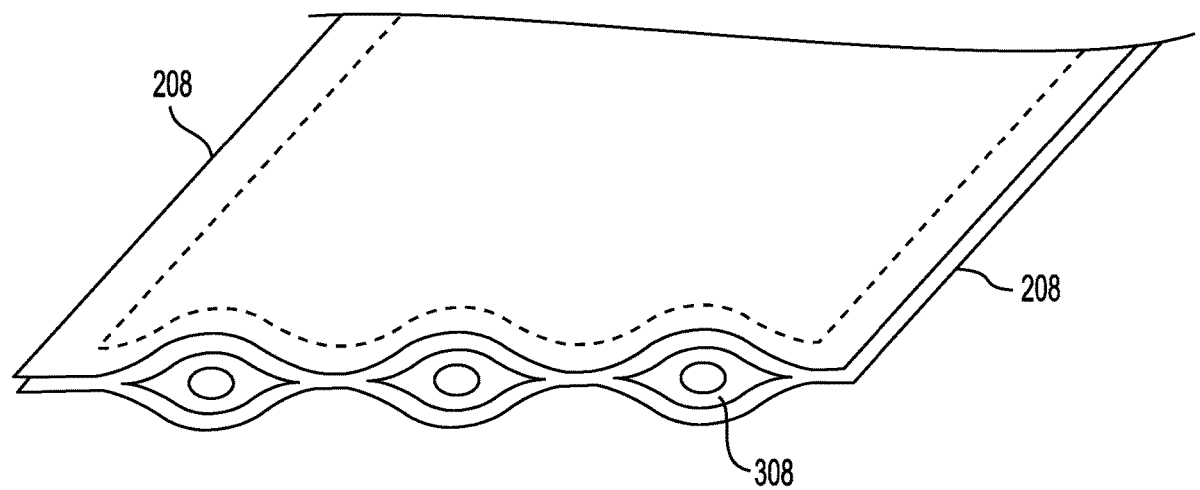
FIG. 4B is an illustration of a bonding layer joining multilayer barrier traversing tubes 305 with membrane 208.
Figure 5A:
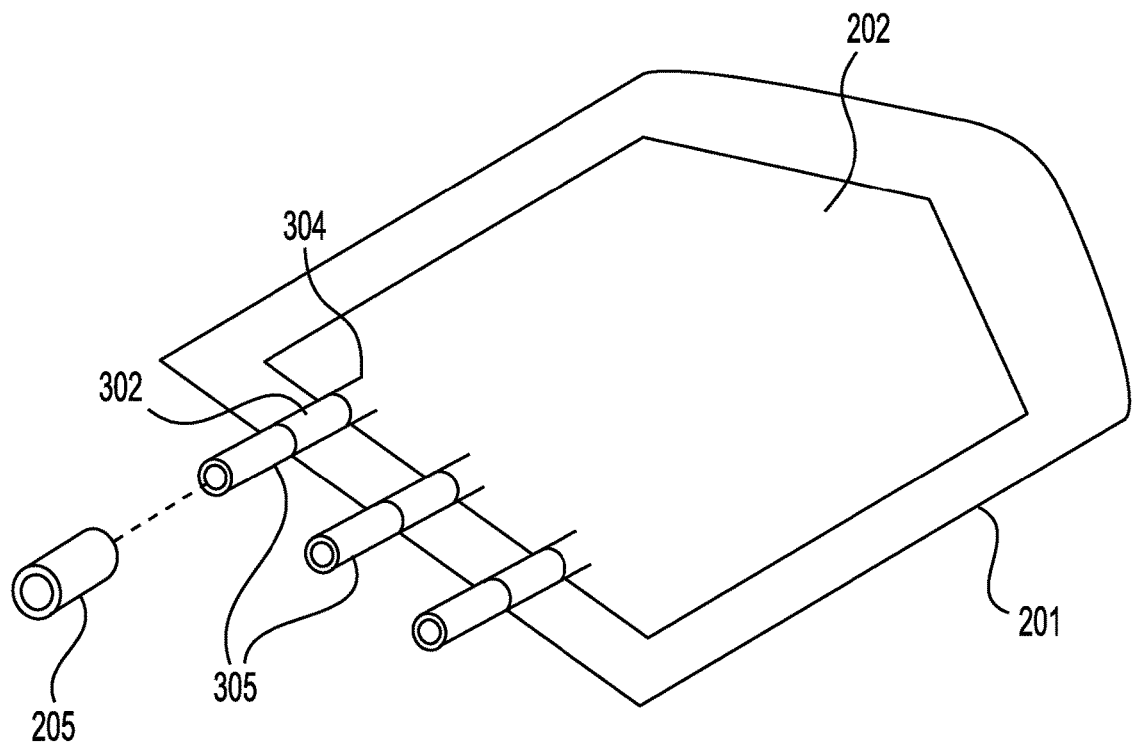
FIG. 5A is an illustration of a blood storage device with barrier traversing tubes 305 bonded to create bond 302 according to an aspect of the present disclosure.
Figure 5B:
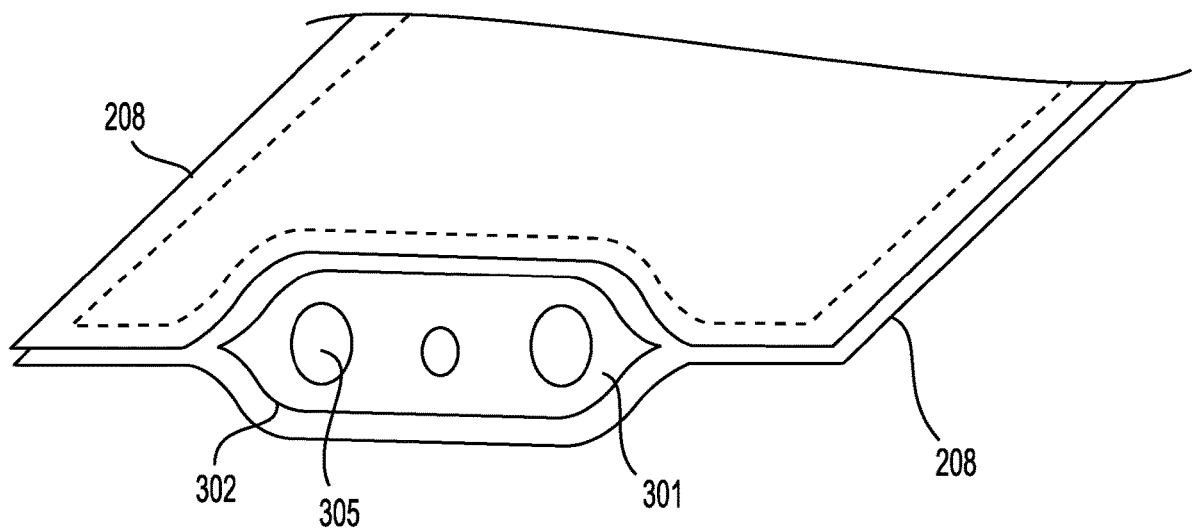
FIG. 5B is an illustration of a blood storage device with bonding layer 302 joining manifold 301 with membrane 208.

Example 15: Extruded Shape Barrier Traversing Tubes Heat Sealed "3-at-Once" for Solvent Bonding Tubing Similar to example 14 above, an anaerobic storage container with a substantially impermeable joint having fluid connectivity is fabricated by simultaneously heat sealing three individual pieces of barrier traversing tubing between a pair of barrier films (RollPrint ClearFoil® Z, RollPrint Packaging Products Inc., Addison, IL). In this example the barrier traversing tubes have an outer layer of PE that is extruded in a diamond wedge shape, as shown in FIG. 4B, rather than a round shape to facilitate edge sealing to the barrier film; the inner PVC layer retains a round inner diameter suitable for solvent bonding with other PVC tubing and fitments, such as a spike port.

Example 16: Individual Insert Molded Intermediary Blocks

Similar to example 12 and 14 above, an anaerobic storage container with a substantially impermeable joint having fluid connectivity is fabricated by simultaneously heat sealing three individual diamond wedges, each having only one barrier traversing tube insert molded therein, between a pair of barrier films (RollPrint ClearFoil® Z, RollPrint Packaging Products Inc., Addison, IL). In this embodiment the barrier traversing tube 305 has an inner layer 306 of PVC, an intermediary layer 307 of EVA, and an outer layer 308 of PE that is insert molded into a PE diamond wedge shape to facilitate edge sealing to the barrier film; the inner PVC layer retains a round inner diameter suitable for solvent bonding with other PVC tubing and fitments, such as a spike port. Alternatively, the barrier traversing tube 305 can have an inner layer 306 of PVC and an outer layer 308 of EVA, similar to example 13 above.

Example 17: Inner PVC Storage Bags Allow for Blood Reoxygenation

Several inner PVC storage bags are fabricated as described in example 1 and containing a single traditional inlet. The extent of reoxygenation of blood during storage in the inner PVC storage bags is determined by transferring 330 ml packed pRBC having an initial SO2 of between 35 to 70% into the bags. The PVC bags containing the pRBC are placed at 4° C. under ambient atmospheric conditions. Samples are removed from each bag at 1 and 6 weeks and the SO2 determined.

Figure 13:
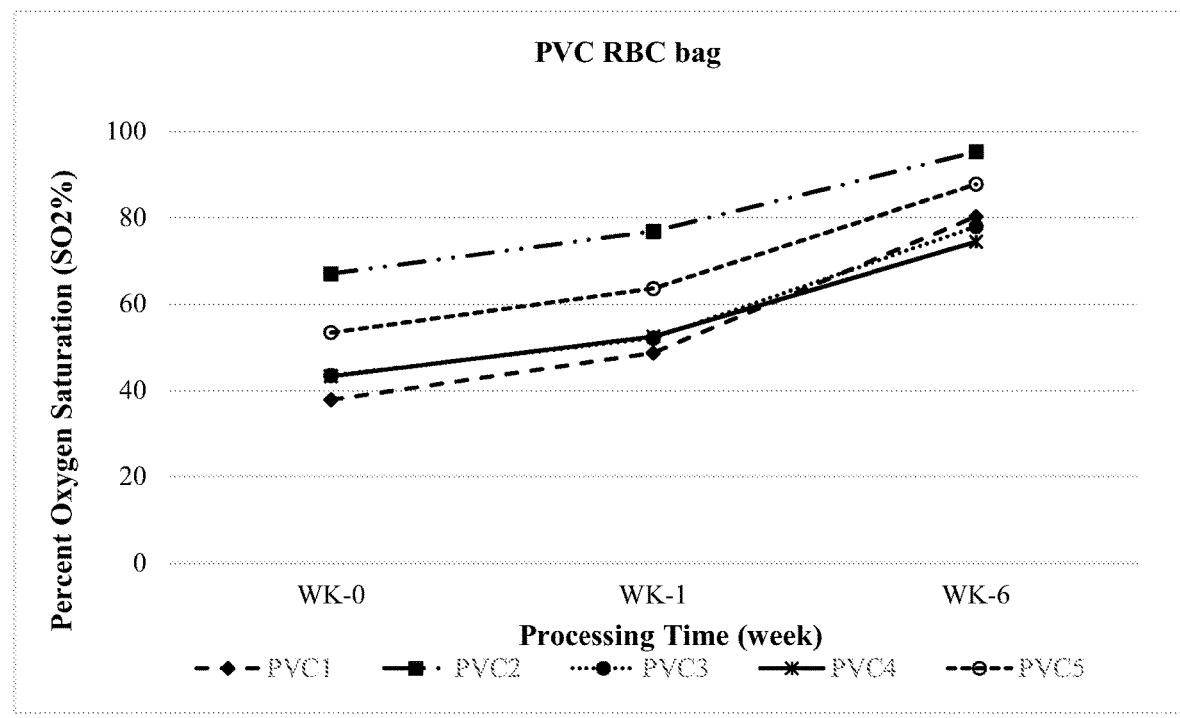
FIG. 13 presents a graphical presentation of oxygen absorption that occurs in non-depleted blood during storage in conventional storage bags without an outer receptacle 201.

The results presented in FIG. 13 show reoxygenation of blood occurs in all inner PVC storage bags.

Example 18: Reoxygenation in the Absence of a Sorbent

Figure 14:
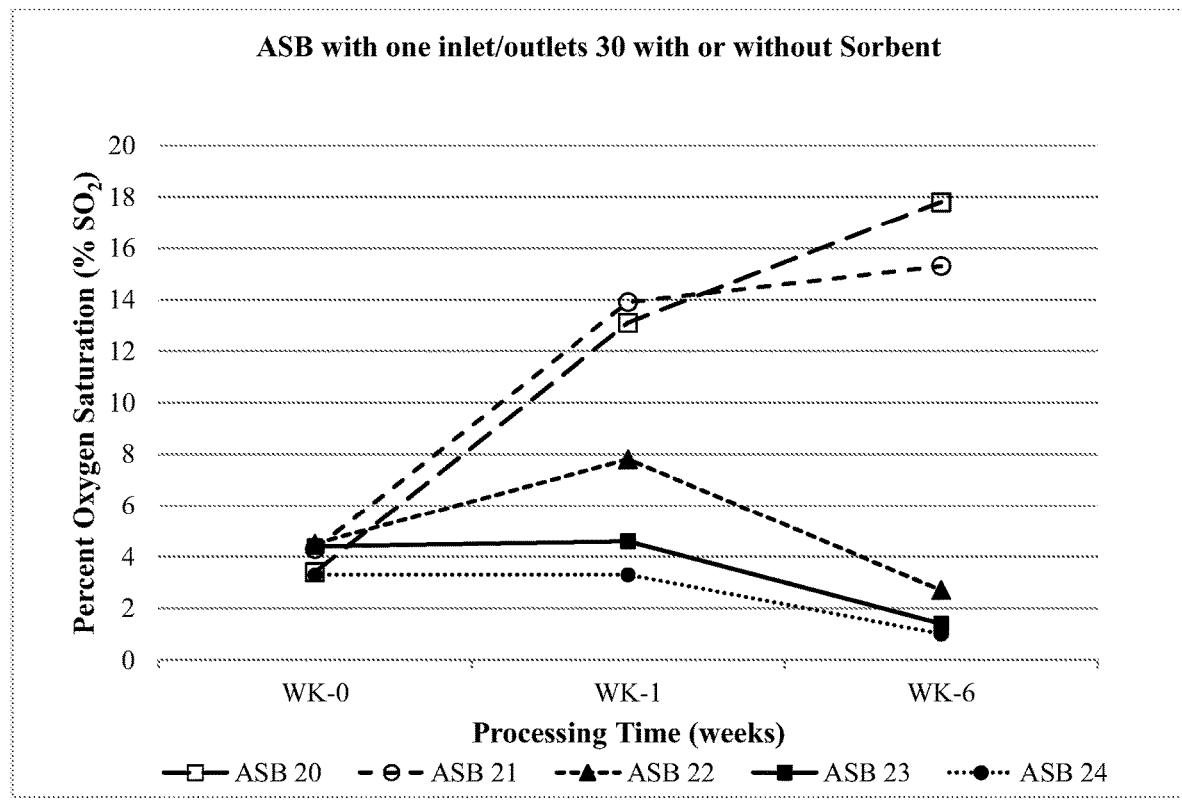
FIG. 14 presents a graphical presentation of oxygen absorption that occurs in an anaerobic storage container with sorbent (filled symbols) or without a sorbent.

Five anaerobic storage bags 20 are fabricated as described in examples 1 and 2 above. Two of the five bags are further completed by incorporating a sachet of SS-200 sorbent (Mitsubishi Gas Chemical America, New York, NY). The extent of reoxygenation of blood during storage in the Anaerobic Storage Bags is determined by transferring 330 ml pRBC having an initial SO2 of approximately 5% into the anaerobic storage bags 20. Samples are removed from each bag at 1 and 6 weeks and the SO2 determined. As presented in FIG. 14, the anaerobic storage bags 20 containing the sorbent result in decreased SO2 compared to the anaerobic storage bags 20 without sorbent, which result in reoxygenation to approximately 15% by week 6.

Example 19: Blood Storage Bags Having Three Inlet/Outlets Lacking an Oxygen Impermeable Bond 302 According to the Present Disclosure (Two Spike Ports and One Blood Line)

Five anaerobic storage bags 20 are fabricated by first RF welding two Renolit ES-3000 sheets, with a thickness that is approximately 0.017 inch and three (3) PVC tubes, without an impermeable bond 302, to form an inner collapsible bag 202.

The inner collapsible bag with 3 inlet/outlet tubes is heat sealed to an outside barrier bag fabricated from RollPrint Clearfoil® Z film #37-1275 (Rollprint Packaging Products, Inc., Addison, IL).

Figure 15:
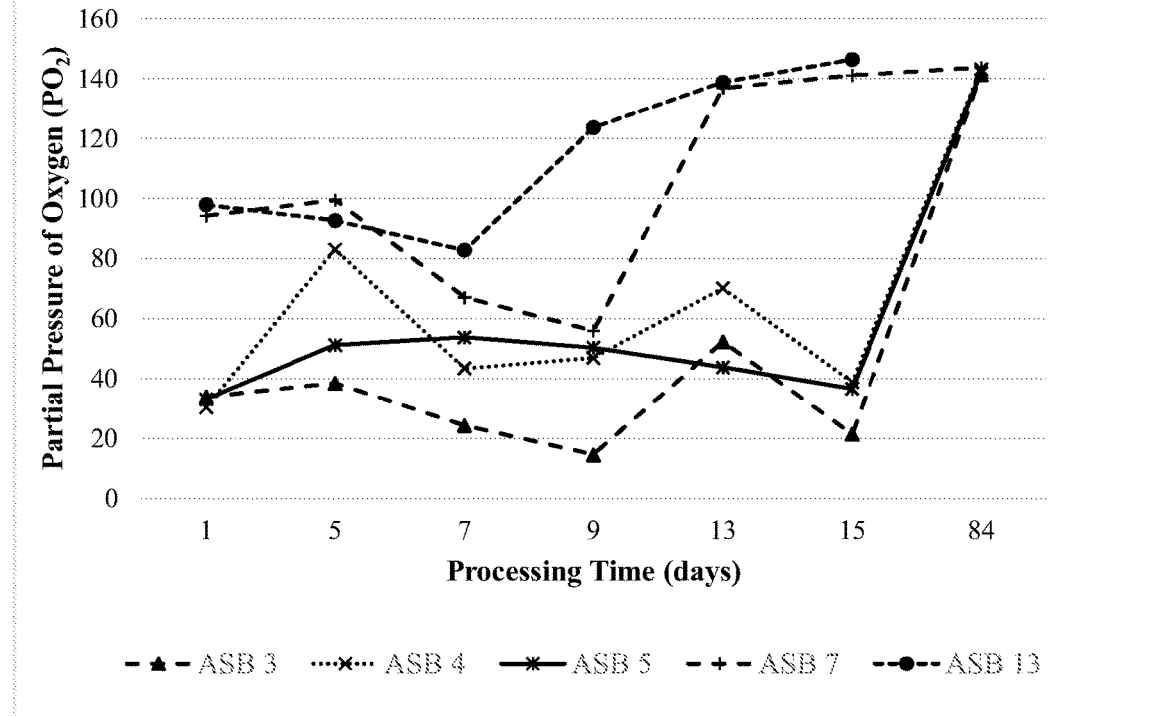
FIG. 15 presents a graphical presentation of partial pressure of oxygen in an anaerobic storage container with three inlet/outlets according to the prior art that is not substantially impermeable to oxygen.

The headspace oxygen level is measured through the outer receptacle 201 film (Rollprint Clearfoil® Z). As shown in FIG. 15, all anaerobic storage bags 20 lacking three oxygen impermeable bonds 302 provided by the present disclosure present highly variable levels of oxygen over the measurement period (84 days) and are not suitable for anaerobic storage of blood.

Example 20: ASB with Three Inlet/Outlets 30 (Two Spike Ports and One Blood Line)

Three anaerobic storage bags 20 are fabricated as by first RF welding two Renolit ES-3000 sheets, with a thickness that is approximately 0.017 inch and three (3) PVC tubes, with a length of approximately 0.75 inch to form the inner collapsible bag 202. Multilayer barrier traversing tubing (with an inner PVC layer 306, intermediate EVA layer 307, and outer PE layer 308) is solvent bonded to each outside diameter of the three (3) PVC tubes of the inner bag to provide the means to heat sealing the inner (PVC) bag to the outer (PE) barrier bag. The multilayer tubing is solvent bonded to the inner bag PVC tubes directly.

Figure 9:
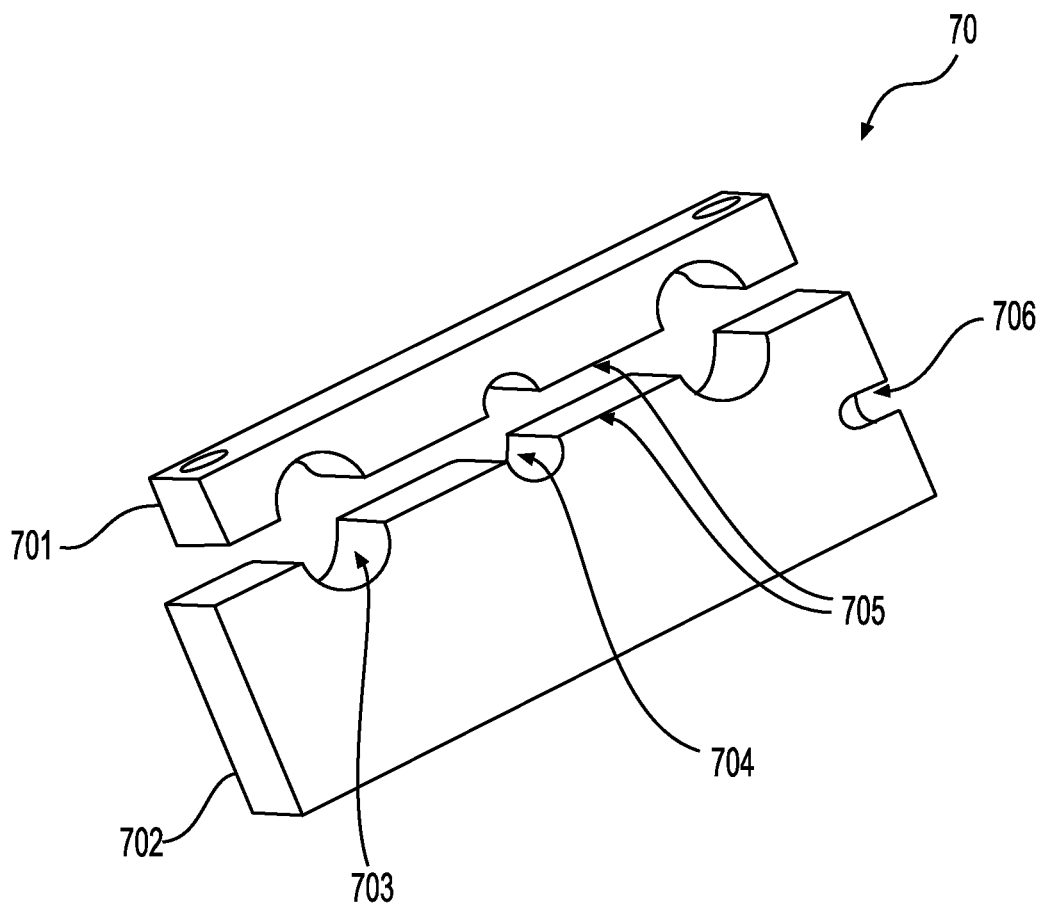
FIG. 9 illustrates an aluminum die 70, according to an aspect of the present disclosure.

The inner collapsible bag with three multilayer barrier traversing tubes 305 is heat sealed to an outside barrier bag fabricated from RollPrint Clearfoil® Z film #37-1275 (Rollprint Packaging Products, Inc., Addison, IL), using an aluminum die 70 (as shown in FIG. 9) that is mounted to the Franklin hot stamping press and a bottom G-10 base with an aluminum insert block to seal around the three (3) ports and seal the inner PVC bag 202 to the outer barrier bag 201.

As shown in FIG. 9, the aluminum die 70 features two (2) aluminum insert blocks, one mounted to the top aluminum part and the bottom G-10 block. The top aluminum block is heated by the Franklin press and the bottom block is heated by a heating rod (¼" diameter) connected to the temperature controller. The tool has alignment pins on the top half and matting bushing on the bottom half to provide alignment between the two halves.

Figure 16:
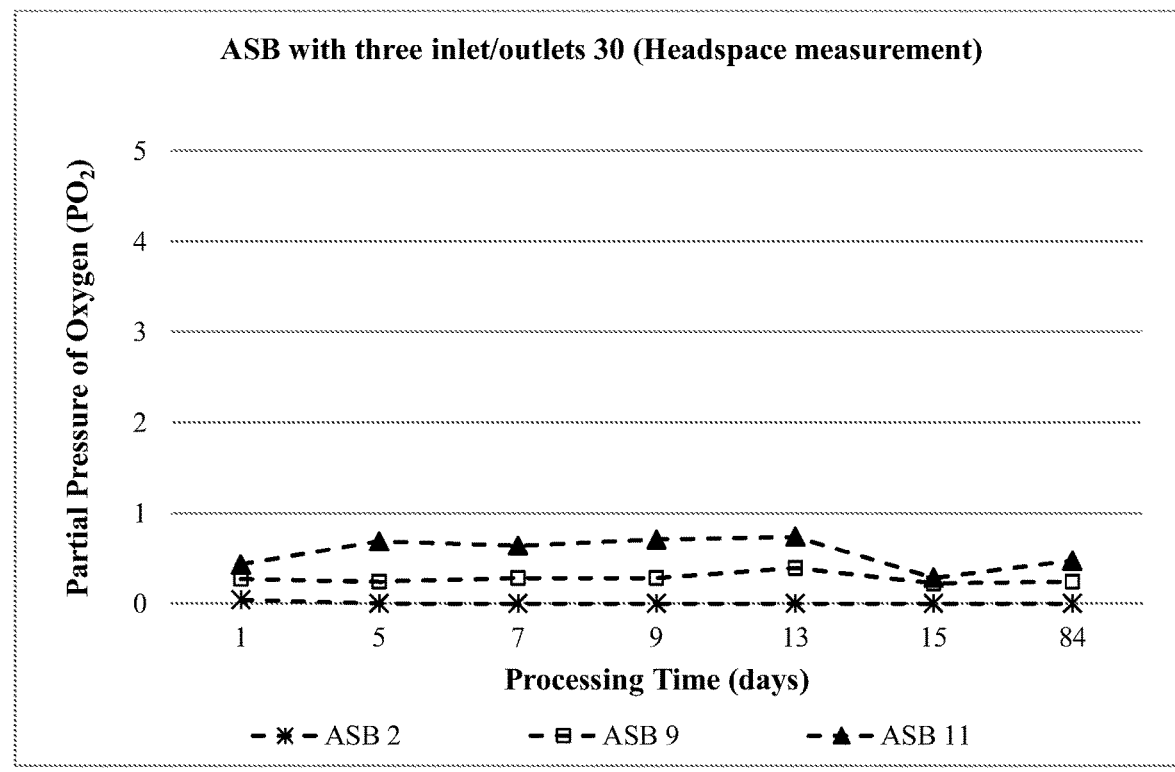
FIG. 16 presents a graphical presentation of partial pressure of oxygen in an anaerobic storage container with three inlets/outlets 30 having barrier traversing tubes 305.

The headspace oxygen level is measured through the outer receptacle 201 film (Rollprint Clearfoil® Z). As shown in FIG. 16, all anaerobic storage bags 20 maintained a headspace of below 0.8 mmHg for up to 84 days.

While the invention has been described with reference to preferred aspects, it will be understood by those skilled in the art that various changes may be made and equivalents may be substituted for elements thereof to adapt to particular situations without departing from the scope of the invention. Therefore, it is intended that the invention not be limited to the particular aspects disclosed as the best mode contemplated for carrying out this invention, but that the invention will include all aspects falling within the scope and spirit of the appended claims.

The invention claimed is:

1. A blood storage device 20 for storing oxygen depleted blood comprising:
    an outer receptacle 201 substantially impermeable to oxygen;
    an inner collapsible blood container 202 comprising polyvinyl chloride (PVC) doped with a plasticizer;
    at least one inlet/outlet 30 that is substantially impermeable to oxygen passing through said outer receptacle 201 and that is in fluid communication with said inner collapsible container 202; and
    an oxygen sorbent 207 situated within said outer receptacle 201,
    wherein said at least one inlet/outlet 30 comprises a unitary tube that is substantially impermeable to oxygen comprising tubing 304, a bond 302, and tubing 205, wherein said unitary tube is a barrier traversing tube 305 comprising an outer layer 308, an inner layer 306, and an intermediate oxygen barrier layer 307.

2. The blood storage device of claim 1, wherein said plasticizer is citrate.

3. The blood storage device of claim 1, wherein said plasticizer is bis (7-methyloctyl) cyclohexane-1,2-dicarboxylate (DINCH).

4. The blood storage device of claim 1, wherein said outer receptacle 201 consists of a heat sealable polyethylene (PE) inner layer, an alumina barrier middle layer, and a polyethylene terephthalate (PET) outer layer.

5. The blood storage device of claim 1, wherein said outer receptacle 201 comprises polyethylene terephthalate (PET).

6. The blood storage device of claim 4, wherein said PET further comprises a barrier coating of silica or alumina.

7. The blood storage device of claim 1, wherein said outer receptacle further comprises a polyolefin inner layer.

8. The blood storage device of claim 1, wherein said inner collapsible blood container 202 comprises PVC doped with diethylhexyl phthalate (DEHP).

9. The blood storage device of claim 1, wherein said inner collapsible blood container 202 has a moisture vapor transmission rate (MVTR) of 10 g/m$^2$/24 hrs or less when tested at a temperature of 23±2° C.

10. The blood storage device of claim 1, wherein said oxygen sorbent 207 further comprises a carbon dioxide sorbent.

11. The blood storage device of claim 10, wherein said oxygen sorbent 207 is provided as a single sachet comprising 8 grams of sorbent, situated outside of said inner collapsible blood container 202.

12. The blood storage device of claim 1, wherein said oxygen sorbent 207 has a capacity of at least 100 cc oxygen.

13. The blood storage device of claim 1, wherein said blood storage device 20 includes from 0.5 to 150 grams of said oxygen sorbent 207 in one or more sachets.

14. The blood storage device of claim 1, wherein said tubing 205 comprises PVC having a Barrer value of less than 3 Barrer.

15. The blood storage device of claim 1, wherein said outer layer 308 consists of polyethylene (PE), said inner layer 306 consists of PVC, and said intermediate oxygen barrier layer 307 consists of ethylene-vinyl acetate (EVA).

16. The blood storage device of claim 1, further comprising a spacer 213 and a headspace comprising a volume between said outer receptacle 201 and said inner collapsible blood container 202, wherein the headspace is maintained at a partial pressure of oxygen (PO$_2$) of less than 15 millimeters of mercury (mmHg) during a storage period of at least 64 days.

17. The blood storage device of claim 16, wherein said spacer 213 is selected from the group consisting of a mesh, a molded mat, a woven mat, a non-woven mat, an open cell foam, a strand veil, and a strand mat.

18. The blood storage device of claim 1, further comprising an oxygen indicator.

19. The blood storage device of claim 1, wherein said oxygen depleted blood stored in said inner collapsible blood container 202 maintains an oxygen saturation level (SO$_2$) during a storage period that increases by less than 5% over said oxygen saturation level at the beginning of storage.

20. The blood storage device of claim 1, wherein said inner collapsible blood container 202 has an oxygen permeability of between 3 and 350 Barrer.

\* \* \* \* \*